US010323215B2

(12) United States Patent
Fuchs et al.

(10) Patent No.: US 10,323,215 B2
(45) Date of Patent: Jun. 18, 2019

(54) SOLID POLYMER COMPOSITION OBTAINED BY POLYMERIZATION OF AN ACID GROUP CONTAINING MONOMER IN THE PRESENCE OF A POLYETHER COMPOUND

(71) Applicant: BASF SE, Ludwigshafen (DE)

(72) Inventors: Yannick Fuchs, Weinheim (DE); Helmut Witteler, Wachenheim (DE); Heike Weber, Mannheim (DE); Alejandra Garcia Marcos, Ludwigshafen (DE); Jürgen Detering, Limburgerhof (DE)

(73) Assignee: BASF SE, Ludwigshafen Am Rhein (DE)

( * ) Notice: Subject to any disclaimer, the term of this patent is extended or adjusted under 35 U.S.C. 154(b) by 293 days.

(21) Appl. No.: 14/902,371

(22) PCT Filed: Jul. 2, 2014

(86) PCT No.: PCT/EP2014/064084
§ 371 (c)(1),
(2) Date: Dec. 31, 2015

(87) PCT Pub. No.: WO2015/000970
PCT Pub. Date: Jan. 8, 2015

(65) Prior Publication Data
US 2016/0369209 A1 Dec. 22, 2016

(30) Foreign Application Priority Data
Jul. 3, 2013 (EP) .................................... 13174938

(51) Int. Cl.
| | |
|---|---|
| *C11D 3/37* | (2006.01) |
| *C08F 2/24* | (2006.01) |
| *C08F 2/44* | (2006.01) |
| *C09D 4/06* | (2006.01) |
| *C08F 283/06* | (2006.01) |
| *C08F 120/06* | (2006.01) |
| *C11D 1/722* | (2006.01) |
| *C11D 11/00* | (2006.01) |
| *C11D 17/00* | (2006.01) |
| *C08L 71/02* | (2006.01) |
| *C08F 20/06* | (2006.01) |
| *C08L 33/02* | (2006.01) |
| *C09J 133/02* | (2006.01) |
| *C11D 3/386* | (2006.01) |
| *C11D 3/395* | (2006.01) |
| *A61K 8/81* | (2006.01) |
| *A61K 47/32* | (2006.01) |
| *C09D 133/02* | (2006.01) |

(52) U.S. Cl.
CPC .......... *C11D 3/3757* (2013.01); *A61K 8/8152* (2013.01); *A61K 47/32* (2013.01); *C08F 2/24* (2013.01); *C08F 2/44* (2013.01); *C08F 20/06* (2013.01); *C08F 120/06* (2013.01); *C08F 283/06* (2013.01); *C08L 33/02* (2013.01); *C08L 71/02* (2013.01); *C09D 4/06* (2013.01); *C09D 133/02* (2013.01); *C09J 133/02* (2013.01); *C11D 1/722* (2013.01); *C11D 3/3707* (2013.01); *C11D 3/386* (2013.01); *C11D 3/395* (2013.01); *C11D 11/0017* (2013.01); *C11D 11/0023* (2013.01); *C11D 17/003* (2013.01)

(58) Field of Classification Search
CPC .. C08F 2/24; C08F 2/44; C08F 283/06; C08F 120/06; C11D 3/3757; C09D 4/06
See application file for complete search history.

(56) References Cited

U.S. PATENT DOCUMENTS

| | | | |
|---|---|---|---|
| 3,887,806 A | 6/1975 | Rodak et al. | |
| 4,237,253 A | 12/1980 | Jacquet et al. | |
| 4,435,307 A | 3/1984 | Barbesgaard et al. | |
| 4,604,224 A | 8/1986 | Cheng | |
| 4,814,101 A | 3/1989 | Schieferstein et al. | |
| 5,227,446 A | 7/1993 | Denzinger et al. | |
| 5,360,569 A | 11/1994 | Madison et al. | |
| 5,399,286 A | 3/1995 | Funhoff et al. | |
| 5,427,936 A | 6/1995 | Moeller et al. | |
| 5,661,220 A * | 8/1997 | Faul ..................... | B01D 17/047 516/184 |
| 5,747,635 A | 5/1998 | Kroner et al. | |
| 5,756,456 A | 5/1998 | Ho et al. | |
| 5,830,956 A | 11/1998 | Stockhausen et al. | |

(Continued)

FOREIGN PATENT DOCUMENTS

| | | |
|---|---|---|
| CA | 960144 A | 12/1974 |
| CA | 964215 A | 3/1975 |

(Continued)

OTHER PUBLICATIONS

International Search Report for PCT/EP2014/064084 dated Sep. 18, 2014.
Bailey, Jr. et al., "Some Factors Affecting the Molecular Association of Poly(Ethylene Oxide) and Poly(Acrylic Acid) in Aqueous Solution", American Chemical Society, Division of Polymer Chemistry, vol. 1, Issue 2, pp. 202-205 (1960).
Bromberg, "Novel Family of Thermogelling Materials via C?C Bonding between Poly(acrylic acid) and Poly(ethylene oxide)-b-poly(propylene oxide)-b-poly(ethylene oxide)", Journal of Physical Chemistry B, vol. 102, No. 11, pp. 1956-1963 (1998).

(Continued)

Primary Examiner — Peter D. Mulcahy
(74) Attorney, Agent, or Firm — Drinker Biddle & Reath LLP

(57) ABSTRACT

The present invention relates to a process for preparing a polymer composition, in which an α,β-ethylenically unsaturated carboxylic acid is subjected to a free-radical polymerization in the presence of at least one polyether component, to the polymer composition obtainable by this process and to the use thereof.

47 Claims, 1 Drawing Sheet

(56) References Cited

U.S. PATENT DOCUMENTS

| | | | |
|---|---|---|---|
| 5,880,252 A | 3/1999 | Kim et al. | |
| 7,754,804 B2 | 7/2010 | Mukherjee et al. | |
| 2003/0157170 A1 | 8/2003 | Liggins et al. | |
| 2004/0033929 A1 | 2/2004 | Bertleff et al. | |
| 2007/0117903 A1 | 5/2007 | Mukherjee et al. | |
| 2009/0099053 A1 | 4/2009 | Yoneda et al. | |
| 2011/0150796 A1* | 6/2011 | Kim | C08F 2/005 424/59 |
| 2011/0245130 A1 | 10/2011 | Dupont et al. | |

FOREIGN PATENT DOCUMENTS

| | | |
|---|---|---|
| CA | 2066226 A1 | 3/1991 |
| CA | 2038332 A1 | 9/1991 |
| CA | 2061174 A1 | 8/1992 |
| CA | 2153660 A1 | 7/1994 |
| CA | 2818703 * | 5/2012 |
| CA | 2818703 A1 | 5/2012 |
| DE | 2150557 A1 | 6/1972 |
| DE | 2817369 A1 | 10/1978 |
| DE | 3708451 A1 | 10/1988 |
| DE | 3929973 A1 | 3/1991 |
| DE | 4106355 A1 | 9/1992 |
| DE | 4313909 A1 | 11/1994 |
| DE | 4326772 A1 | 2/1995 |
| DE | 4333238 A1 | 4/1995 |
| DE | 4415623 A1 | 11/1995 |
| DE | 10338828 A1 | 3/2005 |
| EP | 001004 B1 | 2/1982 |
| EP | 0214761 A2 | 3/1987 |
| EP | 0218272 A1 | 4/1987 |
| EP | 0238023 A2 | 9/1987 |
| EP | 0258068 A2 | 3/1988 |
| EP | 0305216 A1 | 3/1989 |
| EP | 0331376 A2 | 9/1989 |
| EP | 0396303 A2 | 11/1990 |
| EP | 0451508 A1 | 10/1991 |
| EP | 0453003 A2 | 10/1991 |
| EP | 0454126 A1 | 10/1991 |
| EP | 0495257 A1 | 7/1992 |
| EP | 0499068 A1 | 8/1992 |
| EP | 0581452 A1 | 2/1994 |
| EP | 511037 B1 | 9/1994 |
| EP | 0639592 A1 | 2/1995 |
| EP | 656914 B1 | 1/1997 |
| EP | 0877002 A2 | 11/1998 |
| EP | 0971997 A1 | 1/2000 |
| GB | 1296839 A | 11/1972 |
| GB | 1372034 A | 10/1974 |
| JP | 64-74992 A | 3/1989 |
| JP | H07053993 A | 2/1995 |
| JP | 2004511624 A | 4/2004 |
| JP | 2007254679 A | 10/2007 |
| JP | 2010077427 A | 4/2010 |
| JP | 2012177007 A | 9/2012 |
| RU | 2126019 C1 | 2/1999 |
| WO | WO-8809367 A1 | 12/1988 |
| WO | WO-8906270 A1 | 7/1989 |
| WO | WO-8906279 A1 | 7/1989 |
| WO | WO-9009446 A1 | 8/1990 |
| WO | WO-9116422 A1 | 10/1991 |
| WO | WO-9401486 A1 | 1/1994 |
| WO | WO-9412621 A1 | 6/1994 |
| WO | WO-9421777 A1 | 9/1994 |
| WO | WO-9501426 A1 | 1/1995 |
| WO | WO-9840452 A1 | 9/1998 |
| WO | WO-0055044 A1 | 9/2000 |
| WO | WO-0183660 A1 | 11/2001 |
| WO | WO-2004099274 A1 | 11/2004 |
| WO | WO-2005012378 A1 | 2/2005 |
| WO | WO-2008139151 A1 | 11/2008 |
| WO | WO-2010026178 A2 | 3/2010 |
| WO | WO-2012/069440 A1 * | 5/2012 |
| WO | WO-2012069440 A1 | 5/2012 |
| WO | WO-2015/000969 A2 | 1/2015 |
| WO | WO-2015/000971 A1 | 1/2015 |

OTHER PUBLICATIONS

Bromberg, "Polyether-Modified Poly(acrylic acid):? Synthesis and Applications", Journal of Physical Chemistry B, vol. 37, No. 11, pp. 4267-4274 (1998).

Wu et al., "A Novel Thermosetting Gel Electrolyte for Stable Quasi-Solid-State Dye-Sensitized Solar Cells", Advanced Materials, vol. 19, pp. 4006-4011 (2007).

Li et al., "The effects of polymer gel electrolyte composition on performance of quasi-solid-state dye-sensitized solar cells", Journal of Solid State Electrochemistry, vol. 15, No. 6, pp. 1271-1277 (2011).

Russian Office Action for Russian Application No. 2016103333, dated Mar. 5, 2018.

Japanese Office Action with English Translation for Japanese Application No. 522601/2016, dated Apr. 17, 2018.

* cited by examiner

110
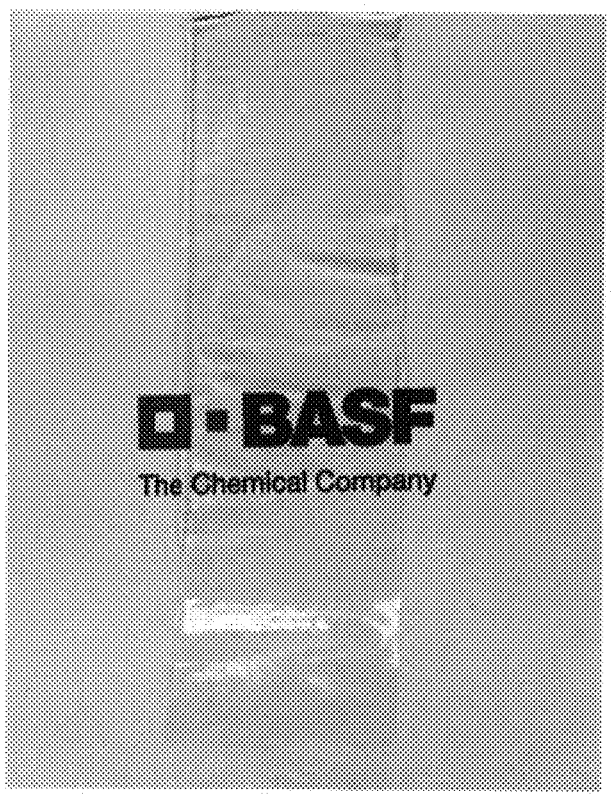

SOLID POLYMER COMPOSITION OBTAINED BY POLYMERIZATION OF AN ACID GROUP CONTAINING MONOMER IN THE PRESENCE OF A POLYETHER COMPOUND

CROSS-REFERENCE TO RELATED APPLICATIONS

This application is a national stage application (under 35 U.S.C. § 371) of PCT/EP2014/064084, filed Jul. 2, 2014, which claims benefit of European Application No. 13174938.4, filed Jul. 3, 2013, both of which are incorporated herein by reference in their entirety.

BACKGROUND OF THE INVENTION

The present invention relates to a process for preparing a polymer composition, in which an α,β-ethylenically unsaturated carboxylic acid is subjected to a free-radical polymerization in the presence of at least one polyether component, to the polymer composition obtainable by this process in the form of a solid substance, especially of a film, of a coating on a substrate or of a particulate solid, and to the use of such a polymer composition.

STATE OF THE ART

A multitude of demands to be fulfilled simultaneously are made on washing, cleaning and dishwashing compositions, both in terms of their cleaning performance and in terms of the manufacturing and supply forms. Good performance properties should go hand in hand with convenient user dosage and simplification of the steps needed to conduct a washing or cleaning procedure. In this context, a multitude of dosage forms have recently been marketed, including not only the conventional powders and liquid formulations but also tableted products ("tabs"), film-ensheathed individual portions and dosage systems for multiple dosage of washing and cleaning compositions. Current dosage forms may comprise a multitude of separately formulated active ingredients and auxiliaries which are released individually in the cleaning process. There is still a great need here both for active substances and for components that are used in films and coatings for the dosage forms. Preference is given to components which display a multiple effect, for example as a film-forming component which is soluble under the cleaning conditions and, after it has dissolved, is involved in the cleaning process.

It is known that polyvinyl alcohol can be used as a water-soluble packaging and coating material for washing, cleaning and dishwashing compositions, etc. A disadvantage is that polyvinyl alcohol itself does not have detergent action and is not actively involved in the cleaning process.

In domestic detergents, washing compositions, dishwashing compositions, rinse aids, cosmetics, pharmaceuticals, and in formulations for industrial applications, polyethers or surfactants containing ether groups are frequently used together with polymers of α,β-ethylenically unsaturated carboxylic acids and especially polyacrylic acid, in which case polyacrylic acid often assumes the role of an incrustation inhibitor or dispersant.

The problem is that polyethers and surfactants containing ether groups are frequently of zero or only limited compatibility with polyacrylic acid, and so mixing results in phase separation or in precipitates, which greatly restricts the possible uses of at least one of the components. Moreover, polyethers and surfactants are frequently in a waxlike or tacky consistency. While this is generally uncritical for the production of adhesive formulations, these components can be added to pulverulent formulations only to a small degree, because the flowability of the powder is otherwise lost. It is also especially difficult to provide transparent films and coatings based on polyethers or surfactants containing ether groups together with polymers of unsaturated carboxylic acids, as preferred by the consumer both because of their performance properties and for esthetic reasons. There is therefore a need for compositions based on polymers of unsaturated carboxylic acids and polyethers which can be provided in the form of a solid substance, especially in the form of a film (for example as a sheath for a liquid dishwashing, washing or cleaning composition) or a coating on a substrate (for example on a dishwashing, washing or cleaning composition tablet) or in the form of a particulate solid (for example of a pelletized material or powder).

F. E. Bailey et al. describe, in Polymer Preprints, American Chemical Society, Division of Polymer Chemistry, 1960, vol. 1, issue 2, p. 202-205 and the literature cited therein, the formation of molecular association complexes of ethylene oxide polymers having a very high molecular weight with polymeric acids such as polyacrylic acid in aqueous solutions. The polymerization of acrylic acid in the presence of the ethylene oxide polymers is not described.

EP 0971997 B1 describes a liquid detergent formulation comprising a nonionic surfactant and an anionic polymer. The nonionic surfactant may be an ethoxylated $C_8$-$C_{18}$ alcohol and the anionic polymer may be polyacrylic acid. The polymer has a molecular weight of more than 100 000 g/mol. There is no description of production of the formulation by polymerizing at least one polymer containing acid groups in the presence of the nonionic surfactant.

WO 2001/83660 describes the preparation of powders from surfactants and water-soluble polymers by spray-drying. The process of spray-drying is specifically inapplicable to mixtures comprising polyacrylic acid, because it forms, together with polyethers and polyether-containing surfactants, a rubber-like coagulate which cannot be processed in a spray tower because of its viscosity.

EP 0 499 068 A1 describes reaction products of alkoxylates and vinylic monomers, at least some of which bear functional groups which can react with the OH groups of the alkoxylates in a condensation. The reaction products are prepared by either polymerizing the vinylic monomers in the presence of the alkoxylates and then subjecting the product of the polymerization to a condensation, or by first polymerizing the vinylic monomers and then subjecting the product of the polymerization to a condensation with the alkoxylates. In the case that acrylic acid is used as vinylic monomer, the reaction product in each case is thus an ester of polyacrylic acid. In the working examples, the alkoxylates used are exclusively EO-PO block copolymers having a high PO content and polytetrahydrofuran. The polymers described serve as emulsion breakers for rapid dewatering of crude oils. They are prepared by bulk polymerization in a first variant, in which case the end product is added as a solidified melt or after being taken up in a solvent for the crude oil emulsion. In a second variant, preparation is effected by solution polymerization in a solvent suitable for use as an emulsion breaker. Suitable solvents are aromatics, aliphatic and cycloaliphatic hydrocarbons, acetone, cyclohexanone, THF and dioxane. There is no description of use of the polymers in solid form, specifically in the form of a film or of a solid coating on a substrate or in particulate form.

A similar process is described in DE 4326772 A1, wherein toluene or xylene is used as solvent. The use of aromatic solvents is undesirable for products which are to be used in consumer goods, since the complete removal of the solvent is very time-consuming and energy-intensive. The reaction products are liquids which are described as esterified polyacrylic acids. Ester formation runs counter to the effect of the polymer, for example as an incrustation inhibitor, and is undesirable in applications where the use of very substantially pure polyacrylic acid is required.

X. Li et al. in Journal of Solid State Electrochemistry (2011), 15(6), 1271-1277) and J. H. Wu et al. in Advanced Materials, 2007, 19, 4006-4011, describe preparation processes for polyacrylic acid-polyethylene glycol gels. These publications teach the use of N,N'-methylenebisacrylamide as crosslinker in acrylic acid polymerization, so that the polymers obtained are not water-soluble. Moreover, the use of a crosslinker results in a very high molecular weight, which makes the polymers unsuitable as incrustation inhibitors. There is no description of use of the polymers in the form of films, solid coatings or polymer particles.

WO 2008/139151 A1 describes a process in which polyethylene glycol is mixed with acrylic acid, isobornyl acrylate and further components, and cured by UV exposure to give a solid gel. On the basis of the composition, it is apparent to the person skilled in the art that the gel is not water-soluble. The gels serve as an indicator that a data carrier, for example a computer-readable compact disk, has not been used before.

WO 2010/026178/A2 describes, on page 62 and example 19, a precipitation polymerization in which acrylic acid is polymerized in the presence of glyceryl monostearate and an alkyl-terminated polyethylene glycol methacrylate. The latter is an associative monomer and not a surfactant containing polyether groups in the context of the present invention. The process additionally requires the use of a large amount of organic solvents based on a relatively small amount of acrylic acid and surfactant.

Lev Bromberg describes, in Journal of Physical Chemistry B (1998), 102, 11, 1956-1963, a material having thermoreversible gel formation, which is prepared by polymerizing acrylic acid in the presence of a PEO-PPO-PEO block copolymer. The reaction is effected in the absence of external solvents, in order to achieve a high proportion of branching and crosslinking in the products obtained. These are neither water-soluble nor transparent. Possible fields of use mentioned for these polymers, merely in quite general terms, are pharmacy and nutrition (p. 1956, left-hand column, "Introduction").

WO 2005/012378 describes aqueous dispersions of water-soluble polymers of anionic monomers and the use thereof as thickeners for aqueous systems. They are prepared by polymerizing anionic monomers in the presence of two water-soluble polymers from different classes, and these may be polyalkylene glycols among other polymers. Example 4 (page 19 lines 14-27) relates to the polymerization of acrylic acid in the presence of two different polypropylene glycols and of maltodextrin. The dispersions are used, inter alia, in personal care products and in washing and cleaning compositions. There is no description of use in the form of films, solid coatings or polymer particles.

EP 0 639 592 A1 describes graft copolymers obtainable by polymerizing a (meth)acrylic acid-containing polymer composition in the presence of a polyether compound having more than 80 mol % of ethylene oxide units. The polymerization is effected essentially without solvent and at temperatures above 100° C. It is regarded as critical for the achievement of high grafting levels that the solvent content of the reaction mixture is never more than 5% by weight. The polymers obtained serve as builders for liquid washing compositions or, optionally after postcrosslinking, as water-absorbing resins.

WO 2004/099274 describes a process for preparing polymer mixtures by polymerizing monomers of the (meth) acrylic acid type in the presence of a compound having a polyalkylene glycol structure. The polymer mixtures obtained are to contain proportions of graft copolymers, the polyalkylene glycol component and the (meth)acrylic acid component remaining homogeneous in the mixture even after prolonged storage. The polymerization is necessarily effected in the presence of water having a high water content in the initial charge at the start of the reaction. The polymer mixtures obtained by the process are suitable for various detergent applications, especially for prevention of resoiling.

It is an object of the present invention to provide a novel polymer composition and a process for preparation thereof, the polymer composition comprising a homo- or copolymer having a high proportion of incorporated acid monomers and a polyether component. At the same time, the above-described disadvantages of the prior art are to be avoided. It is to be possible to provide the polymer compositions in the form of a solid substance, specifically in the form of a film, a coating on a substrate or a particulate solid. They are to be especially suitable as a water-soluble packaging or coating material, for example for washing, cleaning and dishwashing compositions. Furthermore, they are themselves to have use properties as are typical of polymers based on at least one α,β-ethylenically unsaturated carboxylic acid and polyethers, for example interfacial action, deposit-inhibiting action, incrustation-inhibiting action, etc. It is especially also to be possible to provide the inventive polymer compositions in the form of particles (e.g. powder or pelletized material), and these are to be suitable, for example, as active component for solid washing, cleaning and dishwashing compositions.

It has now been found that, surprisingly, this object is achieved when the polymer composition is prepared by subjecting a monomer composition based on at least one α,β-ethylenically unsaturated carboxylic acid to a free-radical polymerization in the presence of the polyether component.

SUMMARY OF THE INVENTION

The invention firstly provides a process for preparing a polymer composition, in which
a) a monomer composition M) is provided, comprising
   A) at least one α,β-ethylenically unsaturated carboxylic acid, and
   B) less than 0.1% by weight, based on the total weight of the monomer composition M), of crosslinking monomers having two or more than two polymerizable α,β-ethylenically unsaturated double bonds per molecule,
b) the monomer composition M) provided in step a) is subjected to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof.

The invention relates especially to a process for preparing a solid polymer composition, particularly in the form of a film or in the form of a solid coating on a substrate or in particulate form.

In a specific embodiment, the at least one α,β-ethylenically unsaturated carboxylic acid A) is partly or fully replaced by at least one unsaturated sulfonic acid or at least one unsaturated phosphonic acid (=component C).

In a specific embodiment, the polyether component PE) comprises or the polyether component PE) consists of at least one polyetherol or a mono- or di-($C_1$-$C_2$-alkyl ether) thereof comprising predominantly or exclusively ethylene oxide units as alkylene oxide units. When the polyether component PE) comprises a polyetherol having repeat propylene oxide units or a mono- or di-($C_1$-$C_6$-alkyl ether) of a polyetherol having repeat propylene oxide units, the proportion of these repeat propylene oxide units preferably averages not more than 18 units per molecule. The proportion of repeat propylene oxide units especially averages not more than 15 units per molecule, more especially not more than 10 units per molecule.

In a further specific embodiment, the reaction mixture during the polymerization in step b) and the polymer composition obtained in step b) are not subjected to any condensation with removal of a low molecular weight reaction product and/or in the presence of a condensation catalyst.

In a first variant of the process according to the invention, a polymer composition is obtained in the form of a transparent film. In a second variant of the process according to the invention, a polymer composition is obtained in the form of a solid coating on a substrate. In a third variant of the process according to the invention, a polymer composition is obtained in the form of a particulate solid substance.

The invention further provides a process for preparing a polymer composition, as defined above and hereinafter, in the form of a film, in which a) a monomer composition M) is provided, comprising
   A) at least one α,β-ethylenically unsaturated carboxylic acid, and
   B) less than 0.1% by weight, based on the total weight of the monomer composition M), of crosslinking monomers having two or more than two polymerizable α,β-ethylenically unsaturated double bonds per molecule,
b) the monomer composition M) provided in step a) is subjected to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof, and
c) the polymer obtained in step b), optionally after addition of at least one active ingredient and/or at least one additive, is subjected to a film-forming operation, preferably selected from blow-molding, thermoforming, casting and calendering.

The invention further provides a process for preparing a polymer composition, as defined above and hereinafter, in the form of a solid coating on a substrate, in which a) a monomer composition M) is provided, comprising
   A) at least one α,β-ethylenically unsaturated carboxylic acid, and
   B) less than 0.1% by weight, based on the total weight of the monomer composition M), of crosslinking monomers having two or more than two polymerizable α,β-ethylenically unsaturated double bonds per molecule,
b) the monomer composition M) provided in step a) is subjected to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof, and
c) the polymer obtained in step b), optionally after addition of at least one active ingredient and/or at least one additive and/or at least one solvent and optionally while heating, is converted to a free-flowing form, applied to a substrate and allowed to solidify.

The invention further provides a process for preparing a polymer composition, as defined above and hereinafter, in particulate form, in which a) a monomer composition M) is provided, comprising
   A) at least one α,β-ethylenically unsaturated carboxylic acid, and
   B) less than 0.1% by weight, based on the total weight of the monomer composition M), of crosslinking monomers having two or more than two polymerizable α,β-ethylenically unsaturated double bonds per molecule,
b) the monomer composition M) provided in step a) is subjected to a free-radical polymerization in the presence of at least one polyether component PE) selected from polyetherols having a number-average molecular weight of at least 200 g/mol and the mono- and di-($C_1$-$C_6$-alkyl ethers) thereof, surfactants containing polyether groups and mixtures thereof, and
c) the polymer obtained in step b), optionally after addition of at least one additive and/or at least one solvent and optionally while heating, is converted to a free-flowing form and a particulate composition is formed therefrom.

The invention further provides a polymer composition obtainable by a process as defined above and hereinafter.

The invention further provides a polymer composition as defined above and hereinafter, in the form of a transparent film, a solid coating on a substrate or a particulate solid substance.

The invention further provides a polymer composition in the form of a film or a coating on a substrate, comprising at least one active ingredient.

In a specific execution, the active ingredient is selected from enzymes, builders, bleaches, surfactants, bases, corrosion inhibitors, defoamers, dyes, fragrances, fillers, tableting aids, disintegrants, thickeners, solubilizers, organic solvents, electrolytes, pH modifiers, perfume carriers, fluorescers, hydrotropes, antiredeposition agents, optical brighteners, graying inhibitors, shrink inhibitors, crease inhibitors, dye transfer inhibitors, active antimicrobial ingredients, antioxidants, corrosion inhibitors, antistats, ironing aids, hydrophobizing and impregnating agents, swell and antislip agents, UV absorbers and mixtures thereof.

A specific execution of the invention is a polymer composition in the form of a film or a coating on a substrate, comprising at least one enzyme. A further specific execution of the invention is a sheath for a washing composition portion, cleaning composition portion or dishwashing composition portion, in the form of a film or a coating on a substrate, comprising at least one enzyme.

The invention further provides for the use of a polymer composition as defined above and hereinafter
   in washing and cleaning compositions,
   in dishwashing compositions and in rinse aids,
   in hygiene products,
   in cosmetic compositions, in pharmaceutical compositions,
in crop protection compositions,
in wetting agents,
in lacquers, coating compositions, adhesives, leather treatment compositions or textile care compositions, etc.,
in the development and/or exploitation of underground mineral oil and/or natural gas deposits.

The invention further provides for the use of a polymer composition as defined above and hereinafter in liquid or solid washing compositions and in cleaning compositions for solid surfaces.

The invention further provides for the use of a polymer composition as defined above and hereinafter for forming a sheath or in the sheath of a liquid or solid washing and cleaning composition.

The invention further provides for the use of a polymer composition as defined above and hereinafter as a coating film or as a component of a coating film for a pharmaceutical composition, animal medicament or edible or drinkable composition, specifically for production of coated tablets, pellets, microcapsules, pellets or crystals.

The invention further provides a sheath for a washing composition portion, cleaning composition portion or dishwashing composition portion, comprising or consisting of a polymer composition obtainable by a process as defined above and hereinafter.

The invention further provides an adhesive composition, comprising or consisting of a polymer composition obtainable by a process as defined above and hereinafter. The inventive adhesive composition is suitable for a multitude of uses, for example for coated labels, especially plasticizer-free and/or self-adhesive and/or redetachable paper labels.

DESCRIPTION OF THE INVENTION

The process according to the invention and the polymer compositions obtained thereby have the following advantages:

The process according to the invention is suitable for preparation of compositions based on polymers of unsaturated acids (especially unsaturated carboxylic acids) and polyethers, which can be provided in the form of a solid substance. The process is variable in terms of the solid polymer composition obtained. It is suitable firstly for preparation of solid polymer compositions in the form of a film. In this context, it is possible for the first time to provide transparent water-soluble films based on polyacrylic acid and polyethers.

The process according to the invention is additionally suitable for preparation of a coating on a substrate, for example in or on a dishwashing, washing or cleaning composition tablet.

The process according to the invention is additionally suitable for preparation of solid polymer particulate and especially pelletized and pulverulent polymer compositions. Advantageously, these compositions are tacky only to a minor degree, if at all, and are suitable for preparation of free-flowing solid formulations. The provision of these specific particulate polymer compositions is possible through selection of a suitable glass transition temperature and/or polyether component PE), as explained in detail hereinafter.

The polymer compositions obtained by the process according to the invention are notable firstly for good film-forming properties and secondly for their suitability as an active component, for example of washing, cleaning and dishwashing formulations. Thus, the inventive polymer compositions are suitable, for example, as complexing agents, soil release polymers or incrustation inhibitors. They are advantageously suitable as a substitute for polyvinyl alcohol in the provision of films and coatings for various dosage forms.

On the basis of the aforementioned properties, the inventive polymer compositions can be used in a multitude of dos'age forms and in several components of these dosage forms. For example, it is possible for a single portion of a washing, cleaning or dishwashing formulation to comprise the inventive polymer component in a liquid or solid active component and/or in the coating of at least one solid component and/or in the sheath of at least one liquid or solid active component.

The process according to the invention enables the substantial or complete elimination of crosslinking monomers in the preparation of the polymer compositions. These are therefore advantageously water-soluble.

The polymer compositions obtained by the process according to the invention are notable both for high compatibility between polyether component and polyacrylic acid and for high compatibility with further surfactants.

The dissolution characteristics of the polymer compositions obtained by the process according to the invention can be controlled within a wide range, for example via the type and amount of monomers used. Insoluble compositions or those having a slow dissolution rate are advantageously suitable for providing active combinations with a retarded release profile.

The polymer compositions obtained by the process according to the invention are advantageously suitable for production of films or coatings comprising at least one active ingredient. It is thus possible, for example, to provide a sheath for a washing composition portion, cleaning composition portion or dishwashing composition portion, from which at least one active ingredient is released in a controlled manner in the course of the washing operation, cleaning operation or dishwashing operation.

The process according to the invention is additionally suitable for preparation of polymer compositions for adhesive compositions. The provision of these specific polymer compositions is possible through selection of a suitable glass transition temperature and/or polyether component PE), as explained in detail hereinafter.

In the context of this application, some compounds which can be derived from acrylic acid and methacrylic acid are abbreviated by insertion of the "(meth)" syllable into the compound derived from acrylic acid.

In the context of the present invention, $C_1$-$C_6$-alkyl is a linear or branched alkyl radical having 1 to 5 carbon atoms. Examples of these are methyl, ethyl, propyl, isopropyl, n-butyl, sec-butyl, isobutyl, tert-butyl, pentyl and positional isomers thereof.

$C_7$-$C_{30}$-Alkyl is a linear or branched alkyl radical having 6 to 30 carbon atoms. Examples thereof are heptyl, octyl, 2-ethylhexyl, nonyl, decyl, 2-propylheptyl, undecyl, dodecyl, tridecyl, tetradecyl, pentadecyl, hexadecyl, heptadecyl, octadecyl, nonadecyl, eicosyl, henicosyl, docosyl, tricosyl, tetracosyl and positional isomers thereof.

The inventive polymer compositions are prepared by free-radical polymerization of the monomer composition M) in the presence of at least one polyether component PE) which generally does not have any copolymerizable double bond. This affords specific polymer compositions having advantageous properties. Without being bound to a theory, this may be attributable, for example, to an effect of the polyether component PE) as a protective colloid or emulsifier. This may also result, for example, from at least partial grafting onto the polyether component as graft base. However, mechanisms other than grafting are also conceivable. The inventive polymer compositions quite generally comprise the process products of free-radical polymerization, which are understood to mean, for example, graft polymers, homo- and copolymers of the monomers present in the monomer mixture M), mixtures of graft polymers with ungrafted compounds in the polyether component PE) and any desired mixtures.

In a specific preferred execution, during and after the polymerization in step b), the reaction mixture and the polymer composition obtained in step b) are not subjected to any condensation with removal of a low molecular weight reaction product and/or in the presence of a condensation catalyst. This is understood to mean that specifically no additional measures are conducted with the aim of increasing the ester group content of the polymer composition obtained by the process according to the invention. In another specific execution, ester formation is permitted during and/or after the polymerization in step b).

Specifically, the inventive polymer composition is in solid form under standard conditions (23° C., 1013 mbar). In the context of the invention, the terms "solid substance" and "in solid form" are understood to mean either a solvent-free solid or solid compositions comprising an inventive polymer composition and at least one solvent. Preferably, the solvent content of the solid compositions is not more than 10% by weight, more preferably not more than 5% by weight, especially not more than 2% by weight, based on the total weight of polymer composition and solvent. Suitable solvents and solvent mixtures are described hereinafter as component S).

The inventive polymer composition is not in the form of a gel. Compositions in gel form are the subject of parallel applications. In general, inventive polymer compositions including more than 10% by weight of solvent, based on the total weight of polymer composition and solvent, can form gels.

In the context of the present invention, the term "film" refers to a flat structure having essentially a two-dimensional format. The thickness of the inventive films is preferably 0.5 μm to 10 mm, more preferably 1 μm to 5 mm. The length and/or width of the film is generally at least 5 mm and preferably at least 10 mm. The maximum length and/or width of the film is generally uncritical and, according to the field of use, may be in the millimeter, centimeter or meter range.

If the inventive polymer compositions are in the form of a solid coating on a substrate, the thickness of the coating is preferably within a range from 0.5 μm to 10 mm, more preferably 1 μm to 5 mm.

In the context of the present invention, the terms "particulate solid substance" and "particulate polymer composition" refer to a composition comprising particles having a particle size ranging preferably from pulverulent particles to pellet size. Preferably, the particle size is within a range from about 50 μm to 10 mm, more preferably 100 μm to 5 mm.

The glass transition temperatures (Tg) described in the context of this application can be determined by means of differential scanning calorimetry (DSC). The DSC analysis on one and the same sample is appropriately repeated once or twice, in order to ensure a defined thermal history of the respective polyamide. The heating and cooling rates were 20 K/min.

For use in the form of a film or in the form of a coating on a substrate, preference is given to using flexible inventive polymer compositions having a low glass transition temperature $T_G$. Preferably, the inventive polymer compositions for use in the form of a film or in the form of a coating on a substrate have a glass transition temperature $T_G$ in the range from 0 to 50° C., preferably from 5 to 20° C.

For use in the form of a particulate solid substance, preference is given to using brittle inventive polymer compositions having a high glass transition temperature $T_G$.

Preferably, the inventive polymer compositions for use in the form of a particulate solid substance have a glass transition temperature $T_G$ in the range from 15 to 150° C., preferably from 30 to 130° C.

For use in an adhesive composition, preference is given to using inventive polymer compositions having a low glass transition temperature. Preferably, the inventive polymer compositions for use in adhesive compositions have a glass transition temperature $T_G$ in the range from −100 to +10° C., preferably from −80 to 0° C.

The glass transition temperature $T_G$ control can in principle be controlled via the type and proportion of the monomers and the molecular weight. A further means of controlling the glass transition temperature $T_G$ lies in the selection of the polyether component PE. The provision of an inventive polymer composition having the desired glass transition temperature $T_G$ is within the ability of the person skilled in the art and can be checked by means of routine measurements.

In a preferred execution of the first variant, the inventive polymer compositions are in the form of a transparent film. The transparency of a material is determined by its absorption and scattering characteristics, i.e. the light transmitted and the appearance looking through the material. The total transmission (transparency) is the ratio of transmitted light to incident light. The measure used for the transparency is the transmission τ: it is the quotient of the luminous flux $\Phi_n$ behind and $\Phi_v$ in front of the material to be tested, and is reported in percent. This value comprises, as well as the absorption, also the scattering and reflection losses. The transmission is generally determined in air and is reported as a function of wavelength.

In the context of the invention, the transparency $(T_L)$ is determined at a wavelength of 500 nm. The reference parameter used for maximum transparency ($T_L$ of 100%) is water.

Preferably, the inventive polymer composition in the form of a transparent film has a $T_L$ measured at 500 nm of at least 85%, more preferably of at least 90%, based on the transparency of water.

In a second variant of the process according to the invention, a polymer composition is obtained in the form of a solid substance.

Suitable characteristic material values for characterization of the polymer composition in the form of a solid substance are the storage modulus, the loss modulus (G") and the loss factor tan(δ) corresponding to the quotient G"/G'.

Monomer Composition M)
Carboxylic Acid Monomer A)

The α,β-ethylenically unsaturated carboxylic acid A) is preferably selected from acrylic acid, methacrylic acid, ethacrylic acid, α-chloroacrylic acid, crotonic acid, maleic acid, itaconic acid, citraconic acid, mesaconic acid, glutaconic acid, aconitic acid, fumaric acid and mixtures thereof. The monomers A) also include the salts of the aforementioned acids, especially the sodium, potassium and ammonium salts, and also the salts with amines. The monomers A) can be used as they are or as mixtures with one another. The proportions by weight stated all refer to the acid form.

Preferably, the at least one α,β-ethylenically unsaturated carboxylic acid is used in non-neutralized form for polymerization.

More preferably, component A) is selected from acrylic acid, methacrylic acid and mixtures thereof.

More particularly, exclusively acrylic acid is used as component A).

Component A) is preferably used in an amount of 50% to 100% by weight, more preferably 60% to 100% by weight, based on the total weight of the monomer composition M).

In a preferred embodiment, the monomer composition M) consists to an extent of at least 80% by weight, preferably to an extent of at least 90% by weight, especially to an extent of at least 95% by weight, based on the total weight of the monomers used, of acrylic acid.

Crosslinker B)

The inventive polymer composition comprises essentially uncrosslinked polymers. The monomer composition M) used for preparation of the inventive polymer composition therefore comprises only small amounts, if any, of crosslinking monomers B). Crosslinkers in the context of the invention are compounds having two or more than two polymerizable ethylenically unsaturated double bonds per molecule.

Preferably, crosslinkers B) are used in an amount of 0% to 0.1% by weight, more preferably 0% to 0.05% by weight, based on the total weight of the monomer composition M). In a specific embodiment, the monomer composition M) does not comprise any crosslinking monomers B) having two or more than two polymerizable α,β-ethylenically unsaturated double bonds per molecule.

Suitable crosslinkers B) are, for example, acrylic esters, methacrylic esters, allyl ethers or vinyl ethers of at least dihydric alcohols. The OH groups of the parent alcohols may be fully or partly etherified or esterified; however, the crosslinkers comprise at least two ethylenically unsaturated groups.

Examples of the parent alcohols are dihydric alcohols such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans each having molecular weights of 200 to 10 000 g/mol. Apart from the homopolymers of ethylene oxide and propylene oxide, it is also possible to use block copolymers of ethylene oxide or propylene oxide or copolymers incorporating ethylene oxide and propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose.

The polyhydric alcohols can of course also be used after reaction with ethylene oxide or propylene oxide, in the form of the corresponding ethoxylates and propoxylates respectively. The polyhydric alcohols can also first be converted to the corresponding glycidyl ethers by reaction with epichlorohydrin.

Further suitable crosslinkers B) are the vinyl esters or the esters of monohydric unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is also possible to esterify the monohydric unsaturated alcohols with polybasic carboxylic acids, for example malonic acid, tartaric acid, trimellitic acid, phthalic acid, terephthalic acid, citric acid or succinic acid.

Further suitable crosslinkers B) are esters of unsaturated carboxylic acids with the above-described polyhydric alcohols, for example oleic acid, crotonic acid, cinnamic acid or 10-undecenoic acid.

Suitable crosslinkers B) are also straight-chain or branched, linear or cyclic, aliphatic or aromatic hydrocarbons having at least two double bonds which, in the case of aliphatic hydrocarbons, must not be conjugated, e.g. divinylbenzene, divinyltoluene, octa-1,7-diene, deca-1,9-diene, 4-vinyl-1-cyclohexene, trivinylcyclohexane or polybutadienes having molecular weights of 200 to 20 000 g/mol.

Also suitable as crosslinkers B) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids such as acrylic acid, methacrylic acid, itaconic acid, maleic acid, or at least dibasic carboxylic acids as described above.

Also suitable as crosslinkers B) are triallylamine and triallylmonoalkylammonium salts, e.g. triallylmethylammonium chloride or methylsulfate.

Also suitable are N-vinyl compounds of urea derivatives, at least difunctional amides, cyanurates or urethanes, for example of urea, ethyleneurea, propyleneurea or tartarannide, N,N'-divinylethyleneurea or N,N'-divinylpropyleneurea.

Further suitable crosslinkers B) are divinyldioxane, tetraallylsilane or tetravinylsilane.

Unsaturated Sulfonic or Phosphonic Acids C)

The monomer composition M) may comprise at least one unsaturated sulfonic acid or phosphonic acid C) instead of component A). The monomer composition M) may also additionally comprise at least one unsaturated sulfonic acid or phosphonic acid as component C).

Component C) is preferably selected from 2-acrylamido-2-methylpropanesulfonic acid, vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, vinylphosphonic acid, allylphosphonic acid and mixtures thereof.

A preferred component C) is 2-acrylamido-2-methylpropanesulfonic acid.

The monomers C) also include the salts of the aforementioned acids, especially the sodium, potassium and ammonium salts, and also the salts with amines. The monomers C) can be used as they are or as mixtures with one another. The proportions by weight stated all refer to the acid form.

Preferably, the monomer composition M) consists to an extent of at least 80% by weight, preferably to an extent of at least 90% by weight, especially to an extent of at least 95% by weight, based on the total weight of the monomer composition M), of monomers A) and C). When the monomer composition M) comprises at least one monomer C), it is preferably used in an amount of 0.1 to 50% by weight, more preferably 1% to 25% by weight, based on the total weight of the monomer composition M).

Monomer Containing Ether Groups D)

The monomer composition M) may additionally comprise at least one monomer D) selected from compounds of the general formulae (I.a) and (I.b)

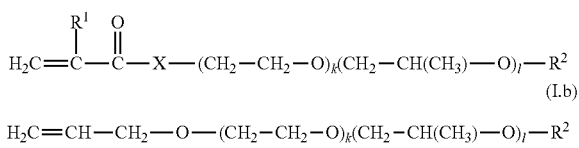

in which
the sequence of the alkylene oxide units is arbitrary,
k and l are each independently an integer from 0 to 1000, where the sum of k and l is at least 2, preferably at least 5,
$R^1$ is hydrogen or $C_1$-$C_8$-alkyl,
$R^2$ is hydrogen, $C_1$-$C_{30}$-alkyl, $C_2$-$C_{30}$-alkenyl or $C_5$-$C_8$-cycloalkyl,
X is O or a group of the formula $NR^3$ in which $R^3$ is H, alkyl, alkenyl, cycloalkyl, heterocycloalkyl, aryl or hetaryl.

In the formulae I.a) and I.b), k is preferably an integer from 1 to 500, more preferably 2 to 400, especially 3 to 250. Preferably, l is an integer from 0 to 100.

Preferably, $R^1$ in the formula I.a) is hydrogen, methyl, ethyl, n-propyl, isopropyl, n-butyl, sec-butyl, tert-butyl, n-pentyl or n-hexyl, especially hydrogen, methyl or ethyl.

Preferably, $R^2$ in the formulae I.a) and I.b) is n-octyl, 1,1,3,3-tetramethylbutyl, ethylhexyl, n-nonyl, n-decyl, n-undecyl, tridecyl, myristyl, pentadecyl, palmityl, heptadecyl, octadecyl, nonadecyl, arachinyl, behenyl, lignoceryl, cerotinyl, melissyl, palmitoleyl, linoleyl, linolenyl, stearyl, lauryl.

Preferably, X in the formula I.a) is O or NH, especially O.

Suitable polyether acrylates I.a) are, for example, the polycondensation products of the aforementioned α,β-ethylenically unsaturated mono- and/or dicarboxylic acids and the acid chlorides, acid amides and acid anhydrides thereof with polyetherols. Suitable polyetherols can be prepared easily by reacting ethylene oxide, propylene 1,2-oxide and/or epichlorohydrin with a starter molecule such as water or a short-chain alcohol $R^2$—OH. The alkylene oxides can be used individually, alternately in succession, or as a mixture. The polyether acrylates I.a) can be used alone or in mixtures to prepare the polymers used in accordance with the invention.

Suitable allyl alcohol alkoxylates I.b) are, for example, the etherification products of allyl chloride with appropriate polyetherols. Suitable polyetherols can be prepared easily by reacting ethylene oxide, propylene 1,2-oxide and/or epichlorohydrin with a starter alcohol $R^2$—OH. The alkylene oxides can be used individually, alternately in succession, or as a mixture. The allyl alcohol alkoxylates I.b) can be used alone or in mixtures to prepare the polymers used in accordance with the invention.

Monomers D) used are especially methyl diglycol acrylate, methyl diglycol methacrylate, ethyl diglycol acrylate or ethyl diglycol methacrylate. Preference is given to ethyl diglycol acrylate.

The monomer composition M) comprises preferably 0% to 50% by weight, more preferably 0% to 25% by weight, especially 0% to 10% by weight, based on the total weight of the monomer composition M), of at least one monomer containing ether groups D). When the monomer composition M) comprises at least one monomer D), then preferably in an amount of 0.1% to 50% by weight, more preferably 1% to 25% by weight, especially 1.5% to 10% by weight, based on the total weight of the monomer composition M).

Further Monomers E) to O)

The monomer composition M) may additionally comprise at least one further monomer other than monomers A) to D). Preferably, the monomer composition M) additionally comprises at least one comonomer selected from
E) vinylaromatics,
F) $C_2$-$C_8$ monoolefins, nonaromatic hydrocarbons having at least two conjugated double bonds,
G) esters of α,β-ethylenically unsaturated mono- and dicarboxylic acids with $C_1$-$C_{20}$-alkanols,
H) compounds having one free-radically polymerizable α,β-ethylenically unsaturated double bond and at least one cationogenic and/or cationic group per molecule,
I) esters of vinyl alcohol or allyl alcohol with $C_1$-$C_{30}$-monocarboxylic acids,
K) monomers containing amide groups,
L) esters of α,β-ethylenically unsaturated mono- and dicarboxylic acids with $C_2$-$C_{30}$-alkanediols, amides of α,β-ethylenically unsaturated mono- and dicarboxylic acids with $C_2$-$C_{30}$-amino alcohols having a primary or secondary amino group,
M) α,β-ethylenically unsaturated nitriles,
N) vinyl halides, vinylidene halides,
O) monomers having urea groups,
and mixtures thereof.

The monomer composition M) may comprise each of the further monomers E) to O) in an amount of 0% to 50% by weight, more preferably 0% to 25% by weight, especially 0% to 10% by weight, based on the total weight of the monomer composition M). When the monomer composition M) comprises at least one monomer E) to O), then preferably each in an amount of 0.1% to 50% by weight, more preferably 1% to 25% by weight, especially 1.5% to 10% by weight, based on the total weight of the monomer composition M). In a specific execution, the monomer composition M) does not comprise any further monomers E) to O).

Monomer E)

Preferred vinylaromatics E) are styrene, 2-methylstyrene, 4-methylstyrene, 2-(n-butyl)styrene, 4-(n-butyl)styrene, 4-(n-decyl)styrene and mixtures thereof. Particular preference is given to styrene and 2-methylstyrene, especially styrene.

Monomer F)

Preferred monomers F) are ethene, propene, butene, isobutene, diisobutene, isoprene, 1,3-butadiene and mixtures thereof.

Monomer G)

Suitable esters of α,β-ethylenically unsaturated mono- and dicarboxylic acids with $C_1$-$C_{30}$-alkanols are, for example, methyl (meth)acrylate, methyl ethacrylate, ethyl (meth)acrylate, ethyl ethacrylate, n-propyl (meth)acrylate, isopropyl (meth)acrylate, n-butyl (meth)acrylate, tert-butyl (meth)acrylate, tert-butyl ethacrylate, n-pentyl (meth)acrylate, n-hexyl (meth)acrylate, n-heptyl (meth)acrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth)acrylate, palmityl (meth)acrylate, heptadecyl (meth)acrylate, nonadecyl (meth)acrylate, arachinyl (meth)acrylate, behenyl (meth)acrylate, lignoceryl (meth)acrylate, cerotinyl (meth)acrylate, melissyl (meth)acrylate, palmitoleyl (meth)acrylate, oleyl (meth)acrylate, linoleyl (meth)acrylate, linolenyl (meth)acrylate, stearyl (meth)acrylate, lauryl (meth)acrylate and mixtures thereof.

Monomer H)

The cationogenic and/or cationic groups of component H) are preferably nitrogen-containing groups such as primary, secondary and tertiary amino groups, and quaternary ammonium groups. Preferably, the nitrogen-containing groups are tertiary amino groups or quaternary ammonium groups. Charged cationic groups can be produced from the amine nitrogens either by protonation or by quaternization with acids or alkylating agents. Examples of, these include carboxylic acids such as lactic acid, or mineral acids such as phosphoric acid, sulphuric acid and hydrochloric acid, and examples of alkylating agents include $C_1$-$C_4$-alkyl halides or sulfates, such as ethyl chloride, ethyl bromide, methyl chloride, methyl bromide, dimethyl sulfate and diethyl sulfate. A protonation or quaternization may generally either precede or follow the polymerization.

Preferably, component H) is selected from esters of α,β-ethylenically unsaturated mono- and dicarboxylic acids with amino alcohols which may be mono- or dialkylated on the amine nitrogen, amides of α,β-ethylenically unsaturated mono- and dicarboxylic acids with diamines having at least one primary or secondary amino group, N,N-diallylamine, N,N-diallyl-N-alkylamines and derivatives thereof, vinyl- and allyl-substituted nitrogen heterocycles, vinyl- and allyl-substituted heteroaromatic compounds, and mixtures thereof.

Preferred monomers H) are the esters of α,β-ethylenically unsaturated mono- and dicarboxylic acids with amino alcohols. Preferred amino alcohols are $C_2$-$C_{12}$ amino alcohols with $C_1$-$C_8$ mono- or dialkylation on the amine nitrogen. Suitable acid components of these esters are, for example, acrylic acid, methacrylic acid, fumaric acid, maleic acid, itaconic acid, crotonic acid, maleic anhydride, monobutyl maleate and mixtures thereof. The acid components used are preferably acrylic acid, methacrylic acid and mixtures thereof.

Preferred monomers H) are N-methylaminoethyl (meth)acrylate, N-ethylaminoethyl (meth)acrylate, N-(n-propyl)aminoethyl (meth)acrylate, N-(tert-butyl)aminoethyl (meth)acrylate, N,N-dimethylaminomethyl (meth)acrylate, N,N-dimethylaminoethyl (meth)acrylate, N,N-diethylaminomethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate.

Suitable monomers H) are additionally the amides of the aforementioned α,β-ethylenically unsaturated mono- and dicarboxylic acids with diamines having at least one primary or secondary amino group. Preference is given to diamines having one tertiary amino group and one primary or secondary amino group.

Examples of preferred monomers H) are N-[tert-butylaminoethyl](meth)acrylamide, N-[2-(dimethylamino)ethyl] acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide.

In a suitable embodiment, component H) comprises, as vinyl-substituted heteroaromatic compound, at least one N-vinylimidazole compound. In a specific embodiment, component H) is selected from N-vinylimidazole compounds and mixtures comprising at least one N-vinylimidazole compound.

Suitable N-vinylimidazole compounds are compounds of the formula (III)

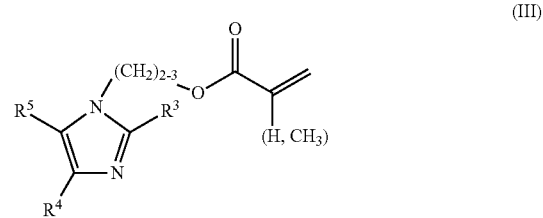

(III)

in which $R^3$ to $R^5$ are each independently hydrogen, $C_1$-$C_4$-alkyl or phenyl. Preferably, $R^1$ to $R^3$ are hydrogen.

Additionally suitable are N-vinylimidazole compounds of the general formula (IV)

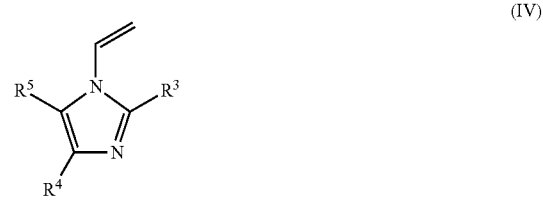

(IV)

in which $R^3$ to $R^5$ are each independently hydrogen, $C_1$-$C_4$-alkyl or phenyl.

Examples of compounds of the general formula (IV) are given in the table below:

TABLE

| $R^3$ | $R^4$ | $R^5$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Preferred monomers H) are 1-vinylimidazole (N-vinylimidazole) and mixtures comprising N-vinylimidazole.

Suitable monomers H) are also the compounds obtainable by protonating or quaternizing the aforementioned N-vinylimidazole compounds. Examples of such charged monomers H) are quaternized vinylimidazoles, in particular 3-methyl-1-vinylimidazolium chloride, methosulfate and ethosulfate. Suitable acids and alkylating agents are those listed above. Preference is given to a protonation or quaternization after the polymerization.

Suitable monomers H) are additionally vinyl- and allyl-substituted nitrogen heterocycles other than vinylimidazoles, such as 2- and 4-vinylpyridine, 2- and 4-allylpyridine, and the salts thereof.

Monomer I)

Suitable esters of vinyl alcohol with $C_1$-$C_{30}$-monocarboxylic acids are, for example, methyl vinyl ester, ethyl vinyl ester, n-propyl vinyl ester, isopropyl vinyl ester, n-butyl vinyl ester,
tert-butyl vinyl ester, n-pentyl vinyl ester, n-hexyl vinyl ester, n-heptyl vinyl ester, n-octyl vinyl ester, 1,1,3,3-tetramethylbutyl vinyl ester, ethylhexyl vinyl ester, n-nonyl vinyl ester, n-decyl vinyl ester, n-undecyl vinyl ester, tridecyl vinyl ester, myristyl vinyl ester, pentadecyl vinyl ester, palmityl vinyl ester, heptadecyl vinyl ester, octadecyl vinyl ester, nonadecyl vinyl ester, arachyl vinyl ester, behenyl vinyl ester, lignoceryl vinyl ester, cerotyl vinyl ester, melissyl vinyl ester, palmitoleyl vinyl ester, oleyl vinyl ester, linoleyl vinyl ester, linolenyl vinyl ester, stearyl vinyl ester, lauryl vinyl ester and mixtures thereof.

Monomer K

Suitable monomers containing amide groups K) are compounds of the general formula (V)

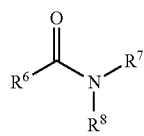

(V)

where
one of the $R^6$ to $R^8$ radicals is a group of the formula $CH_2=CR^9$— where $R^9$=H or $C_1$-$C_4$-alkyl and the other $R^6$ to $R^8$ radicals are each independently H, alkyl, cycloalkyl, heterocycloalkyl, aryl or hetaryl,
where $R^6$ and $R^7$ together with the amide group to which they are bonded may also be a lactam having 5 to 8 ring atoms,
where $R^7$ and $R^8$ together with the nitrogen atom to which they are bonded may also be a five- to seven-membered heterocycle.

Preferably, the compounds of component K) are selected from primary amides of α,β-ethylenically unsaturated monocarboxylic acids, N-vinylamides of saturated monocarboxylic acids, N-vinyllactams, N-alkyl- and N,N-dialkylamides of α,β-ethylenically unsaturated monocarboxylic acids and mixtures thereof.

Preferred monomers K) are N-vinyllactams and derivatives thereof which may have, for example, one or more $C_1$-$C_6$-alkyl substituents such as methyl, ethyl, n-propyl, isopropyl, n-butyl, sec-butyl, tert-butyl, etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam, etc.

Particular preference is given to using N-vinylpyrrolidone and/or N-vinylcaprolactam.

Suitable monomers K) are additionally acrylamide and methacrylamide,

Suitable N-alkyl- and N,N-dialkylamides of α,β-ethylenically unsaturated monocarboxylic acids are, for example, methyl(meth)acrylamide, methylethacrylamide, ethyl(meth)acrylamide, ethylethacrylamide, n-propyl(meth)acrylamide, isopropyl(meth)acrylamide, n-butyl(meth)acrylamide, tert-butyl(meth)acrylamide, tert-butylethacrylamide, n-pentyl(meth)acrylamide, n-hexyl(meth)acrylamide, n-heptyl(meth)acrylamide, n-octyl(meth)acrylamide, 1,1,3,3-tetramethylbutyl(meth)acrylamide, ethylhexyl(meth)acrylamide, n-nonyl(meth)acrylamide, n-decyl(meth)acrylamide, n-undecyl(meth)acrylamide, tridecyl(meth)acrylamide, myristyl(meth)acrylamide, pentadecyl(meth)acrylamide, palmityl(meth)acrylamide, heptadecyl(meth)acrylamide, nonadecyl(meth)acrylamide, arachinyl(meth)acrylamide, behenyl(meth)acrylamide, lignoceryl(meth)acrylamide, cerotyl(meth)acrylamide, melissyl(meth)acrylamide, palmitoleyl(meth)acrylamide, oleyl(meth)acrylamide, linoleyl(meth)acrylamide, linolenyl(meth)acrylamide, stearyl(meth)acrylamide, lauryl(meth)acrylamide, N-methyl-N-(n-octyl)(meth)acrylamide, N,N-di-(n-octyl)(meth)acrylamide and mixtures thereof.

Open-chain N-vinylamide compounds suitable as monomers K) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof. Preference is given to using N-vinylformamide.

Monomer L)

Suitable esters of α,β-ethylenically unsaturated mono- and dicarboxylic acids with $C_2$-$C_{30}$-alkanediols are 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, etc.

Suitable amides of α,β-ethylenically unsaturated mono- and dicarboxylic acids with $C_2$-$C_{30}$-amino alcohols having a primary or secondary amino group are 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Monomer M)

Suitable α,β-ethylenically unsaturated nitriles are acrylonitrile or methacrylonitrile.

Monomer N)

Suitable vinyl halides and vinylidene halides are vinyl chloride, vinylidene chloride, vinyl fluoride, vinylidene fluoride and mixtures thereof.

Monomer O)

Suitable monomers O) having urea groups are N-vinylurea, N-allylurea or derivatives of imidazolidin-2-one. These comprise N-vinyl- and N-allylimidazolidin-2-one, N-vinyloxyethylimidazolidin-2-one, N-(2-(meth)acrylamidoethyl)imidazolidin-2-one, N-(2-(meth)acryloyloxyethyl)imidazolidin-2-one (i.e. 2-ureido(meth)acrylate), N42-((meth)acryloyloxyacetamido)ethyllimidazolidin-2-one, etc.

Polyether Component PE)

Suitable polyether components PE) are polyetherols having a number-average molecular weight of at least 200 g/mol and the mono- and di($C_1$-$C_6$-alkyl ethers) thereof.

Suitable polyetherols and the mono- and di($C_1$-$C_6$-alkyl ethers) thereof may be linear or branched, preferably linear. Suitable polyetherols and the mono- and di($C_1$-$C_6$-alkyl ethers) thereof generally have a number-average molecular weight in the range from about 200 to 100 000, preferably 300 to 50 000, more preferably 500 to 40 000. Suitable polyetherols are, for example, water-soluble or water-dispersible nonionic polymers having repeat alkylene oxide units. Preferably, the proportion of repeat alkylene oxide units is at least 30% by weight, based on the total weight of the compound. Suitable polyetherols are polyalkylene glycols, such as polyethylene, glycols, polypropylene glycols, polytetrahydrofurans and alkylene oxide copolymers. Suitable alkylene oxides for preparation of alkylene oxide copolymers are, for example, ethylene oxide, propylene oxide, epichlorohydrin, 1,2- and 2,3-butylene oxide. Suitable examples are copolymers of ethylene oxide and propylene oxide, copolymers of ethylene oxide and butylene oxide, and copolymers of ethylene oxide, propylene oxide and at least one butylene oxide. The alkylene oxide copolymers may comprise the copolymerized alkylene oxide units in random distribution or in the form of blocks. Preferably, the proportion of repeat units derived from ethylene oxide in the ethylene oxide/propylene oxide copolymers is 40% to 99% by weight. Particularly preferred polyether components PE) are ethylene oxide homopolymers and ethylene oxide/propylene oxide copolymers.

Suitable polyether components PE) are additionally the mono- and di($C_1$-$C_2$-alkyl ethers) of the above-described polyetherols. Preference is given to polyalkylene glycol monomethyl ethers and polyalkylene glycol dimethyl ethers.

Suitable polyether components PE) are additionally surfactants containing polyether groups. In general, nonionic and ionic surfactants having at least one nonpolar group and at least one polar group and comprising a polyether group are suitable.

The surfactants containing polyether groups PE) are preferably selected from alkyl polyoxyalkylene ethers, aryl polyoxyalkylene ethers, alkylaryl polyoxyalkylene ethers, alkoxylated animal and/or vegetable fats and/or oils, fatty amine alkoxylates, fatty acid amide alkoxylates, fatty acid diethanolamide alkoxylates, polyoxyethylene sorbitan fatty acid esters, alkyl polyether sulfates, aryl polyether sulfates, alkylaryl polyether sulfates, alkyl polyether sulfonates, aryl polyether sulfonates, alkylaryl polyether sulfonates, alkyl polyether phosphates, aryl polyether phosphates, alkylaryl polyether phosphates, glyceryl ether sulfonates, glyceryl ether sulfates, monoglyceride (ether) sulfates, fatty acid amide ether sulfates, polyoxyalkylene sorbitan fatty acid esters and mixtures thereof.

The preferred nonionic surfactants containing polyether groups PE) are, for example:

alkyl polyoxyalkylene ethers which derive from low molecular weight $C_3$-$C_6$ alcohols or from $C_7$-$C_{30}$ fatty alcohols. The ether component here may be derived from ethylene oxide units, propylene oxide units, 1,2-butylene oxide units, 1,4-butylene oxide units and random copolymers and block copolymers thereof.

Suitable nonionic surfactants comprise, inter alia, surfactants of the general formula (VI)

$$R^{10}\text{—O—}(CH_2CH_2O)_x\text{—}(CHR^{11}CH_2O)_y\text{—}R^{12} \quad (VI)$$

in which $R^{10}$ is a linear or branched alkyl radical having 6 to 22 carbon atoms, $R^{11}$ and $R^{12}$ are each independently hydrogen or a linear or branched alkyl radical having 1 to 10 carbon atoms or H, where $R^{12}$ is preferably methyl, and x and y are each independently 0 to 300. Preferably, x=1 to 100 and y=0 to 30.

These especially also include fatty alcohol alkoxylates and oxo alcohol alkoxylates, such as isotridecyl alcohol polyoxyethylene ethers and oleyl alcohol polyoxyethylene ethers.

surfactants containing hydroxyl groups of the general formula (VII)

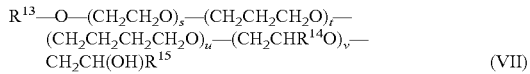

$$R^{13}\text{—O—}(CH_2CH_2O)_s\text{—}(CH_2CH_2CH_2O)_t\text{—}(CH_2CH_2CH_2CH_2O)_u\text{—}(CH_2CHR^{14}O)_v\text{—}CH_2CH(OH)R^{15} \quad (VII)$$

where the sequence of the alkylene oxide units in the compounds of the formula (VII) is arbitrary, s, t, u and v are each independently an integer from 0 to 500, where the sum of s, t, u and v is >0, $R^{13}$ and $R^{15}$ are each independently a straight-chain or branched saturated $C_1$-$C_{40}$-alkyl radical or a mono- or polyunsaturated $C_2$-$C_{40}$-alkenyl radical, and $R^{14}$ is selected from methyl, ethyl, n-propyl, isopropyl and n-butyl.

In the compounds of the general formula (VII), the sum of s, t, u and v is preferably a value of 10 to 300, more preferably of 15 to 200 and especially of 20 to 150.

Preferably, t and u are each 0. In that case, the sum of s and v is preferably a value of 10 to 300, more preferably of 15 to 200 and especially of 20 to 150.

In the compounds of the general formula (VII), $R^{13}$ and $R^{15}$ are preferably each independently a straight-chain or branched saturated $C_2$-$C_{30}$-alkyl radical. At the same time, $R^{13}$ and $R^{15}$ may also be mixtures of different alkyl radicals.

In the compounds of the general formula (VII), $R^{14}$ is preferably methyl or ethyl, especially methyl.

A preferred execution is surfactants containing hydroxyl groups of the general formula (VII.1)

$$R^{13}\text{—O—}(CH_2CH_2O)_s\text{—}(CH_2CH(CH_3)O)_v\text{—}CH_2CH(OH)R^{15} \quad (VII.1)$$

where the sequence of the —($CH_2CH_2O$)— and the ($CH_2CH(CH_3)O$)— units is arbitrary, s and v are each independently an integer from 0 to 500, where the sum of s and v is >0, and $R^{13}$ and $R^{15}$ are each independently a straight-chain saturated $C_1$-$C_{30}$-alkyl radical or a branched saturated $C_2$-$C_{30}$-alkyl radical or a mono- or polyunsaturated $C_2$-$C_{30}$-alkenyl radical.

In the compounds of the general formula (VII.1), the sum of s and v is preferably a value of 10 to 300, more preferably of 15 to 200 and especially of 20 to 150.

The group of these nonionic surfactants includes, for example, hydroxy mixed ethers of the general formula ($C_{6-22}$-alkyl)-$CH(OH)CH_2O$-$(EO)_{20-120}$—($C_{2-26}$-alkyl).

alcohol polyoxyalkylene esters of the general formula (VIII)

$$R^{16}-O-(CH_2CH_2O)_p-(CH_2CHR^{17}O)_q-C(=O) \atop R^{18} \quad (VIII)$$

where the sequence of the alkylene oxide units in the compounds of the formula (VIII) is arbitrary, p and q are each independently an integer from 0 to 500, where the sum of p and q is >0, $R^{16}$ and $R^{18}$ are each independently a straight-chain or branched saturated $C_1$-$C_{40}$-alkyl radical or a mono- or polyunsaturated $C_2$-$C_{40}$-alkenyl radical, and $R^{17}$ is selected from methyl, ethyl, n-propyl, isopropyl and n-butyl.

In the compounds of the general formula (VIII), the sum of p and q is preferably a value of 10 to 300, more preferably of 15 to 200 and especially of 20 to 150.

In the compounds of the general formula (VIII), $R^{16}$ and $R^{18}$ are preferably each independently a straight-chain or branched saturated $C_4$-$C_{30}$-alkyl radical. At the same time, $R^{16}$ and $R^{18}$ may also be mixtures of different alkyl radicals.

In the compounds of the general formula (VIII), $R^{17}$ is preferably methyl or ethyl, especially methyl.

These include, for example, lauryl alcohol polyoxyethylene acetate.

alkylaryl alcohol polyoxyethylene ethers, for example octylphenol polyoxyethylene ethers, alkoxylated animal and/or vegetable fats and/or oils, for example corn oil ethoxylates, castor oil ethoxylates, tallow fat ethoxylates, alkylphenol alkoxylates, for example ethoxylated isooctyl-, octyl- or nonylphenol, tributylphenol polyoxyethylene ether, fatty amine alkoxylates, fatty acid amide and fatty acid diethanolamide alkoxylates, especially ethoxylates thereof, polyoxyalkylene sorbitan fatty acid esters.

One example of an alkyl polyether sulfate is sodium dodecyl poly(oxyethylene) sulfate (sodium lauryl ether sulfate, SLES). A preferred commercially available modified fatty alcohol polyglycol ether is a polyethylene oxide $C_xH_{2x+1}/C_yH_{2y+1}$-terminated at either end and having a free OH group and x, y=6-14.

Solvent S)

The free-radical polymerization in step b) can be effected in the presence of a solvent S) selected from water, $C_1$-$C_6$-alkanols, polyols other than PE), the mono- and dialkyl ethers thereof, and mixtures thereof. Suitable polyols and the mono- and dialkyl ethers thereof also comprise alkylene glycol mono($C_1$-$C_4$-alkyl ethers), alkylene glycol di($C_1$-$C_4$-alkyl) ethers, oligoalkylene glycols having a number-average molecular weight of less than 200 g/mol and the mono($C_1$-$C_4$-alkyl ethers) and di($C_1$-$C_4$-alkyl ethers) thereof.

The solvent S) is preferably selected from water, methanol, ethanol, n-propanol, isopropanol, n-butanol, ethylene glycol, ethylene glycol mono($C_1$-$C_4$-alkyl ethers), ethylene glycol di($C_1$-$C_4$-alkyl) ethers, 1,2-propylene glycol, 1,2-propylene glycol mono($C_1$-$C_4$-alkyl ethers), 1,2-propylene glycol di($C_1$-$C_4$-alkyl ethers), glycerol, polyglycerols, oligoalkylene glycols having a number-average molecular weight of less than 200 g/mol and mixtures thereof.

Suitable oligoethylene glycols are commercially available under the CTFA designations PEG-6, PEG-8, PEG-12, PEG-6-32, PEG-20, PEG-150, PEG-7M, PEG-12M and PEG-115M. These especially include the Pluriol E® products from BASF SE. Suitable alkyl polyalkylene glycols are the corresponding Pluriol A . . . E® products from BASF SE.

The solvent S) is more preferably selected from water, ethanol, n-propanol, isopropanol, ethylene glycol, diethylene glycol, 1,2-propylene glycol, 1,2-dipropylene glycol and mixtures thereof.

In a specific embodiment, the solvent S) used is selected from water and a mixture of water and at least one solvent S) other than water, selected from ethanol, n-propanol, isopropanol, ethylene glycol, diethylene glycol, 1,2-propylene glycol, 1,2-dipropylene glycol and mixtures thereof.

In a specific embodiment, the free-radical polymerization in step c) is effected in the presence of a solvent S) consisting to an extent of at least 50% by weight, preferably to an extent of at least 75% by weight, especially to an extent of at least 90% by weight, based on the total weight of the solvent S), of water. More particularly, the free-radical polymerization in step c) is effected in the presence of a solvent S) consisting entirely of water, Preparation of the Inventive Polymer Compositions The preparation of the inventive polymer compositions comprises a free-radical polymerization of the monomer composition M) in the presence of at least one polyether component PE). It is preferably conducted in a feed method. This generally involves metering at least the monomers in liquid form into the reaction mixture. Monomers liquid under the metering conditions can be fed into the reaction mixture without addition of a solvent S); otherwise, the monomers are used as a solution in a suitable solvent S).

Preferably, the free-radical polymerization in step b) is effected in feed mode, in which case feeds comprising at least one α,β-ethylenically unsaturated carboxylic acid do not comprise any solvent S).

The metering rates of the monomer feed(s) and of any further feeds (initiator, chain transfer agent, etc.) are preferably chosen such that the polymerization is maintained with the desired conversion rate. The individual feeds can be added continuously, periodically, with constant or varying metering rate, and essentially simultaneously or offset in time. Preferably, all feeds are added to the reaction mixture continuously.

The weight ratio of the monomer mixture M) to the component PE) is preferably in the range from 1:10 to 10:1.

If the polymer composition is prepared using a solvent S), the weight ratio of the component PE) to the component S) is preferably in the range from 0.3:1 to 5:1, more preferably in the range from 0.5:1 to 3:1.

Preferably, the free-radical polymerization in step b) is effected at a temperature in the range from 20 to 95° C., more preferably from 30 to 90° C., especially from 40 to 80° C.

Preferably, the free-radical polymerization comprises, in step b) of the process according to the invention, b1) providing an initial charge comprising at least a portion of the polyether component PE), optionally at least a portion of the chain transfer agent CTA) and, if the polymerization is effected in the presence of a solvent S), optionally at least a portion of S);

b2) adding the monomer composition M) in one or more feed(s) and adding a feed comprising the free-radical initiator FRI), dissolved in a portion of the at least one polyether component PE) and/or of the solvent S), and optionally adding a feed comprising the amount of the chain transfer agent CTA) which is not used in the initial charge, b3) optionally continuing polymerization of the reaction mixture obtained in step b2).

Typically, the initial charge is heated to the polymerization temperature before adding the feeds while stirring.

Preferably, the individual reactants are added simultaneously in separate feeds, in which case the flow rates of the feeds are generally kept very substantially constant over the period of addition.

The addition of the feeds in step b2) is effected over a period which is advantageously selected such that the heat of reaction which arises in the exothermic polymerization can be removed without any great technical complexity, for example without the use of a reflux condenser. Typically, the feeds are added over a period of 1 to 10 hours. Preferably, the feeds are added over a period of 2 to 8 hours, more preferably over 3 to 5 hours.

During the free-radical polymerization, the solvent optionally used and/or any condensation products formed are generally not removed. In other words, during the polymerization, there is typically only minor mass transfer with the environment within the realm of technical possibility, if any.

The polymerization can generally be effected at ambient pressure or reduced or elevated pressure. Preferably, the polymerization is performed at ambient pressure.

The polymerization is generally effected at constant temperature, but can also be varied during the polymerization if required. Preferably, the polymerization temperature is kept very substantially constant over the entire reaction period, i.e. of steps b2) and b3). According to which feedstocks are used in the process according to the invention, the polymerization temperature varies typically within the range from 20 to 95° C. Preferably, the polymerization temperature varies within the range from 30 to 90° C. and especially within the range from 40 to 80° C. If the polymerization is not conducted under elevated pressure and at least one optional solvent S) has been added to the reaction mixture, the solvent or solvent mixture determines the maximum reaction temperature via the corresponding boiling temperatures.

The polymerization can be effected in the absence or presence of an inert gas. Typically, the polymerization is performed in the presence of an inert gas. Inert gas is generally understood to mean a gas which, under the given reaction conditions, does not enter into any reaction with the reactants, reagents or solvents involved in the reaction, or the products formed.

If the polymerization is performed in the presence of a solvent, this is selected from the above-described solvents S).

To prepare the polymers, the monomers can be polymerized with the aid of free radical-forming initiators, also referred to hereinafter as free-radical initiators or initiators. Useful free-radical initiators (initiators) for the free-radical polymerization in principle include all the free-radical initiators that are essentially soluble in the reaction medium as exists at the time of addition thereof and have sufficient activity at the given reaction temperatures to initiate the polymerization. It is possible to use a single free-radical initiator or a combination of at least two free-radical initiators in the process according to the invention. In the latter case, the at least two free-radical initiators can be used in a mixture or preferably separately, simultaneously or successively, for example at different times in the course of the reaction.

Free-radical initiators used for the free-radical polymerization may be the peroxo and/or azo compounds customary for this purpose, for example alkali metal or ammonium peroxodisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxodicarbamate, bis(o-tolyl) peroxide, didecanoyl peroxide, dioctanoyl peroxide, tert-butyl peroctoate, dilauroyl peroxide, tert-butyl perisobutyrate, tert-butyl peracetate, di-tert-amyl peroxide, tert-butyl hydroperoxide, 2,2'-azobisisobutyronitrile, azobis(2-amidinopropane) dihydrochloride, azobis(2,4-dimethylvaleronitrile) or 2,2'-azobis (2-methylbutyronitrile).

Also suitable are initiator mixtures or redox initiator systems, for example
ascorbic acid/iron(II) sulfate/sodium peroxodisulfate,
tert-butyl hydroperoxide/sodium disulfite,
tert-butyl hydroperoxide/sodium hydroxymethanesulfinate,
$H_2O_2/Cu^I$.

In the process according to the invention, the amount of initiator system (initiator) used varies within the range from 0.01% to 10% by weight, preferably within the range from 0.1% to 5% by weight, more preferably within the range from 0.2% to 2% by weight and especially within the range from 0.3% to 1.5% by weight, In the process according to the invention, the free-radical initiator is generally provided as a solution in a solvent comprising at least one of the aforementioned solvents S).

The amount of chain transfer agent which is typically used in the process according to the invention is 1 to 40 pphm ("parts per hundred of monomer", i.e. parts by weight based on one hundred parts by weight of monomer composition). Preferably, the amount of chain transfer agent used in the process according to the invention is within the range from 3 to 30 pphm, more preferably in the range from 5 to 25 pphm.

Typically, the chain transfer agent is added continuously to the polymerization mixture in step b2) entirely via one of the feeds. However, it is also possible to add the chain transfer agent either entirely to the initial charge, i.e. before the actual polymerization, or only a portion of the chain transfer agent is included in the initial charge and the rest is added continuously to the polymerization mixture in step b) via one of the feeds. The chain transfer agent can be added in each case without or with solvent S).

The amount of the chain transfer agent and the way in which it is added to the reaction mixture have a strong influence on the mean molecular weight of the polymer composition. When less chain transfer agent is used and/or when the addition is effected predominantly prior to the polymerization, this generally leads to higher mean molecular weights of the polymer formed. If, in contrast, greater amounts of chain transfer agent are used and/or the addition of the chain transfer agent takes place for the most part during the polymerization (step b2)), this generally leads to a lower mean molecular weight.

1st Variant: Preparation of a Polymer Composition for Films

The process according to the invention serves, in a first preferred embodiment, for preparation of a polymer composition suitable for provision of films, especially of transparent films.

In the 1st variant, the amount of polyether component PE) in the initial charge (step b1)) is preferably 30% to 100% by weight, more preferably 65% to 100% by weight and especially 80% to 100% by weight, based on the total weight of the polyether component PE) used for polymerization.

In the 1st variant, the ratio of the polyether component PE) used to prepare the polymer composition to the monomer composition M) used is typically in the range from 1.0:0.8 to 1.0:5, preferably in the range from 1.0:1.0 to 1.0:2.5.

In this embodiment, the content of solvent in the first fraction is typically not more than 70% by weight, based on the total weight of the feedstocks present in the first fraction. Preferably, the content of solvent in the first fraction is not more than 40% by weight, especially not more than 35% by weight, based on the total weight of the feedstocks present in the first fraction. The amount of solvent changes generally only by a few percent by weight over the entire course of the process. Typically, solvents S) having a boiling point at standard pressure (1 bar) of below 240° C. are used. In general, solvents S used in this first preferred embodiment are water, ethanol, n-propanol, isopropanol, n-butanol, ethylene glycol, ethylene glycol mono($C_1$-$C_4$-alkyl ethers), ethylene glycol di($C_1$-$C_4$-alkyl ethers), 1,2-propylene glycol, 1,2-propylene glycol mono($C_1$-$C_4$-alkyl ethers), 1,2-propylene glycol di($C_1$-$C_4$-alkyl ethers), dipropylene glycols or mixtures thereof. Solvents S) used with preference in this first preferred embodiment are water, ethanol, n-propanol, isopropanol, n-butanol or mixtures thereof.

In a specific variant of this embodiment, the initial charge does not comprise any solvent. This is only added in step b2) via at least one of the feeds. In a very specific variant of this embodiment, no solvent is initially charged and no solvent is added over the entire course of the process.

In this first preferred embodiment, the polymer compositions obtained after the polymerization has ended (step b3)) are transferred into a suitable vessel and optionally cooled directly to ambient temperature (20° C.).

The polymer compositions obtained in this way have a firm consistency and are transparent, meaning that they are transparent and have a transparency ($T_L$) of at least 85%, especially of at least 90%, based on the transparency of water. They are suitable for production of films, for example as a sheath for a liquid dishwashing, washing or cleaning composition. The production of films and of sheaths based thereon is described in detail hereinafter.

2nd Variant: Preparation of a Polymer Composition for Coatings

The process according to the invention serves, in a second preferred embodiment, for preparation of a polymer composition suitable for provision of solid coatings on a substrate.

In the 2nd variant, the amount of polyether component PE) in the initial charge (step b1)) is preferably 30% to 100% by weight, more preferably 65% to 100% by weight and especially 80% to 100% by weight, based on the total weight of the polyether component PE) used for polymerization.

In the 2nd variant, the ratio of the polyether component PE) used to prepare the polymer composition to the monomer composition M) used is typically in the range from 1.0:0.8 to 1.0:5, preferably in the range from 1.0:1.0 to 1.0:2.5.

In this embodiment, the content of solvent in the first fraction is typically not more than 70% by weight, based on the total weight of the feedstocks present in the first fraction. Preferably, the content of solvent in the first fraction is not more than 40% by weight, especially not more than 35% by weight, based on the total weight of the feedstocks present in the first fraction. The amount of solvent changes generally only by a few percent by weight over the entire course of the process. Typically, solvents S) having a boiling point at standard pressure (1 bar) of below 240° C. are used. In general, solvents S used in this first preferred embodiment are water, ethanol, n-propanol, isopropanol, n-butanol, ethylene glycol, ethylene glycol mono($C_1$-$C_4$-alkyl ethers), ethylene glycol di($C_1$-$C_4$-alkyl ethers), 1,2-propylene glycol, 1,2-propylene glycol mono($C_1$-$C_4$-alkyl ethers), 1,2-propylene glycol di($C_1$-$C_4$-alkyl ethers), dipropylene glycols or mixtures thereof. Solvents S) used with preference in this first preferred embodiment are water, ethanol, n-propanol, isopropanol, n-butanol or mixtures thereof.

In a specific variant of this embodiment, the initial charge does not comprise any solvent. This is only added in step b2) via at least one of the feeds. In a very specific variant of this embodiment, no solvent is initially charged and no solvent is added over the entire course of the process.

In this first preferred embodiment, the polymer compositions obtained after the polymerization has ended (step b3)) are transferred into a suitable vessel and optionally cooled directly to ambient temperature (20° C.).

The polymer compositions obtained in this way are suitable for production of solid coatings on a substrate, for example of a dishwashing, washing or cleaning composition tablet. The production of such coatings is described in detail hereinafter.

3rd Variant: Preparation of Solid Compositions

The process according to the invention serves, in a third preferred embodiment, for provision of solid, especially particulate, polymer compositions.

In this third preferred embodiment of the process according to the invention, the amount of polyether component PE) in the initial charge (step b1)) is typically 40% to 100% by weight, preferably 90% to 100% by weight and especially 95% to 100% by weight, based on the total weight of the polyether component PE) used for polymerization. Specifically, the polyether component PE) is initially charged in full before the polymerization.

In this third preferred embodiment, the content of solvent in the initial charge is 25% to 70% by weight, based on the total weight of all the feedstocks present in the first fraction. Preferably, the content of solvent in the first fraction is 30% to 65% by weight, especially 35% to 60% by weight, based on the total weight of all the feedstocks present in the first fraction. Solvents S) used are preferably water or $C_1$-$C_8$-alkanols, more preferably water, methanol, ethanol, n-propanol, isopropanol, n-butanol, especially water or isopropanol and mixtures thereof.

The ratio of the polyether component PE) used to prepare the polymer composition to the monomer composition M) used, in this second embodiment, is typically in the range from 1:1 to 1:10.

In this third preferred embodiment, the polymer compositions obtained after the polymerization has ended (step b3)) are transferred into a suitable vessel and optionally cooled directly to ambient temperature (20° C.). In general, the polymer compositions obtained in the second preferred embodiment are immediately sent to a drying and/or comminution process, as described below.

The polymer compositions prepared by the process according to the invention can, after the polymerization, be subjected to further reprocessing steps. These include, for example, melting processes, shaping processes, drying processes, comminution processes, purifying processes or combinations thereof.

In a suitable embodiment, the reaction product obtained in step b) is subjected to shaping. Preferably, this gives a particulate product. The polymer composition can be provided in a particle size ranging from pulverulent particles to pellet size. A preferred embodiment is a particulate polymer composition having a particle size within a range from about 100 μm to 10 mm.

Preferably, the shaping of the prepolymer comprises a plasticization, for example by extrusion, and a pelletizing operation, roll shaping operation and/or grinding operation. Suitable processes for pelletization, roll shaping and grinding of polymers are known to those skilled in the art. In a suitable execution, the polymer composition is first formed into one or more strands for shaping. For this purpose, apparatuses known to those skilled in the art can be used. Suitable apparatuses are, for example, perforated plates, nozzles or die plates. In a suitable embodiment, the polymer composition formed to strands is subjected in free-flowing form to a comminution to give polymer particles. In an alternative embodiment, the polymer composition formed to strands is solidified and than subjected to a comminution to give polymer particles. Suitable mills for grinding the prepolymers are, for example, hammer mills, roll mills, ball mills, etc.

In a first preferred reprocessing variant, the inventive transparent polymer compositions are first converted to a free-flowing state by heating. These compositions can then be subjected in a further step to a wide variety of different shaping processes, for example spreading on a solid carrier material to produce transparent films, or the casting of sheaths, sleeves or other hollow bodies suitable for filling. After shaping, the films or hollow bodies are typically dried at a temperature of 50 to 110° C. over a period of 12 to 72 hours.

In a second preferred reprocessing variant, the solvent optionally present in the inventive polymer compositions is distilled off under reduced pressure. The polymeric solid thus obtained is subsequently comminuted to give a pelletized material or converted to a powder by crushing. In this reprocessing variant, the inventive polymer compositions can also be processed directly after the polymerization and cooling to room temperature to give a pelletized material or powder, if the latter has a firm consistency. In general, the inventive polymer compositions of the second preferred embodiment of the process according to the invention are advantageously suitable for this reprocessing variant. They can generally be used to obtain firm, free-flowing powders and/or pellets.

None, some or all of the acid groups of the inventive polymer composition may be neutralized. Preferably, none or only some of the acid groups in the inventive polymer composition are neutralized.

Bases used for the neutralization may be alkali metal bases, such as sodium hydroxide solution, potassium hydroxide solution, sodium carbonate, sodium hydrogencarbonate, potassium carbonate or potassium hydrogencarbonate, and alkaline earth metal bases, such as calcium hydroxide, calcium oxide, magnesium hydroxide or magnesium carbonate, and ammonia or amines. Suitable amines are, for example, $C_1$-$C_6$-alkylamines, preferably n-propylamine and n-butylamine, dialkylamines, preferably diethylpropylamine and dipropylmethylamine, trialkylamines, preferably triethylamine and triisopropylamine. Preference is given to amino alcohols, for example trialkanolamines such as triethanolamine, alkyldialkanolamines such as methyl- or ethyldiethanolamine, and dialkylalkanolamines such as dimethylethanolamine, and also 2-amino-2-methyl-1-propanol. The neutralization of the acid groups can also be undertaken with the aid of mixtures of two or more bases. The base is more preferably selected from NaOH. KOH, 2-amino-2-methyl-1-propanol, triethylamine, diethylaminopropylamine, diethanolamine, triethanolamine, triisopropanolamine and mixtures thereof.

Characterization of the Polymer Composition

The inventive polymer composition preferably has a content of acid groups of more than 1 mmol/g, more preferably of more than 1.3 mmol/g auf. The inventive polymer composition preferably has a content of acid groups of not more than 15 mmol/g. The inventive polymer composition especially has a content of acid groups of 1.5 mmol/g to 15 mmol/g.

A polymer composition in the form of a solid substance preferably has a content of acid groups of 1.5 mmol/g to 15 mmol/g.

In a first preferred embodiment, up to 80 mol % of the acid groups, more preferably up to 70 mol % of the acid groups, especially up to 20 mol % of the acid groups, in the inventive polymer composition are in neutralized form.

In a second preferred embodiment, the acid groups of the inventive polymer composition are in non-neutralized form.

Preferably, the polymer composition has a solubility in water at 40° C. and a pH of 8 of at least 5 g/l.

The weight-average molecular weight M, of the inventive polymer composition, determined by means of gel permeation chromatography (GPC) using neutralized polyacrylic acid as polymer standard, is preferably 1000 to 150 000 daltons.

Surfactant-Containing Composition

The inventive polymer composition is particularly advantageously suitable for formulation of surfactant-containing compositions. More particularly, these are aqueous surfactant-containing compositions. The inventive polymer composition is notable for its good compatibility with a multitude of surfactants.

Surfactant-containing compositions comprising the inventive polymer composition preferably have a total surfactant content of 0.1% to 75% by weight, more preferably of 0.5% to 60% by weight, especially of 1% to 50% by weight, based on the total weight of the surfactant-containing composition.

Suitable additional surfactants are anionic surfactants, nonionic surfactants, cationic surfactants, amphoteric surfactants and mixtures thereof.

Typical examples of anionic surfactants are soaps, alkylsulfonates, alkylbenzenesulfonates, olefinsulfonates, methyl ester sulfonates, sulfo fatty acids, alkyl sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyl oligoglucoside sulfates, alkylglucose carboxylates, protein fatty acid condensates and alkyl (ether) phosphates.

Suitable soaps are, for example, alkali metal, alkaline earth metal and ammonium salts of fatty acids, such as potassium stearate.

Suitable olefinsulfonates are obtained, for example, through addition of $SO_3$ onto olefins of the formula $R^{15}$—CH=CH—$R^{16}$ and subsequent hydrolysis and neutralization, where $R^{15}$ and $R^{16}$ are each independently H or alkyl radicals having 1 to 20 carbon atoms, with the proviso that $R^{15}$ and $R^{16}$ together have at least 6 and preferably 8 to 20, especially 10 to 16, carbon atoms. With regard to preparation and use, reference may be made to the review article "J. Am. Oil. Chem. Soc.", 55, 70 (1978). The olefinsulfonates may be present as alkali metal, alkaline earth metal, ammonium, alkylammonium, alkanolammonium or glucammonium salts. Preferably, the olefinsulfonates are present as sodium salts. The hydrolyzed alpha-olefinsulfonation product, i.e. the alpha-olefinsulfonates, are composed of about 60% by weight of alkanesulfonates and about 40% by weight of hydroxyalkanesulfonates; for instance, 80% to 85% by weight of this is monosulfonates and 15% to 20% by weight is disulfonates, Preferred methyl ester sulfonates (MES) are obtained by sulfonation of the fatty acid methyl esters of vegetable or animal fats or oils. Preference is given to methyl ester sulfonates from vegetable fats and oils, e.g. from rapeseed oil, sunflower oil, soya oil, palm oil, coconut fat, etc.

Preferred alkyl sulfates are sulfates of fatty alcohols of the general formula $R^{17}$—O—$SO_3Y$ in which $R^{17}$ is a linear or branched, saturated or unsaturated hydrocarbon radical having 6 to 22 carbon atoms and Y is an alkali metal, the monovalent charge equivalent of an alkaline earth metal, ammonium, mono-, di-, tri- or tetraalkylammonium, alkanolammonium or glucammonium. Suitable fatty alcohol sulfates will preferably be obtained by sulfation of native fatty alcohols or synthetic oxo alcohols and subsequent neutralization. Typical examples of fatty alcohol sulfates are the sulfation products of caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoleyl alcohol, linolenyl alcohol, behenyl alcohol and eleostearyl alcohol, and also the salts and mixtures thereof. Preferred salts of the fatty alcohol sulfates are the sodium and potassium salts, especially the sodium salts. Preferred mixtures of the fatty alcohol sulfates are based on technical grade alcohol mixtures obtained, for example, in the high-pressure hydrogenation of technical grade methyl esters based on fats and oils or in the hydrogenation of aldehydes from the oxo process or in the dimerization of unsaturated fatty alcohols. For preparation of alkyl sulfates, preference is given to using fatty alcohols and fatty alcohol mixtures having 12 to 18 carbon atoms and especially 16 to 18 carbon atoms. Typical examples thereof are technical grade alcohol sulfates based on vegetable raw materials.

Preferred sarcosinates are sodium lauroyl sarcosinate or sodium stearoyl sarcosinate.

Preferred protein fatty acid condensates are wheat-based vegetable products.

Preferred alkyl phosphates are alkyl mono- and diphosphates.

Suitable acyl glutamates are compounds of the formula (I)

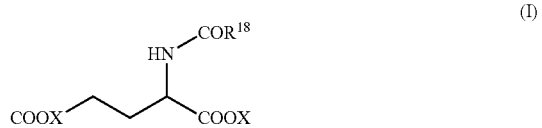

in which $COR^{18}$ is a linear or branched acyl radical having 6 to 22 carbon atoms and 0, 1, 2 or 3 double bonds and X is hydrogen, an alkali metal, the monovalent charge equivalent of an alkaline earth metal, ammonium, alkylammonium, alkanolammonium or glucammonium. Acyl glutamates are prepared, for example, by Schotten-Baumann acylation of glutamic acid with fatty acids, fatty acid esters or fatty acid halides. Acyl glutamates are commercially available, for example, from Clariant AG, Frankfurt, Germany, or Ajinomoto Co. Inc., Tokyo, Japan. An overview of the preparation and properties of the acyl glutamates can be found in M. Takehara et al. in J. Am, Oil Chem. Soc. 49 (1972) 143, Typical acyl glutamates suitable as component b) are preferably derived from fatty acids having 6 to 22 and particularly preferably 12 to 18 carbon atoms. In particular, the mono- or dialkali metal salts of the acyl glutamate are used. These include, for example (trade names of Ajinomoto, USA in brackets): sodium cocoylglutamate (Amisoft CS-11), disodium cocoylglutamate (Amisoft ECS-22SB), triethanolammonium cocoylglutamate (Amisoft CT-12), triethanolammonium lauroylglutamate (Amisoft LT-12), sodium myristoylglutamate (Amisoft MS-11), sodium stearoylglutamate (Amisoft HS-11 P) and mixtures thereof.

The additional nonionic surfactants include, for example:
glyceryl esters, for example glyceryl monostearate,
sugar surfactants, sorbitol esters, for example sorbitan fatty acid esters (sorbitan monooleate, sorbitan tristearate), polyoxyethylenesorbitan fatty acid esters, alkyl polyglycosides, N-alkylgluconamides,
alkyl methyl sulfoxides,
alkyldimethylphosphine oxides, for example tetradecyldimethylphosphine oxide.

Suitable amphoteric surfactants are, for example, alkyl betaines, alkylamidopropyl betaines, alkyl sulfobetaines, alkyl glycinates, alkyl carboxyglycinates, alkyl amphoacetates or amphopropionates, alkyl amphodiacetates or alkyl amphodipropionates. For example, it is possible to use cocodimethylsulfopropyl betaine, lauryl betaine, cocamidopropyl betaine, sodium cocamphopropionate or tetradecyldimethylamine oxide.

The cationic surfactants include, for example, quaternized ammonium compounds, especially alkyltrimethylammonium and dialkyldimethylammonium halides and alkylsulfates, and also pyridine and imidazoline derivatives, especially alkylpyridinium halides. For example, it is possible to use behenyl- or cetyltrimethylammonium chloride.

Washing Cleaning and Dishwashing Compositions

The inventive polymer composition is advantageously suitable for use in washing and cleaning compositions, in dishwashing compositions and in rinse aids.

Washing compositions in the context of the present invention are understood to mean those compositions which are used for cleaning flexible materials having high absorbency, for example materials having a textile character, whereas cleaning compositions in the context of the present invention are understood to mean those compositions which are used for cleaning materials having a closed surface, i.e. having a surface which has only few and small pores, if any, and consequently has zero or only low absorbency.

Examples of flexible materials having high absorbency are those which comprise or consist of natural, synthetic or semisynthetic fiber materials, and which accordingly generally have at least some textile character. The fibrous materials or materials consisting of fibers may in principle be present in any form which occurs in use or in manufacture and processing. For example, fibers may be present in unordered form in the form of staple or aggregate, in ordered form in the form of fibers, yarns, threads, or in the form of three-dimensional structures such as nonwovens, lodens or felt, wovens, knits, in all conceivable binding types. The fibers may be raw fibers or fibers in any desired stages of processing. Examples are natural protein or cellulose fibers, such as wool, silk, cotton, sisal, hemp or coconut fibers, or synthetic fibers, for example polyester, polyamide or polyacrylonitrile fibers.

Examples of materials having only few and small pores, if any, and having zero or only low absorbency are metal, glass, enamel or ceramic. Typical objects made of these materials are, for example, metallic sinks, cutlery, glass and porcelain dishware, bathtubs, washbasins, tiles, flags, cured synthetic resins, for example decorative melamine resin surfaces on kitchen furniture or painted metal surfaces, for example refrigerators and car bodies, printed circuit boards, microchips, sealed or painted woods, e.g. parquet or wall cladding, window frames, doors, plastics coverings such as floor coverings made of PVC or hard rubber, or rigid or flexible foams having substantially closed surfaces.

Examples of cleaning compositions comprising the inventive polymer composition comprise washing and cleaning compositions, dishwashing compositions such as manual dishwashing compositions or machine dishwashing compositions (=a dishwashing composition for machine dishwashers), metal degreasers, glass cleaners, floor cleaners, all-purpose cleaners, high-pressure cleaners, neutral cleaners, alkaline cleaners, acidic cleaners, spray degreasers, dairy cleaners, commercial kitchen cleaners, machinery cleaners in industry, especially the chemical industry, cleaners for carwashing and also domestic all-purpose cleaners.

A first embodiment is washing and cleaning and dishwashing compositions which comprise the inventive polymer composition and are solid at room temperature (20° C.). A second embodiment is washing and cleaning and dishwashing compositions which comprise a noninventive polymer composition in liquid or gel form at room temperature (20° C.) and which comprise an inventive polymer composition in the sheath or coating of the washing, cleaning or dishwashing composition or at least one of the components thereof. A more specific execution is washing and cleaning and dishwashing compositions comprising an inventive polymer composition in the sheath or coating, said sheath or coating additionally comprising at least one active ingredient. The at least one active ingredient is then released in a controlled manner in the course of the washing and cleaning or dishwashing operation.

The solid washing and cleaning compositions may be pulverulent or tableted products ("tabs"). In a specific execution, they are tableted products ("tabs"). In a first particularly preferred execution, they are then tableted washing compositions. In a further particularly preferred execution, they are then tableted dishwashing compositions, especially tableted machine dishwashing compositions.

Tableted dishwashing compositions may be simple tabs or else what are called "2 in 1", "3 in 1", "5 in 1" or "7 in 1" products (multifunctional products). Further details of these formulations can be found in Hermann G. Hauthal, G. Wagner (eds.), Reinigungs-und Pflegemittel im Haushalt [Domestic Cleaning and Care Products], Verlag für chemische Industrie, H. Ziolkowsky GmbH, Augsburg 2003, Kapitel 4.2, pages 161-184. "2 in 1" products comprise, as well as the customary constituents of machine dishwashing detergents, additionally a rinse aid. "3 in 1" products also comprise a water softener. "5 in 1" products generally also comprise a glass protector and a rinsing power enhancer. "7 in 1" products also comprise a stainless steel brightener and a deincrustation agent. In these tableted dishwashing compositions, the inventive polymer composition may be present in the rinse aid core, or it is present in solid form in the tableted dishwashing composition.

The inventive polymer composition is additionally suitable for production of a sheath comprising solid or liquid or gel-form washing, cleaning or dishwashing compositions or at least one of the components thereof. The inventive polymer composition is additionally suitable for production of a coating on a solid washing, cleaning or dishwashing composition or on at least one solid component thereof.

The inventive polymer composition has the particular feature of the excellent action as a cobuilder, surfactant or soil release polymer. When used in the rinse cycle of the machine dishwasher, it also acts as an incrustation inhibitor. The constituents of the polymer composition also support the cleaning performance of the overall formulation, by detaching and dispersing the soil, The inventive washing, cleaning and dishwashing composition preferably comprises the following constituents:
a) at least one inventive polymer composition;
b) at least one builder (also referred to as sequestrant, builder material, complexing agent, chelator, chelating agent or softener);
c) optionally at least one enzyme;
d) optionally at least one bleach; and
e) optionally at least one further additive, preferably selected from the following additives other than a): surfactants, bases, corrosion inhibitors, defoamers, dyes, fragrances, fillers, tableting aids, disintegrants, thickeners, solubilizers, organic solvents, electrolytes, pH modifiers, perfume carriers, fluorescers, hydrotropes, antiredeposition agents, optical brighteners, graying inhibitors, shrink inhibitors, crease inhibitors, dye transfer inhibitors, active antimicrobial ingredients, antioxidants, corrosion inhibitors, antistats, ironing aids, hydrophobizing and impregnating agents, swell and antislip agents, UV absorbers and water.

Washing and Cleaning Compositions

Preferably, the inventive washing and cleaning compositions comprise:
a) at least one inventive polymer composition: from 0.1% to 20% by weight;
b) at least one builder: from 5% to 80% by weight;
c) at least one enzyme: from 0% to 8% by weight;
d) at least one bleach: from 0% to 30% by weight; and
e) at least one further additive: from 0% to 50% by weight.

The percentages by weight are each based on the total weight of the washing and cleaning composition. The weights of a) to e) add up to 100% by weight.

More preferably, the inventive washing and cleaning composition comprises at least one enzyme.

More preferably, the abovementioned constituents are present in the inventive washing and cleaning composition in the following ratios:
a) at least one inventive polymer composition: from 0.1% to 10% by weight;
b) at least one builder: from 20% to 80% by weight;
c) at least one enzyme: from 0.1% to 6% by weight;
d) at least one bleach: from 0% to 30% by weight; and
e) at least one further additive: from 0% to 50% by weight.

The percentages by weight are each based on the total weight of the washing and cleaning composition. The weights of a) to e) add up to 100% by weight.

Even more preferably, the inventive washing and cleaning composition also comprises at least one bleach.

Even more preferably, the abovementioned constituents are present in the inventive washing and cleaning composition in the following ratios:
a) at least one inventive polymer composition: from 0.1% to 10% by weight;
b) at least one builder: from 20% to 80% by weight;
c) at least one enzyme; from 0.1% to 6% by weight;
d) at least one bleach: from 5% to 25% by weight; and
e) at least one further additive: from 0% to 50% by weight.

The percentages by weight are each based on the total weight of the washing and cleaning composition. The weights of a) to e) add up to 100% by weight.

With regard to suitable and preferred inventive polymer compositions, reference is made to the details above.

Dishwashing Compositions

The above-described inventive polymer compositions are particularly advantageously suitable for use in dishware cleaning compositions, especially for machine dishwashing processes (automatic dishwashing, ADW). The inventive polymer composition is effective both as a surfactant and as a cobuilder. Examples of inventive formulations comprising the polymer composition for dishwashing thus comprise machine dishwashing detergents, rinse aids and machine dishwashing detergents with rinse aid function. The formulations are present especially at room temperature (20° C.). Machine dishwashing processes in the domestic and commercial sector comprise a plurality of successive steps, the first comprising the mechanical removal of loosely adhering food residues, the second the actual cleaning operation with the aid of a machine dishwasher, and the third generally consisting of a rinsing step, which is followed by the drying of the cleaned dishware. These operations are conducted in more or less automated form, the central unit used being a machine dishwasher in which at least the cleaning step and generally also the subsequent rinsing step and/or the drying step are conducted.

In machine dishwashers for the domestic sector, the soiled dishware is generally cleaned in a single chamber, and the aforementioned treatment steps proceed successively in a controlled program. Fresh water passes through the softening unit to the pump well and is sprayed by means of moving spray arms over the ware to be rinsed. Water-insoluble substances rinsed off are filtered out in the pump well. In the second rinse cycle, a generally alkaline cleaning composition is added to the rinse water, heated to the set temperature and distributed over the ware to be rinsed. In the last rinse cycle, a rinse aid is added to the treatment liquid, which reduces the surface tension, as a result of which the treatment liquid runs more easily off the ware. After the last rinse cycle, the contents are dried. The components used in the rinse cycle, such as water treatment agents, cleaning compositions, rinse aids, etc., can be used either in the form of individual components or in multicomponent formulations. Multifunctional detergents of this kind comprise surfactants for rinsing and a polymer for water softening. In that case, it is unnecessary to separately dispense a rinse aid and a salt for water softening into the machine dishwasher.

Commercial machine dishwashers consist basically of stationary bath tanks from which an essentially aqueous cleaning solution is jetted or sprayed onto the dishware, which moves past these baths on a conveyor belt, such that the used solution flows back into the bath tanks again. Water enters the last bath tank, flows via overflows in the manner of a cascade through all the other tanks and leaves the machine via the overflow of the first tank. The application of a generally highly alkaline cleaning solution generally takes place with the aid of nozzles provided therefor, or of a specific spraying system normally arranged in the middle region of the machine.

The inventive formulations for machine dishwashing are especially notable for excellent deposit-inhibiting action when used in the rinse cycle of a machine dishwasher (i.e. it acts as an incrustation inhibitor). They have inhibiting action with respect to both inorganic and organic deposits. The inorganic deposits are especially calcium and magnesium phosphate, calcium and magnesium carbonate, calcium and magnesium silicate and/or calcium and magnesium phosphonate, which arise from the calcium and magnesium salts present in the water and the builders present in standard dishwashing detergents. The organic deposits are especially soil constituents from the rinse liquor, for example protein, starch and fat deposits. The inventive formulations for machine dishwashing are also effective against carry-over deposits, which originate from the residual water in the bottom of the machine dishwasher and comprise, inter alia, dishwashing composition residues and possibly also soil residues from the previous wash cycle of the machine dishwasher.

The inventive formulation for machine dishwashing preferably comprises the following constituents:
a) at least one inventive polymer composition,
b) at least one builder (also referred to as sequestrant, builder material, complexing agent, chelator, chelating agent or softener),
c) optionally at least one enzyme,
d) optionally at least one bleach,
e1) water,
e2) optionally at least one thickener, and
e3) optionally at least one further additive, preferably selected from the following additives other than a): surfactants, bases, corrosion inhibitors, defoamers, dyes, fragrances, fillers, solubilizers and organic solvents.

The inventive formulation for machine dishwashing comprises, based on the total weight of the formulation, preferably:
a) 0.1% to 50% by weight of at least one inventive polymer composition,
b) 5% to 90% by weight of at least one builder and/or cobuilder,
c) 0% to 8% by weight of at least one enzyme,
d) 0% to 30% by weight of at least one bleach,
e1) 0.1% to 90% by weight of water,
e2) 0% to 8% by weight of at least one thickener,
e3) 0% to 25% by weight of at least one further additive,
with the proviso that the weights of components a) to e) add up to 100% by weight.

In a preferred embodiment, the inventive formulation for machine dishwashing comprises at least one enzyme.

The inventive formulation for machine dishwashing comprises, based on the total weight of the formulation, preferably:
a) 2% to 40% by weight of at least one inventive polymer composition,
b) 5% to 80% by weight of at least one builder and/or cobuilder,
c) 0.1% to 6% by weight of at least one enzyme,
d) 0% to 30% by weight of at least one bleach,
e1) 0.1% to 80% by weight of water,
e2) 0% to 6% by weight of at least one thickener,
e3), 0% to 25% by weight of at least one further additive,
with the proviso that the weights of components a) to e) add up to 100% by weight.

More preferably, the inventive formulation for machine dishwashing comprises, based on the total weight of the formulation:
a) 0.12% to 30% by weight of at least one inventive polymer composition,
b) 5% to 75% by weight of at least one builder and/or cobuilder,
c) 0.1% to 6% by weight of at least one enzyme,
d) 0% to 25% by weight of at least one bleach,
e1) 0.1% to 80% by weight of water,
e2) 0.1% to 5% by weight of at least one thickener,
e3) 0% to 25% by weight of at least one further additive,
with the proviso that the weights of components a) to e) add up to 100% by weight.

The polymer composition a) may be incorporated into the formulation or may be present in the overall formulation in a separate region as a clear gel component separately from the other components (for example divided by a film, for example of an inventive polymer composition or of polyvinyl alcohol).

The dishware cleaning formulations may be in the form of tablets or entirely liquid formulations. However, it is also possible for containers produced with films or shaped bodies, having 1 to 6 individual sections of equal or different size, to be present. These may independently be filled with powder, pellets, solids or liquids. The polymer composition a) is preferably dispensed in a separate compartment. The polymer composition a) may additionally be thickened or colored.

Component a)

With regard to inventive polymer compositions suitable and preferred as component a), reference is made to the details above.

Component b)

The inventive washing and cleaning and dishwashing compositions preferably comprise at least one builder.

Builders, which are sometimes also referred to as sequestrants, builder materials, complexing agents, chelators, chelating agents or softeners, bind alkaline earth metals and other water-soluble metal salts without precipitating. They help to break up soil, disperse soil components, help to detach soil and in some cases themselves have a washing effect. In addition, when they are solid and are used in pulverulent formulations, they keep the powder free-flowing.

Suitable builders may be either organic or inorganic in nature. Examples are aluminosilicates, carbonates, phosphates and polyphosphates, polycarboxylic acids, polycarboxylates, hydroxycarboxylic acids, phosphonic acids, e.g. hydroxyalkylphosphonic acids, phosphonates, aminopolycarboxylic acids and salts thereof, and polymeric compounds containing carboxylic acid groups and salts thereof.

Suitable inorganic builders are, for example, crystalline or amorphous aluminosilicates having ion-exchanging properties, such as zeolites. Various types of zeolites are suitable, especially zeolites A, X. B. P. MAP and HS in the sodium form thereof, or in forms in which Na has been partially exchanged for other cations such as Li, K. Ca, Mg or ammonium. Suitable zeolites are described, for example, in U.S. Pat. No. 4,604,224. Crystalline silicates suitable as builders are, for example, disilicates or sheet silicates, e.g. 5-$Na_2Si_2O_5$ or B—$Na_2Si_2O_5$ (SKS 6 or SKS 7). The silicates can be used in the form of their alkali metal, alkaline earth metal or ammonium salts, preferably as sodium, lithium and magnesium silicates. Amorphous silicates, for example sodium metasilicate which has a polymeric structure, or amorphous disilicate (Britesil® H 20, manufacturer: Akzo), are likewise usable. Among these, preference is given to sodium disilicate.

Suitable inorganic builder substances based on carbonate are carbonates and hydrogencarbonates. These can be used in the form of their alkali metal, alkaline earth metal or ammonium salts. Preference is given to using sodium, lithium and magnesium carbonates or sodium, lithium and magnesium hydrogencarbonates, especially sodium carbonate and/or sodium hydrogencarbonate.

Customary phosphates used as inorganic builders are alkali metal orthophosphates and/or polyphosphates, for example pentasodium triphosphate.

Suitable organic builders are, for example, $C_4$-$C_{30}$-di-, -tri- and -tetracarboxylic acids, for example succinic acid, propanetricarboxylic acid, butanetetracarboxylic acid, cyclopentanetetracarboxylic acid, and alkyl- and alkenyl-succinic acids having $C_2$-$C_{20}$-alkyl or -alkenyl radicals.

Suitable organic builders are also hydroxycarboxylic acids and polyhydroxycarboxylic acids (sugar acids). These include $C_4$-$C_{20}$-hydroxycarboxylic acids, for example malic acid, tartaric acid, gluconic acid, mucic acid, lactic acid, glutaric acid, citric acid, tartronic acid, glucoheptonic acid, lactobionic acid, and sucrosemono-, -di- and tricarboxylic acid. Among these, preference is given to citric acid and salts thereof.

Suitable organic builders are also phosphonic acids, for example hydroxyalkylphosphonic acids, aminophosphonic acids and the salts thereof. These include, for example, phosphonobutanetricarboxylic acid, aminotris(methylenephosphonic acid), ethylenediaminetetraethylenephosphonic acid, hexamethylenediaminetetramethylenephosphonic acid, diethylenetriamine-pentamethylenephosphonic acid, morpholinomethanediphosphonic acid, 1-hydroxy-$C_1$- to $C_{10}$-alkyl-1,1-diphosphonic acids such as 1-hydroxyethane-1,1-diphosphonic acid. Among these, preference is given to 1-hydroxyethane-1,1-diphosphonic acid and salts thereof.

Suitable organic builders are additionally aminopolycarboxylic acids, such as nitrilotriacetic acid (NTA), nitrilomonoacetic dipropionic acid, nitrilotripropionic acid, β-alaninediacetic acid (β-ADA), ethylenediaminetetraacetic acid (EDTA), diethylenetriaminepentaacetic acid, 1,3-propylenediaminetetraacetic acid, 1,2-propylenediaminetetraacetic acid, N-(alkyl)ethylenediaminetriacetic acid, N (hydroxyalkyl)ethylenediaminetriacetic acid, ethylenediaminetriacetic acid, cyclohexylene-1,2-diaminetetraacetic acid, iminodisuccinic acid, ethylenediaminedisuccinic acid, serinediacetic acid, isoserinediacetic acid, L-asparaginediacetic acid, L-glutaminediacetic acid, methylglycinediacetic acid (MGDA), and the salts of the aforementioned aminopolycarboxylic acids. Among these, preference is given to L-glutaminediacetic acid, methylglycinediacetic acid and salts thereof.

Suitable organic builders are additionally polymeric compounds containing carboxylic acid groups, such as acrylic acid homopolymers. These preferably have a number-average molecular weight in the range from 800 to 70 000 g/mol, more preferably from 900 to 50 000 g/mol, particularly from 1000 to 20 000 g/mol, especially 1000 to 10 000 g/mol. The term "acrylic acid homopolymer" also comprises polymers in which some or all of the carboxylic acid groups are in neutralized form. These include acrylic acid homopolymers in which some or all of the carboxylic acid groups are in the form of alkali metal salts or ammonium salts. Preference is given to acrylic acid homopolymers in which the carboxylic acid groups are protonated or in which some or all of the carboxylic acid groups are in the form of sodium salts.

Suitable polymeric compounds containing carboxylic acid groups are also oligomaleic acids, as described, for example, in EP-A 451 508 and EP-A 396 303.

Suitable polymeric compounds containing carboxylic acid groups are also terpolymers of unsaturated $C_4$-$C_8$-dicarboxylic acids, where the polymerized comonomers may include monoethylenically unsaturated monomers from group (i) specified below in amounts of up to 95% by weight, from group (ii) in amounts of up to 60% by weight and from group (iii) in amounts of up to 20% by weight. Suitable unsaturated $C_4$-$C_8$-dicarboxylic acids in this context are, for example, maleic acid, fumaric acid, itaconic acid and citraconic acid. Preference is given to maleic acid. Group (i) comprises monoethylenically unsaturated $C_3$-$C_8$-monocarboxylic acids, for example acrylic acid, methacrylic acid, crotonic acid and vinylacetic acid. From group (i), preference is given to using acrylic acid and methacrylic acid. Group (ii) comprises monoethylenically unsaturated $C_2$-$C_{22}$-olefins, vinyl alkyl ethers having $C_1$-$C_8$-alkyl groups, styrene, vinyl esters of $C_1$-$C_8$-carboxylic acids, (meth)acrylamide and vinylpyrrolidone. From group (ii), preference is given to using $C_2$-$C_6$-olefins, vinyl alkyl ethers having $C_1$-$C_4$-alkyl groups, vinyl acetate and vinyl propionate. If the polymers of group (ii) comprise vinyl esters in polymerized form, they may also be present partly or fully hydrolyzed to vinyl alcohol structural units. Suitable co- and terpolymers are known, for example, from U.S. Pat. No. 3,887,806 and DE-A 4313909. Group (iii) comprises (meth) acrylic esters of $C_1$-$C_6$ alcohols, (meth)acrylonitrile, (meth) acrylamides of $C_1$-$C_8$ amines, N-vinylformamide and Suitable polymeric compounds containing carboxylic acid groups are also homopolymers of the monoethylenically unsaturated $C_3$-$C_8$-monocarboxylic acids, for example acrylic acid, methacrylic acid, crotonic acid and vinylacetic acid, especially of acrylic acid and methacrylic acid, copolymers of dicarboxylic acids, for example copolymers of maleic acid and acrylic acid in a weight ratio of 10:90 to 95:5, more preferably those in a weight ratio of from 30:70 to 90:10 with molar masses of from 1000 to 150 000; terpolymers of maleic acid, acrylic acid and a vinyl ester of a $C_1$-$C_3$-carboxylic acid in a weight ratio of from 10 (maleic acid):90 (acrylic acid+vinyl ester) to 95 (maleic acid):10 (acrylic acid+vinyl ester), where the weight ratio of acrylic acid to the vinyl ester may vary within the range from 30:70 to 70:30; copolymers of maleic acid with $C_2$-$C_8$-olefins in a molar ratio of from 40:60 to 80:20, particular preference being given to copolymers of maleic acid with ethylene, propylene or isobutene in a molar ratio of 50:50.

Suitable polymeric compounds containing carboxylic acid groups are also copolymers of 50% to 98% by weight of ethylenically unsaturated weak carboxylic acids with 2% to 50% by weight of ethylenically unsaturated sulfonic acids, as described, for example, in EP-A-0877002. Suitable weak ethylenically unsaturated carboxylic acids are especially $C_3$-$C_6$-monocarboxylic acids, such as acrylic acid and methacrylic acid. Suitable ethylenically unsaturated sulfonic acids are 2-acetylamidomethyl-1-propanesulfonic acid, 2-methacrylamido-2-methyl-1-propanesulfonic acid, 2-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 3-sulfopropyl methacrylate, sulfomethylacrylamide, sulfomethylmethacrylamide and salts of these acids. The copolymers may also comprise, in copolymerized form, 0 to 30% by weight of ethylenically unsaturated $C_4$-$C_8$-dicarboxylic acids, such as maleic acid, and 0 to 30% by weight of at least one monomer which is copolymerizable with the aforementioned monomers. The latter are, for example, $C_1$-$C_4$-alkyl esters of (meth)acrylic acid, $C_1$-$C_4$-hydroxyalkyl esters of (meth)acrylic acid, acrylamide, alkyl-substituted acrylamide. N,N-dialkyl-substituted acrylamide, vinylphosphonic acid, vinyl acetate, allyl alcohols, sulfonated allyl alcohols, styrene and other vinylaromatics, acrylonitrile, N-vinylpyrrolidone, N-vinylformamide, N-vinylimidazole or N-vinylpyridine. The weight-average molecular weight of these copolymers is within the range from 3000 to 50 000 daltons. Particularly suitable copolymers are those with about 77% by weight of at least one ethylenically unsaturated $C_3$-$C_6$-monocarboxylic acid and about 23% by weight of at least one ethylenically unsaturated sulfonic acid.

Graft polymers of unsaturated carboxylic acids onto low molecular weight carbohydrates or hydrogenated carbohydrates (cf. U.S. Pat. No. 5,227,446, DE-A 4415623 and DE-A 4313908\ are likewise suitable. Suitable unsaturated carboxylic acids in this context are, for example, maleic acid, fumaric acid, itaconic acid, citraconic acid, acrylic acid, methacrylic acid, crotonic acid and vinylacetic acid and also mixtures of acrylic acid and maleic acid, which are grafted on in amounts of 40% to 95% by weight, based on the component to be grafted. For modification, it is additionally possible for up to 30% by weight, based on the component to be grafted, of further monoethylenically unsaturated monomers to be present in polymerized form. Suitable modifying monomers are the abovementioned monomers of groups (ii) and (iii). Suitable graft bases are degraded polysaccharides, for example acidically or enzymatically degraded starches, inulins or cellulose, protein hydrolyzates and reduced (hydrogenated or hydrogenatingly aminated) degraded polysaccharides, for example mannitol, sorbitol, aminosorbitol and N-alkylglucamine, as are polyalkylene glycols with molar masses of up to $M_w$=5000, for example polyethylene glycols, ethylene oxide/propylene oxide or ethylene oxide/butylene oxide or ethylene oxide/propylene oxide/butylene oxide block copolymers and alkoxylated mono- or polyhydric $C_1$-$C_{22}$ alcohols (cf. U.S. Pat. No. 5,756,456).

Likewise suitable are polyglyoxylic acids, as described, for example, in EP-B 001004, U.S. Pat. No. 5,399,286, DE-A-4106355 and EP-A-656914. The end groups of the polyglyoxylic acids may have different structures.

Additionally suitable are polyamidocarboxylic acids and modified polyamidocarboxylic acids; these are, for example, known from EP-A-454126, EP-B-511037, WO-A-94/01486 and EP-A-581452.

Polyaspartic acids or cocondensates of aspartic acid with further amino acids, $C_4$-$C_{25}$ mono- or -dicarboxylic acids and/or $C_4$-$C_{25}$ mono- or -diamines can also be used as polymeric compounds containing carboxylic acid groups. Particular preference is given to using polyaspartic acids which have been prepared in phosphorus acids and have been modified with $C_6$-$C_{22}$ mono- or -dicarboxylic acids or with $C_6$-$C_{22}$ mono- or -diamines.

Among the polymeric compounds containing carboxylic acid groups, polyacrylic acids are preferred, including in partly or fully neutralized form.

Suitable organic builders are also iminodisuccinic acid, oxydisuccinic acid, aminopolycarboxylates, alkyl polyaminocarboxylates, aminopolyalkylenephosphonates, polyglutamates, hydrophobically modified citric acid, for example agaric acid, poly-α-hydroxyacrylic acid, N-acylethylenediamine triacetates such as lauroylethylenediamine triacetate and alkylamides of ethylenediaminetetraacetic acid, such as EDTA tallow amide.

In addition, it is also possible to use oxidized starches as organic builders.

Preference is given to using, as component b), a mixture of different builders.

The mixture of different builders preferably comprises at least two of the following constituents: at least one carbonate (e.g. sodium carbonate), at least one silicate (e.g. sodium disilicate), at least one polymeric compound containing carboxylic acid groups or at least one polymeric compound which contains carboxylic acid groups of which all or some are present in neutralized form (e.g. polyacrylic acid), at least one (poly)hydroxycarboxylic acid or a salt thereof (e.g. citric acid or a citrate), at least one aminopolycarboxylic acid or a salt thereof (e.g. methylglycinediacetic acid or a salt thereof, e.g. a sodium salt thereof), at least one phosphonic acid (e.g. 1-hydroxyethane-1-(1,1-diphosphonic acid); HEDP), at least one phosphate. More preferably, the mixture comprises at least one carbonate, at least one silicate and at least one polymeric, optionally (partially) neutralized compound containing carboxylic acid groups, and optionally at least one of the following constituents: at least one (poly)hydroxycarboxylic acid or a salt thereof, at least one phosphonic acid, at least one phosphate. The mixture especially comprises at least one carbonate, at least one silicate, at least one polymeric, optionally (partially) neutralized compound containing carboxylic acid groups, at least one (poly)hydroxycarboxylic acid or a salt thereof, and at least one phosphonic acid, and optionally at least one phosphate.

In such a mixture, the constituents are present preferably in the following amounts:

b1) at least one carbonate: 10% to 50% by weight;
b2) at least one silicate: 1% to 10% by weight;
b3) at least one polymeric, optionally (partially) neutralized compound containing carboxylic acid groups: 5% to 20% by weight;
b4) at least one (poly)hydroxycarboxylic acid or a salt thereof: 0% to 50% by weight;
b5) at least one aminopolycarboxylic acid or a salt thereof: 0% to 60% by weight;
b6) at least one phosphonic acid: 0.2% to 1% by weight;
b7) at least one phosphate: 0% to 60% by weight.

The percentages by weight are each based on the total weight of the builder. The weights of b1) to b7) add up to 100% by weight.

Component c)

The inventive washing and cleaning and dishwashing compositions preferably comprise at least one enzyme.

Suitable enzymes are those as typically used as industrial enzymes. These include both enzymes having optimal activity in the neutral to alkaline pH range and enzymes having optimal activity in the acidic pH range.

The enzymes are preferably selected from aminopeptidases, amylases, arabinases, carbohydrases, carboxypeptidases, catalases, cellulases, chitinases, cutinases, cyclodextrin glycosyltransferases, deoxyribonucleases, esterases, galactanases, alpha-galactosidases, beta-galactosidases, glucanases, glucoamylases, alpha-glucosidases, beta-glucosidases, haloperoxidases, hydrolase invertases, isomerases, keratinases, laccases, lipases, mannanases, mannosidases, oxidases, pectinolytic enzymes, peptidoglutaminases, peroxidases, peroxygenases, phytases, polyphenol oxidases, proteolytic enzymes, ribonucleases, transglutaminases, transferases, xylanases and mixtures thereof.

The enzymes are especially selected from hydrolases, such as proteases, esterases, glucosidases, lipases, amylases, cellulases, mannanases, other glycosyl hydrolases and mixtures of the aforementioned enzymes. All these hydrolases contribute to soil dissolution and removal from protein-, grease- or starch-containing stains. It is also possible to use oxireductases for bleaching. Of particularly good suitability are active enzymatic ingredients obtained from bacterial strains or fungi such as *Bacillus subtilis, Bacillus licheniformis, Streptomyceus griseus* and *Humicola insolens*.

Preferred enzymes are described in detail below:

Proteases:

Suitable proteolytic enzymes (proteases) may in principle be of animal, vegetable or microbial origin. Preference is given to proteolytic enzymes of microbial origin. These also include chemically or genetically modified mutants.

Preferred proteases are serine proteases, metalloproteases or trypsin-like proteases.

Preference is given to using an alkaline microbial protease. Examples of alkaline proteases are subtilisins, especially those derived from *Bacillus*, e.g. subtilisin Novo, subtilisin Carlsberg, subtilisin 309, subtilisin 147 and subtilisin 168 (described in WO 89/06279). Examples of trypsin-like proteases are trypsin (e.g. porcine or bovine) and the *Fusarium* protease described, for example, in WO 89/06270.

Preferred commercially available proteases include the proteases available under the following brand names: Alcalase™ Savinase™, Primase™, Durazym™, Esperase™, Neutrase™ from Novozymes A/S (Denmark), the products sold by DuPont/Genencor under the Maxatase™, Maxacal™, Maxapem™, PREFERENZ™ P, EXCELLENZ™ P Properase™, Purafect™ and Purafect™ OXP brand names, and the products sold by Solvay Enzymes under the Opticlean™ and Optimase™ brand names.

The inventive compositions preferably comprise at least one protease in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one protease in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Lipases:

Suitable lipases may in principle originate from bacteria or fungi. These also include chemically or genetically modified mutants.

Examples of suitable lipases are *Humicola lanuginosa* lipase, described, for example, in EP 258 068 und EP 305 216, *Rhizomucor miehei* lipase, described, for example, in EP 238 023, *Candida* lipase, such as *C. antarctica* lipase, for example the *C. antarctia* lipases A or B as described in EP 214 761, *Pseudomonas* lipase such as *P. alcaligenes* and *P. pseudoalcaligenes* lipase, described, for example, in EP 218 272, *P. cepacia* lipase, described, for example, in EP 331 376, *P. stutzeri* lipase, described, for example, in GB 1,372, 034, *P. fluorescens* lipase, *Bacillus* lipase, for example a *B. subtilis* lipase (Dartois et al., (1993), Biochemica et Biophysica acta 1131, 253-260), *B. stearothermophilus* lipase (JP 64/744992) and *B. pumilus* lipase (WO 91/16422).

In addition, a multitude of cloned lipases is suitable, comprising *Penicillium camembertii* lipase described by Yamaguchi et al., (1991), Gene 103, 61-67), *Geotricum candidum* lipase (Schimada, Y. et al., (1989), J. Biochem., 106, 383-388), and various *Rhizopus* lipases, such as *R. delemar* lipase (Hass, M. J et al., (1991), Gene 109, 117-113), *R. niveus* lipase (Kugimiya et al., (1992), Biosci. Biotech. Biochem. 56, 716-719) and *R. oryzae* lipase.

In addition, it is possible to use other types of lipolytic enzymes, such as cutinases, for example a cutinase derived from *Pseudomonas mendocina*, as described, for example, in WO 88/09367, or a cutinase derived from *Fusarium solani pisi* (as described, for example, in WO 90/09446).

Especially suitable lipases are MI Lipase™, Luma Fast™ and Lipo-Max™ (Genencor), Lipoclean™, Lipex™, Lipolex™ Lipolase™ and Lipolase Ultra™ (Novozymes NS), and Lipase P "Amano" (Amano Pharmaceutical Co. Ltd.).

The inventive compositions preferably comprise at least one lipase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one lipase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Amylases;

In principle, all α- and/or β-amylases are suitable. Suitable amylases may in principle originate from bacteria or fungi. These also include chemically or genetically modified mutants.

Examples of suitable amylases are α-amylases obtained from a specific strain of *B. amyloliquefaciens* or *B. licheniformis*, described in detail in GB 1,296,839. Further suitable amylases comprise backbones known as SP707 from *Bacillus* sp, AP1378, BSG *B. stearothermophilus* alpha-amylase, SP690, SP722, and AA560 from *Bacillus* sp. Suitable commercially available amylases are Stainzyme™, Stainzyme Plus™, Natalase™, Duramyl™, Termamyl™, Fungamyl™ and BAN™ (available from Novozymes A/S), and Rapidase™, PREFERENZ™ S, EXCELLENZ™ S and Maxamyl P™ (available from Genencor).

The inventive compositions preferably comprise at least one amylase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one amylase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Cellulases:

In principle, all cellulases are suitable. Suitable cellulases may in principle originate from bacteria or fungi. These also include chemically or genetically modified mutants.

Suitable cellulases are described in U.S. Pat. No. 4,435,307. These are fungal cellulases produced from *Humicola insolens*. Cellulases having color care properties are especially suitable. Examples of such cellulases are described in EP 0 495 257.

Suitable commercially available cellulases comprise Celluzyme™ produced from a strain of *Humicola insolens*, Carezyme™, Celluclean™, Endolase™, Whitezyme™ (Novozymes A/S), REVITALENZ™ (DuPont), Biotouch C™ (AB Enzymes) and KAC-500(B)™ (Kao Corporation).

The inventive compositions preferably comprise at least one cellulase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one cellulase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Peroxidases/Oxidases:

Suitable peroxidases/oxidases may in principle originate from plants, bacteria or fungi. These also include chemically or genetically modified mutants.

Peroxidase enzymes are used in combination with hydrogen peroxide or a hydrogen peroxide source (e.g. a percarbonate, perborate or persulfate). Oxidase enzymes are used in combination with oxygen. Both enzyme types are used for "solution bleaching", in order to avoid dye transfer from a colored fabric to another fabric when they are washed together in a liquor. They can preferably be used together with action improvers described, for example, in WO 94/12621 and WO 95/01426.

The inventive compositions preferably comprise at least one peroxidase or oxidase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one peroxidase or oxidase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Lyases:

In principle, all lyases are suitable. Suitable lyases may in principle originate from bacteria or fungi. These also include chemically or genetically modified mutants.

Suitable lyases are pectate lyases or pectin lyases. Suitable commercially available lyases comprise XPect™ (Novozymes A/S) and PREFERENZ™ F (DuPont).

The inventive compositions preferably comprise at least one lyase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one lyase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

Inventive compositions may comprise further enzymes encompassed by the term hemicellulases. These include, for example, mannanases, xanthan lyases, pectinylases (=pectinases), pectin esterases, xyloglucanases (=xylanases), pullulanases and β-glucanases.

The inventive compositions preferably comprise at least one hemicellulase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the inventive polymer composition.

More particularly, the inventive composition is in the form of an enzyme-containing film. In that case, the inventive composition preferably comprises at least one hemicellulase in an amount of 0.00001% by weight to 30% by weight of enzyme protein, more preferably of 0.0001% by weight to 15% by weight of enzyme protein, especially 0.001% by weight to 10% by weight of enzyme protein, especially 0.001% by weight to 5% by weight of enzyme protein, based on the total weight of the enzyme-containing film.

The inventive washing, cleaning and dishwashing composition preferably comprises at least one enzyme selected from proteases, amylases, mannanases, cellulases, lipases, pectin lyases and mixtures thereof.

The inventive washing, cleaning and dishwashing composition preferably comprises at least one protease and/or amylase, The inventive washing, cleaning and dishwashing composition preferably comprises at least one enzyme mixture. Preference is given, for example, to enzyme mixtures comprising or consisting of the following enzymes:
  protease and amylase,
  protease and lipase (or lipolytic enzymes),
  protease and cellulase,
  amylase, cellulase and lipase (or lipolytic enzymes),
  protease, amylase and lipase (or lipolytic enzymes),
  protease, lipase (or lipolytic enzymes) and cellulase, The enzymes may be adsorbed on carrier substances in order to protect them from premature breakdown.

Optionally, the inventive washing, cleaning and dishwashing composition may also comprise enzyme stabilizers, Examples of these include calcium propionate, sodium formate, boric acids, boronic acids and salts thereof, such as 4-formylphenylboronic acid, peptides and peptide derivatives, for example peptide aldehydes, polyols such as propane-1,2-diol, and mixtures thereof.

Component d)

The bleaches d) are preferably bleach systems which, as well as bleaches, possibly also comprise bleach activators, bleach catalysts and/or bleach stabilizers.

Suitable bleaches are, for example, percarboxylic acids, for example diperoxododecanedicarboxylic acid, phthalimidopercaproic acid or monoperoxophthalic acid or -terephthalic acid, salts of percarboxylic acids, for example sodium percarbonate, adducts of hydrogen peroxide onto inorganic salts, for example sodium perborate monohydrate, sodium perborate tetrahydrate, sodium carbonate perhydrate or sodium phosphate perhydrate, adducts of hydrogen peroxide onto organic compounds, for example urea perhydrate, or of inorganic peroxo salts, for example alkali metal persulfates or peroxodisulfates.

Suitable bleach activators are, for example, polyacylated sugars, e.g. pentaacetylglucose; acyloxybenzenesulfonic acids and their alkali metal and alkaline earth metal salts, e.g. sodium p-nonanoyloxybenzenesulfonate or sodium p-benzoyloxybenzenesulfonate;

N,N-diacylated and N,N,N',Ni-tetraacylated amines, e.g. N,N,N',N'-tetraacetylmethylenediamine and -ethylenediamine (TAED), N,N-diacetylaniline, N,N-diacetyl-p-toluidine or 1,3-diacylated hydantoins such as 1,3-diacetyl-5,5-dimethylhydantoin; N-alkyl-N-sulfonylcarbonamides, e.g. N-methyl-N-mesylacetamide or N-methyl-N-mesylbenzamide; N-acylated cyclic hydrazides, acylated triazoles or urazoles, e.g. monoacetylmaleic hydrazide; O,N,N-trisubstituted hydroxylamines, e.g. O-benzoyl-N,N-succinylhydroxylamine, O-acetyl-N,N-succinylhydroxylamine or O,N,N-triacetylhydroxylamine; N,N'-diacylsulfurylamides, e.g. N,N'-dimethyl-N,N'-diacetylsulfurylamide or N,N'-diethyl-N,N'-dipropionylsulfurylamide; acylated lactams, for example acetylcaprolactam, octanoylcaprolactam, benzoylcaprolactam or carbonylbiscaprolactam; anthranil derivatives, for example 2-methylanthranil or 2-phenylanthranil; triacyl cyanurates, e.g. triacetyl cyanurate or tribenzoyl cyanurate; oxime esters and bisoxime esters, for example O-acetylacetone oxime or bisisopropyl iminocarbonate; carboxylic anhydrides, e.g. acetic anhydride, benzoic anhydride, m-chlorobenzoic anhydride or phthalic anhydride; enol esters, for example isopropenyl acetate; 1,3-diacyl-4,5-diacyloxyimidazolines, e.g. 1,3-diacetyl-4,5-diacetoxyimidazoline; tetraacetylglycoluril and tetrapropionylglycoluril; diacylated 2,5-diketopiperazines, e.g. 1,4-diacetyl-2,5-diketopiperazine; ammonium-substituted nitriles, for example N-methylmorpholinioacetonitrile methylsulfate; acylation products of propylenediurea and 2,2-dimethylpropylenediurea, e.g. tetraacetylpropylenediurea; α-acyloxypolyacylmalonamides, e.g. α-acetoxy-N,N'-diacetylmalonamide; diacyldioxohexahydro-1,3,5-triazines, e.g. 1,5-diacetyl-2,4-dioxohexahydro-1,3,5-triazine; benz-(4H)-1,3-oxazin-4-ones with alkyl radicals, e.g. methyl, or aromatic radicals, e.g. phenyl, in the 2 position.

A bleach system composed of bleaches and bleach activators may optionally also comprise bleach catalysts. Suitable bleach catalysts are, for example, quaternized imines and sulfonimines, described, for example, in U.S. Pat. No. 5,360,569 and EP-A 453 003. Particularly effective bleach catalysts are manganese complexes, described, for example, in WO-A 94/21777. In the case that they are used in the washing and cleaning compositions, such compounds are incorporated at most in amounts up to 1.5% by weight, especially up to 0.5% by weight, and in the case of very active manganese complexes in amounts up to 0.1% by weight. In addition to the described bleach system composed of bleaches, bleach activators and optionally bleach catalysts, it is also possible to use systems with enzymatic peroxide release or photoactivated bleach systems for the inventive washing and cleaning compositions.

Component e)

The inventive washing, cleaning and dishwashing compositions may comprise water as additive e) (=component e1). In a specific embodiment, the inventive washing, cleaning and dishwashing compositions comprise 0.1% to 80% by weight of water.

The inventive washing, cleaning and dishwashing compositions generally already have advantageous rheological properties because of the polymer compositions present in the form of liquid and especially aqueous composition.

In order to impart the desired viscosity to liquid and especially aqueous compositions of the inventive washing, cleaning and dishwashing compositions, it is additionally possible to use at least one thickener (=component e2) as component e).

In principle, any known thickeners (rheology modifiers) are suitable, provided that they do not exert any adverse effect on the action of the washing and cleaning composition. Suitable thickeners may be of natural origin or synthetic in nature.

Examples of thickeners of natural origin are xanthan, carob seed flour, guar flour, carrageenan, agar, tragacanth, gum arabic, alginates, modified starches such as hydroxyethyl starch, starch phosphate esters or starch acetates, dextrins, pectins, and cellulose derivatives such as carboxymethyl cellulose, hydroxyethyl cellulose, hydroxypropyl cellulose, hydroxypropylmethyl cellulose, methyl cellulose and the like. Thickeners of natural origin are also inorganic thickeners, such as polysilicic acids and clay minerals, e.g. sheet silicates, and also the silicates specified for the builders.

Examples of synthetic thickeners are polyacrylic and polymethacrylic compounds, such as (partly) crosslinked homopolymers of acrylic acid, for example with an allyl ether of sucrose or pentaerythritol or homopolymers of acrylic acid crosslinked with propylene (carbomer), for example the Carbopol® products from BF Goodrich (e.g. Carbopol® 676, 940, 941, 934 and the like) or the Polygel® products from 3V Sigma (e.g. Polygel® DA), copolymers of ethylenically unsaturated mono- or dicarboxylic acids, for example terpolymers of acrylic acid, methacrylic acid or maleic acid with methyl or ethyl acrylate and a (meth) acrylate which is derived from long-chain ethoxylated alcohols, for example the Acusol® products from Rohm & Haas (e.g. Acusol® 820 or 1206A), copolymers of two or more monomers, which are selected from acrylic acid, methacrylic acid and their $C_1$-$C_4$-alkyl esters, for example copolymers of methacrylic acid, butyl acrylate and methyl methacrylate or of butyl acrylate and methyl methacrylate, for example the Aculyn® and Acusol® products from Rohm & Haas (e.g. Aculyn® 22, 28 or 33 and Acusol® 810, 823 and 830), or crosslinked high molecular weight acrylic acid copolymers, for example copolymers, crosslinked with an allyl ether of sucrose or pentaerythritol, of $C_{10}$-$C_{30}$-alkyl acrylates with one or more comonomers which are selected from acrylic acid, methacrylic acid and their $C_1$-$C_4$-alkyl esters (e.g. Carbopol® ETD 2623, Carbopol® 1382 or Carbopol® AQUA 30 from Rohm & Haas).

Examples of synthetic thickeners are also reaction products of maleic acid polymers with ethoxylated long-chain alcohols, for example the Surfonic L series from Texaco Chemical Co. or Gantrez AN-119 from ISP; polyethylene glycols, polyamides, polyimines and polycarboxylic acids.

Mixtures of the abovementioned thickeners are also suitable,

Preferred thickeners are xanthans and the abovementioned polyacrylic and polymethacrylic compounds.

The inventive washing, cleaning and dishwashing compositions may comprise at least one further additive as additive e).

Surfactants from group e3) other than component a) may be cationic, anionic, zwitterionic or nonionic. Suitable surfactants are those mentioned above for the surfactant systems.

Suitable organic solvents e3) are selected from mono- or polyhydric alcohols, alkanolamines and glycol ethers. They are preferably selected from ethanol, n- or propanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl oder monoethyl ether, methoxy-, ethoxy- or butoxytriglycol, butoxyethoxy-2-propanol, 3-methyl-3-methoxybutanol, propylene glycol t-butyl ether and mixtures of these solvents.

Useful foam inhibitors or defoamers for component e3) include, for example, soaps, paraffins or silicone oils, which may optionally be applied to support materials.

Suitable bases for component e3) are alkali metal hydroxides, alkaline earth metal hydroxides, alkali metal carbonates, alkaline earth metal carbonates, ammonium carbonate, alkali metal hydrogencarbonates, alkaline earth metal hydrogencarbonates, ammonium hydrogencarbonate and mixtures thereof. Preference is given to using sodium, lithium and magnesium carbonates or sodium, lithium and magnesium hydrogencarbonates, especially sodium carbonate and/or sodium hydrogencarbonate.

In addition, the inventive washing, cleaning or dishwashing compositions may comprise further additives e) which further improve the performance and/or esthetic properties. In general, preferred compositions comprise, in addition to the aforementioned components, at least one further additive selected from electrolytes, pH modifiers, perfume carriers, fluorescers, hydrotropes, antiredeposition agents, optical brighteners, graying inhibitors, shrink inhibitors, crease inhibitors, dye transfer inhibitors, active antimicrobial ingredients, antioxidants, corrosion inhibitors, antistats, ironing aids, hydrophobizing and impregnating agents, swell and antislip agents and UV absorbers.

In order to improve the esthetic impression of the inventive washing, cleaning or dishwashing compositions, they can be colored with suitable dyes. Preferred dyes, the selection of which presents no difficulty whatsoever to the person skilled in the art, have a high storage stability and insensitivity with respect to the other ingredients of the compositions and to light, and do not have any marked substantivity toward textile fibers, in order not to stain them.

I & I cleaners

The inventive polymer compositions are especially suitable for industrial and institutional cleaners (I & I cleaners). Industrial and institutional cleaners are typically washing compositions, all-purpose cleaners, foam cleaners, gel cleaners, CIP (cleaning in place) cleaners for professional and generally automated clearing operations, for example in industrial laundries, dairies, breweries, the food and drink industry, the pharmaceutical industry or pharmaceutical formulation, or sanitary cleaners.

The cleaners may be strongly basic with a high electrolyte content and, if required, comprise bleaches (such as hydrogen peroxide, sodium hypochlorite) or disinfectants and defoamers (for example in bottle cleaning). It is also possible for the standard aforementioned enzymes to be present in the industrial and institutional cleaners. There is a great variety in terms of the types of cleaning for which the inventive formulations are suitable. Examples include cleaning baths (stationary or mobile), spray cleaning, ultrasound cleaning, steam jet cleaning and high-pressure cleaning, optionally in combination with mechanical cleaning, for example by means of rotating brushes.

Said formulations for cleaning include those for industry, transport, commerce and industry, and for the private sector. Specific examples include: professional laundries, professional cleaning businesses, ore processing industry, metal and metalworking industry, automobile and automobile supply industry, electrical industry, electronics industry, photographic industry and businesses, leisure industry and businesses, construction material industry, brewing industry and businesses; foods industry (e.g. processing or production of meat, poultry, dairy and fish products), animal nutrition industry, cosmetics industry, pharmaceutical industry, agrochemical industry, gastronomy, the health sector, workshops, and public transport. Examples of objects to be cleaned are institutional laundry, hospital laundry, laundry from laundry collection, buildings containing living spaces, office spaces or commercial spaces of a wide variety of different kinds, and sanitary spaces, warehouses, breweries, small businesses such as bakeries, butcheries and supermarkets; hospitals, care homes, homes for the elderly, administration buildings, factory buildings, doctors' practices; and also motor vehicles (cars and trucks), buses, road tanker vehicles (interior and exterior), rail tanker wagons, passenger vehicles and goods vehicles, and aircraft and ships; and also building facades, tiled or painted walls, wooden floors (parquet, boards) with screed or textile or plastics coverings, signaling and lighting installations, furniture, railings, overhead signage, other signage, safety reflectors, delineating markers, tanks, dishware, glass panes, roads and paths, outside paving, road and railway tunnels.

Film Applications

The invention further provides a process for producing an inventive polymer composition in the form of a film, in which a polymer obtainable by the process according to the invention, optionally after addition of at least one active ingredient and/or at least one additive, is subjected to a film-forming operation, preferably selected from blow-molding, thermoforming, casting and calendering.

With regard to suitable and preferred polymer compositions for films, reference is made to the above remarks in full.

As explained above, for use in the form of a film, preference is given to using flexible inventive polymer compositions having a low glass transition temperature $T_G$. Preferably, the inventive polymer compositions for use in the form of a film have a glass transition temperature $T_G$ in the range from 0 to 50° C., preferably from 5 to 20° C.

A specific execution is a process for producing an inventive polymer composition in the form of a film comprising at least one active ingredient. Suitable active ingredients are those already mentioned above as components b) to e), to which reference is made here in full. The active ingredient is preferably selected from enzymes, builders, bleaches, surfactants, bases, corrosion inhibitors, defoamers, dyes, fragrances, fillers, tableting aids, disintegrants, thickeners, solubilizers, organic solvents, electrolytes, pH modifiers, perfume carriers, fluorescers, hydrotropes, antiredeposition agents, optical brighteners, graying inhibitors, shrink inhibitors, crease inhibitors, dye transfer inhibitors, active antimicrobial ingredients, antioxidants, corrosion inhibitors, antistats, ironing aids, hydrophobizing and impregnating agents, swell and antislip agents, UV absorbers and mixtures thereof.

A very specific execution is a process for producing an inventive polymer composition in the form of a film comprising at least enzyme. Suitable enzymes are those mentioned above as components c), to which reference is made here in full.

For production of films, additives can be added to the inventive polymer composition before and/or during film production. The additives for production of an inventive film are preferably selected from plasticizers, agents for modifying gas permeability and water vapor permeability, antistats, lubricants, slip agents, dissolution aids, dyes, pigments and mixtures thereof. In a specific execution, at least one plasticizer is added to the polymer material, which imparts permanent flexibility to the film and sheaths produced therefrom. Suitable plasticizers are alkylene glycols, oligoalkylene glycols, other polyols, alkyleneimines, oligoalkyleneimines and mixtures thereof. The plasticizer is preferably selected from glycerol, propylene glycol, diethylene glycol, triethylene glycol, sorbitol, diethyleneimine, triethyleneimine, and mixtures thereof.

In principle, the film production process is not subject to any particular restrictions, and the person skilled in the art, using a suitable inventive polymer composition, can employ any desired production process known in the from his specialist knowledge. The same applies to the production of sheaths based on an inventive film. Extrusion processes and casting processes are particularly suitable.

In the production of films by extrusion, for example, a polymer composition obtainable by the process according to the invention, optionally after addition of at least one active ingredient and/or at least one additive, is extruded, blown to a film in a blowing process, or formed to a film in a thermoforming process, and the film thus obtained is optionally brought into a form suitable for the ensheathing of washing composition, dishwashing composition or cleaning composition portions.

In the production of films by casting, for example, a polymer composition obtainable by the process according to the invention, optionally after addition of at least one additive, is melted or dissolved in a suitable solvent or solvent mixture, the free-flowing polymer composition thus obtained is cast to form a film, and the solvent or solvent mixture is optionally removed by evaporation.

Suitable solvents and solvent mixtures are those described above as component S), to which reference is made here in full. The solvent is more preferably selected from water, ethanol, n-propanol, isopropanol, ethylene glycol, diethylene glycol, 1,2-propylene glycol, 1,2-dipropylene glycol and mixtures thereof. In a specific embodiment, the solvent used is selected from water and a mixture of water and at least one solvent other than water, selected from ethanol, n-propanol, isopropanol, ethylene glycol, diethylene glycol, 1,2-propylene glycol, 1,2-dipropylene glycol and mixtures thereof.

The inventive polymer compositions are generally thermoplastic and can be subjected to forming by thermoforming (i.e. hot forming, deep drawing or vacuum deep drawing). A process for producing water-soluble film packages by a thermoforming process, which comprises a hot forming or deep drawing step, is described in WO 00/55044.

For production of film portions, the film material can be processed in a suitable manner, for example by cutting to a desired size and/or folding to form compartments. Subsequently the edges can be closed by customary sealing processes, such as heat sealing, liquid sealing or pressure sealing.

Coatings

The invention further provides a process for producing an inventive polymer composition in the form of a coating on a substrate, in which a polymer obtainable by the process according to the invention, optionally after addition of at least one active ingredient and/or at least one additive and/or at least one solvent and optionally while heating, is converted to a free-flowing form, applied to a substrate and allowed to solidify.

With regard to suitable and preferred polymer compositions for coatings on a substrate, reference is made to the above remarks in full.

As explained above, for use in the form of a coating, preference is given to using flexible inventive polymer compositions having a low glass transition temperature $T_G$. Preferably, the inventive polymer compositions for use in the form of a coating have a glass transition temperature $T_G$ in the range from 0 to 50° C., preferably from 5 to 20° C.

A specific execution is a process for producing an inventive polymer composition in the form of a coating on a substrate, comprising at least one active ingredient. Suitable active ingredients are those already mentioned above as components b) to e), to which reference is made here in full. The active ingredient is preferably selected from enzymes, builders, bleaches, surfactants, bases, corrosion inhibitors, defoamers, dyes, fragrances, fillers, tableting aids, disintegrants, thickeners, solubilizers, organic solvents, electrolytes, pH modifiers, perfume carriers, fluorescers, hydrotropes, antiredeposition agents, optical brighteners, graying inhibitors, shrink inhibitors, crease inhibitors, dye transfer inhibitors, active antimicrobial ingredients, antioxidants, corrosion inhibitors, antistats, ironing aids, hydrophobizing and impregnating agents, swell and antislip agents, UV absorbers and mixtures thereof.

A very specific execution is a process for producing an inventive polymer composition in the form of a coating on a substrate, comprising at least one enzyme. Suitable enzymes are those mentioned above as components c), to which reference is made here in full.

Additives for production of coatings can be added to the inventive polymer composition before and/or during coating production. The additives for production of an inventive coating are preferably selected from those mentioned above for film formation. Reference is made thereto in full.

Suitable solvents and solvent mixtures for production of coatings are those described above as component S), to which reference is made here in full. The solvent is more preferably selected from water, ethanol, n-propanol, isopropanol, ethylene glycol, diethylene glycol, 1,2-propylene glycol, 1,2-dipropylene glycol and mixtures thereof. In a specific embodiment, the solvent used is selected from water and a mixture of water and at least one solvent other than water, selected from ethanol, n-propanol, isopropanol, ethylene glycol, diethylene glycol, 1,2-propylene glycol, 1,2-dipropylene glycol and mixtures thereof.

The inventive polymer composition is suitable for production of coatings on substrates, such as washing, cleaning or dishwashing composition tablets. The coatings obtained are water-soluble under the use conditions. The coatings are not brittle and generally feel pleasantly smooth.

For application of the coating to a substrate, the inventive polymer composition can be used in molten form or dissolved in a solvent or a solvent mixture. Suitable application processes are known in principle to those skilled in the art and comprise customary spray and dip application processes. Preference is given to spray application. In that case, the polymer composition can be used in molten form.

Preferably, the polymer composition for spray application is in dissolved form in a solvent or a solvent mixture. Finally, the solvent or solvent mixture can be removed by evaporation.

Adhesive Composition

The inventive polymer composition is suitable for production of adhesive compositions which are adhesive, meaning that they are capable of bonding substrates, without any noticeable change in the substrates themselves, the coherence of the substrates bonded being determined by adhesive forces (attraction forces between adhesive and substrate) and cohesion (internal cohesion of the adhesive).

Polymer compositions for preparation of an adhesive composition are obtained by free-radical polymerization of a monomer composition M) comprising at least one α,β-ethylenically unsaturated carboxylic acid A) as defined above. Preferred monomers A) are selected from acrylic acid, methacrylic acid, itaconic acid, maleic acid and fumaric acid. The acid groups may be in protonated form or in the form of their salts, Preferably, the monomer composition comprises 0.5% to 15% by weight, more preferably 1% to 10% by weight, based on the total weight of the monomer composition, of at least one α,β-ethylenically unsaturated carboxylic acid A). Particular preference is given to acrylic acid.

Suitable comonomers are, for example, alkyl (meth)acrylates having a $C_1$-$C_{10}$-alkyl radical, such as methyl methacrylate, methyl acrylate, n-butyl acrylate, ethyl acrylate and ethylhexyl acrylate. In particular, mixtures of alkyl (meth)acrylates are also suitable. Vinyl esters of carboxylic acids having 1 to 20 carbon atoms are, for example, vinyl laurate, vinyl stearate, vinyl propionate, vinyl versatate and vinyl acetate, Useful vinylaromatic compounds include vinyltoluene, α- and p-methylstyrene, α-butylstyrene, 4-n-butylstyrene, 4-n-decylstyrene and, preferably, styrene. Examples of nitriles are acrylonitrile and methacrylonitrile. The vinyl halides are ethylenically unsaturated compounds substituted by chlorine, fluorine or bromine, preferably vinyl chloride and vinylidene chloride. Examples of vinyl ethers include vinyl methyl ether or vinyl isobutyl ether. Preference is given to vinyl ethers of alcohols comprising 1 to 4 carbon atoms. Suitable hydrocarbons having 4 to 8 carbon atoms and two olefinic double bonds are, for example, butadiene, isoprene and chloroprene. Further monomers are, for example, also monomers comprising hydroxyl groups, especially $C_1$-$C_{10}$-hydroxyalkyl (meth)acrylates or (meth)acrylamide. Further monomers additionally include phenyloxyethyl glycol mono(meth)acrylate, glycidyl (meth)acrylate, aminoalkyl (meth)acrylates, for example 2-aminoethyl (meth)acrylate. Alkyl groups preferably have from 1 to 20 carbon atoms. Further monomers also include crosslinking monomers.

Preferred polyether components PE) are the aforementioned polyetherols and especially polyethylene glycols.

The type and amount of the monomers and the ratios of different comonomers to one another are such that the glass transition temperature is within the aforementioned range.

The inventive adhesive compositions may comprise at least one solvent or dispersant. The solvent or dispersant in the adhesive composition may consist either solely of water or mixtures of water and liquids miscible therewith, such as methanol or ethanol. Preference is given to using solely water. The pH of the adhesive composition is preferably adjusted to pH greater than 4.5, especially to a pH between 5 and 9.5.

The adhesive compositions may consist solely of the solvent and the polymer composition. The adhesive composition may, however, also comprise further additives, for example fillers, dyes, leveling agents, thickeners (preferably associative thickeners), defoamers, pigments, wetting agents or tackifiers (tackifying resins). For better wetting of the surfaces, the adhesives may comprise wetting aids, for example fatty alcohol ethoxylates, alkylphenol ethoxylates, nonylphenol ethoxylates, polyoxyethylenes, polyoxypropylenes or sodium dodecylsulfonate. The amount of additives is generally 0.05 to 5 parts by weight, especially 0.1 to 3 parts by weight, per 100 parts by weight of polymer composition (solid).

In one embodiment, the adhesive composition is essentially free of plasticizers. Plasticizers are additives which lower the adhesive power. "Essentially free of plasticizers" means that the compositions comprise less than 1% by weight, preferably less than 0.5% by weight, based on the overall composition, of plasticizers, and more preferably do not comprise any plasticizers.

The inventive adhesive composition is preferably a pressure-sensitive adhesive. A pressure-sensitive adhesive is a viscoelastic adhesive which sets to form a film at room temperature (20° C.) that remains permanently tacky and adhesive in the dry state. Adhesion to substrates is effected immediately by gentle pressure.

The inventive adhesive composition can be used to bond at least two substrates or to produce self-adhesive articles. The substrates or self-adhesive articles to be bonded are at least partly coated with the pressure-sensitive adhesive. Preferably, the self-adhesive articles are redetachable after bonding. The self-adhesive articles may, for example, be films, tapes or labels. Suitable carrier materials are, for example, paper, polymer films and metal foils. The inventive self-adhesive tapes may be tapes of the above substances coated on one or both sides. Inventive self-adhesive labels may be labels made of paper or a thermoplastic film. Useful thermoplastic films include, for example, films of polyolefins (e.g. polyethylene, polypropylene), polyolefin copolymers, films of polyesters (e.g. polyethylene terephthalate) or polyacetate. The surfaces of the thermoplastic polymer films have preferably been corona-treated. The labels have been coated with adhesive on one side. Preferred substrates for the self-adhesive articles are paper and polymer films. Preferred self-adhesive articles are paper labels. The articles have been coated at least partly with an inventive adhesive composition on at least one surface. The adhesive can be applied to the articles by customary methods such as knife coating or spreading. The amount applied is preferably 0.1 to 20 g, more preferably 2 to 15 g, of solid per m². The application may be followed by a drying step to remove the water or the solvents. The substrates which are bonded to one another or to which the self-adhesive articles can advantageously be applied may, for example, be metal, wood, glass, paper or plastic. The self-adhesive articles are especially suitable for bonding to packaging surfaces, cardboard boxes, plastic packaging, books, windows, vehicle bodies or vehicle body parts. The self-adhesive articles of specific embodiments can be pulled off the articles again by hand, without any adhesive residue remaining on the article. The adhesion to the articles is good; nevertheless, it is easily possible to pull off the films, tapes and labels.

Cosmetic and Pharmaceutical Compositions

The inventive polymer compositions are preferentially suitable for formulation of cosmetic and pharmaceutical products, especially aqueous cosmetic and pharmaceutical products.

The invention further provides a cosmetic or pharmaceutical preparation comprising a) at least one inventive polymer composition as defined above,
b) at least one cosmetically or pharmaceutically acceptable active ingredient, and
c) optionally at least one cosmetically or pharmaceutically acceptable auxiliary other than components a) and b).

Preferably, component c) comprises at least one cosmetically or pharmaceutically acceptable carrier.

Preferably, the carrier component c) is selected from
i) water,
ii) water-miscible organic solvents, preferably $C_2$-$C_4$-alkanols, especially ethanol,
iii) oils, fats, waxes,
iv) esters, other than iii), of $C_6$-$C_{30}$-monocarboxylic acids with mono-, di- or trihydric alcohols,
v) saturated acyclic and cyclic hydrocarbons,
vi) fatty acids,
vii) fatty alcohols,
viii) propellant gases,
and mixtures thereof.

Suitable hydrophilic components c) are the aforementioned organic solvents, oils and fats.

Especially suitable cosmetically acceptable oil and fat components c) are described in Karl-Heinz Schrader, Grundlagen und Rezepturen der Kosmetika, 2nd edition, Verlag Hüthig, Heidelberg, p. 319-355, which is hereby incorporated by reference.

The inventive cosmetic compositions may be skin-cosmetic, hair-cosmetic, dermatological, hygiene or pharmaceutical products. The inventive polymer composition is especially also suitable for formulation of gels.

The inventive products are preferably in the form of a gel, foam, spray, ointment, cream, emulsion, suspension, lotion, milk or paste. If desired, it is also possible to use liposomes or microspheres. The inventive polymer composition is especially suitable for formulation of gels.

The inventive cosmetic compositions may additionally comprise cosmetic and/or dermatological active and effective substances, and also auxiliaries. Preferably, the inventive cosmetic compositions comprise at least one inventive polymer composition, as defined above, at least one carrier C) as defined above and at least one different constituent preferably selected from cosmetic active ingredients, emulsifiers, surfactants, preservatives, perfume oils, additional thickeners, hair polymers, hair and skin conditioners, graft polymers, water-soluble or dispersible silicone-containing polymers, light stabilizers, bleaches, gel formers, care agents, tints, tanning agents, dyes, pigments, consistency regulators, humectants, refatting agents, collagen, protein hydrolyzates, lipids, antioxidants, defoamers, antistats, emollients and softeners.

In addition to the inventive polymer compositions, the cosmetic compositions may comprise at least one conventional thickener. These include, for example, polysaccharides and organic sheet minerals such as Xanthan Gum® (Kelzan® from Kelco), Rhodopol® 23 (Rhone Poulenc) or Veegum® (from R. T. Vanderbilt) or Attaclay® (from Engelhardt). Suitable thickeners are also organic natural thickeners (agar-agar, carrageenan, tragacanth, gum arabic, alginates, pectins, polyoses, guar flour, carob seed flour, starch, dextrins, gelatin, casein) and inorganic thickeners (polysilicic acids, clay minerals such as montmorillonites, zeolites, silicas). Further thickeners are polysaccharide gums, for example gum arabic, agar, alginates, carrageenans and salts thereof, guar, guaran, tragacanth, gellan, ramsan, dextran or xanthan and derivatives thereof, for example propoxylated guar, and mixtures thereof. Other polysaccharide thickeners are, for example, starches of a wide variety of different origins and starch derivatives, for example hydroxyethyl starch, starch phosphate esters or starch acetates, or carboxymethyl cellulose or the sodium salt thereof, methyl cellulose, ethyl cellulose, hydroxyethyl cellulose, hydroxypropyl cellulose, hydroxypropyl methyl cellulose or hydroxyethyl methyl cellulose, or cellulose acetate. The thickeners used may additionally be sheet silicates. These include, for example, the magnesium or sodium-magnesium sheet silicates obtainable under the Laponite® trade name from Solvay Alkali, and the magnesium silicates from Sṻd-Chemie.

Suitable cosmetically and/or dermatologically active ingredients are, for example, skin and hair pigmenting agents, tanning agents, bleaches, keratin-hardening substances, antimicrobials, light filtering agents, repellent agents, hyperemic agents, keratolytic and keratoplastic agents, antidandruff agents, antiphlogistics, keratinizing agents, antioxidant and free radical-scavenging agents, skin moisturizers or humectants, refatting agents, deodorizing agents, sebostatic agents, plant extracts, antierythematously or antiallergically active ingredients and mixtures thereof.

Artificial tanning agents suitable for tanning the skin without natural or artificial irradiation with UV rays are, for example, dihydroxyacetone, alloxane and walnut shell extract. Suitable keratin-hardening substances are generally active ingredients as also used in antiperspirants, for example potassium aluminum sulfate, aluminum hydroxychloride, aluminum lactate, etc. Antimicrobials are used to destroy microorganisms or to inhibit their growth and thus serve both as a preservative and as a deodorant which reduces the formation or intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable light filtering agents are substances which absorb UV rays in the UV-B and/or UV-A region. Suitable UV filters are those mentioned above. Additionally suitable are p-aminobenzoic esters, cinnamic esters, benzophenones, camphor derivatives, and pigments which stop UV rays, such as titanium dioxide, talc and zinc oxide. Suitable repellent agents are compounds capable of warding off or driving away certain animals, particularly insects, from humans. These include, for example, 2-ethyl-1,3-hexanediol, N,N-diethyl-m-toluamide etc. Suitable substances with hyperemic activity, which stimulate blood flow through the skin are, for example, essential oils, such as dwarf pine, lavender, rosemary, juniperberry, roast chestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff agents are, for example, sulfur, sulfur polyethylene glycol sorbitan monooleate, sulfur ricinol polyethoxylate, zinc pyrithione, aluminum pyrithione, etc. Suitable antiphlogistics, which counter skin irritations, are, for example, allantoin, bisabolol. Dragosantol, camomile extract, panthenol, etc.

The inventive cosmetic compositions may comprise, as a cosmetically active ingredient (and optionally also as an auxiliary), at least one cosmetically or pharmaceutically acceptable polymer. These include, in quite general terms, anionic, cationic, amphoteric and uncharged polymers.

Examples of anionic polymers are copolymers of acrylic acid and acrylamide and salts thereof; sodium salts of polyhydroxycarboxylic acids, water-soluble or water-dispersible polyesters, polyurethanes, e.g. Luviset PUR® from BASF, and polyureas. Particularly suitable polymers are copolymers oft-butyl acrylate, ethyl acrylate, methacrylic acid (e.g. Luvimer® 100P), copolymers of ethyl acrylate and methacrylic acid (e.g. Luvimer® MAE), copolymers of N-tert-butylacrylamide, ethyl acrylate, acrylic acid (Ultrahold® 8, strong), copolymers of vinyl acetate, crotonic acid and optionally further vinyl esters (e.g, Luviset® products), maleic anhydride copolymers, optionally reacted with alcohol, anionic polysiloxanes, e.g. carboxy-functional, t-butyl acrylate, methacrylic acid (e.g. Luviskol® VBM), copolymers of acrylic acid and methacrylic acid with hydrophobic monomers, for example $C_4$-$C_{30}$-alkyl esters of (meth)acrylic acid, $C_4$-$C_{30}$-alkyl vinyl esters. $C_4$-$C_{30}$-alkyl vinyl ethers and hyaluronic acid. Another example of an anionic polymer is the methyl methacrylate/methacrylic acid/acrylic acid/ urethane acrylate copolymer obtainable under the Luviset@ Shape name (INCI Name: Polyacrylate-22). Further examples of anionic polymers are vinyl acetate/crotonic acid copolymers, as commercially available, for example, under the Resyn® (National Starch) and Gafset® (GAF) names, and vinylpyrrolidone/vinyl acrylate copolymers obtainable, for example, under the Luviflex® (BASF) trade name. Further suitable polymers are the vinylpyrrolidone/acrylate terpolymer available under the Luviflex® VBM-35 (BASF) name, and sodium sulfonate-containing polyamides or sodium sulfonate-containing polyesters. Additionally suitable are vinylpyrrolidone/ethyl methacrylate/methacrylic acid copolymers, as sold by Stepan under the Stepanhold-Extra and —R1 names, and the Carboset® products from BF Goodrich.

Suitable cationic polymers are, for example, cationic polymers having the INCI name Polyquaternium, e.g. copolymers of vinylpyrrolidone/N-vinylimidazolium salts (Luviquat® FC, Luviquat® HM, Luviquat® MS, Luviset Clear®, Luviquat Supreme®, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which form through reaction of polyvinylpyrrolidone with quaternary ammonium compounds), polymer JR (hydroxyethyl cellulose with cationic groups) and plant-based cationic polymers, e.g. guar polymers, such as the Jaguar® products from Rhodia.

Very particularly suitable polymers are uncharged polymers such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and salts thereof, polyvinylamines and salts thereof, cellulose derivatives, polyaspartic salts and derivatives. Examples of these include Luviflex® Swing (partly hydrolyzed copolymer of polyvinyl acetate and polyethylene glycol, from BASF).

Suitable polymers are also nonionic, water-soluble or water-dispersible polymers or oligomers, such as polyvinylcaprolactam, Luviskol® Plus (BASF SE), or polyvinylpyrrolidone and copolymers thereof, especially with vinyl esters such as vinyl acetate, e.g. Luviskol® VA 37, VA 55, VA 64, VA 73 (BASF SE); polyamides, for example based on itaconic acid and aliphatic diamines, as described, for example, in DE-A-43 33 238.

Suitable polymers are also amphoteric or zwitterionic polymers, such as the octyl acrylamide/methyl methacrylate/tert-butylaminoethyl methacrylate/2-hydroxypropyl methacrylate copolymers obtainable under the Amphomer® names (National Starch), and zwitterionic polymers as disclosed, for example, in German patent applications DE 39 29 973, DE 21 50 557. DE 28 17 369 and DE 37 08 451.

Acrylamidopropyltrimethylammonium chloride/acrylic acid or methacrylic acid copolymers and alkali metal and ammonium salts thereof are preferred zwitterionic polymers. Further suitable zwitterionic polymers are methacryloylethyl betaine/methacrylate copolymers, commercially available under the Amersette® name (AMERCHOL), and copolymers of hydroxyethyl methacrylate, methyl methacrylate. N,N-dimethylaminoethyl methacrylate and acrylic acid (Jordapon®).

Suitable polymers are also nonionic, siloxane-containing, water-soluble or -dispersible polymers, for example polyethersiloxanes such as Tegopren® (Goldschmidt) or Belsil® (Wacker).

In a specific execution, the inventive compositions comprise at least one polymer which acts as a thickener.

Suitable polymeric thickeners are, for example, optionally modified polymeric natural substances (carboxymethyl cellulose and other cellulose ethers, hydroxyethyl and hydroxypropyl cellulose and the like) and synthetic polymeric thickeners (polyacrylic and polymethacrylic compounds, vinyl polymers, polycarboxylic acids, polyethers, polyimines, polyamides). These include the polyacrylic and polymethacrylic compounds, some of which have already been mentioned above, for example the high molecular weight homopolymers of acrylic acid crosslinked with a polyalkenyl polyether, especially an allyl ether of sucrose, pentaerythritol or propylene (INCI name: Carbomer). Polyacrylic acids of this kind are obtainable, inter alia, from BF Goodrich under the Carbopol® trade name, e.g. Carbopol 940 (molecular weight about 4 000 000 daltons), Carbopol 941 (molecular weight about 1 250 000 daltons) or Carbopol 934 (molecular weight about 3 000 000 daltons). These additionally include acrylic acid copolymers obtainable, for example, from Rohm & Haas under the Aculyn and Acusol® trade names, for example the anionic, non-associative polymers Aculyn 22, Aculyn 28, Aculyn 33 (crosslinked), Acusol 810, Acusol 823 and Acusol 830 (CAS 25852-37-3). Also especially suitable are associative thickeners, for example based on modified polyurethanes (HEUR) or hydrophobically modified acrylic or methacrylic acid copolymers (HASE thickeners, High Alkali Swellable Emulsion).

In a preferred embodiment, the inventive product is a skin cleanser.

Preferred skin cleansers are soaps of liquid to gel consistency, such as transparent soaps, luxury soaps, deodorant soaps, cream soaps, baby soaps, skin protection soaps, abrasive soaps and syndets, pasty soaps, greasy soaps and washing pastes, liquid washing, showering and bathing preparations, such as washing lotions, shower baths and gels, foam baths, oil baths and scrub preparations, shaving foams, lotions and creams.

In a further preferred embodiment, the inventive products are cosmetic compositions for care and protection of the skin, nail care products or preparations for decorative cosmetics.

Suitable skin-cosmetic compositions are, for example, face tonics, face masks, deodorants and other cosmetic lotions. Products for use in decorative cosmetics comprise, for example, concealing sticks, stage makeup, mascara and eyeshadow, lipsticks, kohl pencils, eyeliners, blushers, powders and eyebrow pencils.

In addition, the inventive polymer compositions can be used in nose strips for pore cleansing, in antiacne compositions, repellents, shaving compositions, hair removal compositions, intimate care compositions, footcare compositions, and in babycare.

More particularly, the inventive skincare products are W/O or O/W skin creams, day and night creams, eye creams, face creams, antiwrinkle creams, moisturizing creams, bleaching creams, vitamin creams, skin lotions, care lotions and moisturizing lotions.

Skin-cosmetic and dermatological products based on the above-described inventive polymer compositions show advantageous effects. One effect of the polymers is to contribute to the moisturization and conditioning of the skin and to an improvement in the feel of the skin. Through addition of the inventive polymers, it is possible in certain formulations to achieve a considerable improvement in skin compatibility.

Skin-cosmetic and dermatological products comprise preferably at least one inventive polymer composition in a proportion of about 0.001 to 30% by weight, preferably 0.01 to 20% by weight, most preferably 0.1 to 12% by weight, based on the total weight of the product.

According to the field of use, the inventive compositions can be applied in a form suitable for skincare, for example in the form of a cream, foam, gel, stick, mousse, milk, spray (pump spray or propellant-containing spray) or lotion.

As well as the inventive polymer compositions and suitable carriers, the skin-cosmetic preparations may also comprise further active ingredients and auxiliaries customary in skin cosmetics, as described above. These preferably include emulsifiers, preservatives, perfume oils, cosmetic active ingredients such as phytantriol, vitamin A, E and C, retinol, bisabolol, panthenol, light stabilizers, bleaches, tanning agents, collagen, protein hydrolyzates, stabilizers, pH regulators, dyes, salts, thickeners, gel formers, consistency regulators, silicones, humectants, refatting agents and further customary additives.

Preferred oil and fat components of the skin-cosmetic and dermatological products are the aforementioned mineral and synthetic oils, for example paraffins, silicone oils and aliphatic hydrocarbons having more than 8 carbon atoms, animal and vegetable oils, for example sunflower oil, coconut oil, avocado oil, olive oil, lanolin, or waxes, fatty acids, fatty acid esters, for example triglycerides of $C_6$-$C_{30}$ fatty acids, wax esters, for example jojoba oil, fatty alcohols, vaseline, hydrogenated lanolin and acetylated lanolin, and mixtures thereof.

It is also possible to blend the inventive polymer composition with conventional polymers, as described above, if specific properties are to be established.

To establish particular properties, for example improving the tactile properties, the spreading characteristics, the water resistance and/or the binding of active ingredients and auxiliaries, such as pigments, the skin-cosmetic and dermatological preparations may additionally also comprise conditioning substances based on silicone compounds. Suitable silicone compounds are, for example, polyalkylsiloxanes, polyarylsiloxanes, polyarylalkylsiloxanes, polyethersiloxanes or silicone resins.

The cosmetic or dermatological preparations are produced by customary methods known to those skilled in the art.

Preferably, the cosmetic and dermatological products are in the form of emulsions, especially of water-in-oil (W/O) or oil-in-water (O/W) emulsions. However, it is also possible to choose other types of formulation, for example hydrodispersions, gels, oils, oleogels, multiple emulsions, for example in the form of W/O/W or O/W/O emulsions, anhydrous ointments or ointment bases, etc.

The emulsions are produced by known methods. As well as at least one inventive polymer composition, the emulsions generally comprise customary constituents such as fatty alcohols, fatty acid esters and especially fatty acid triglycerides, fatty acids, lanolin and derivatives thereof, natural or synthetic oils, or waxes and emulsifiers in the presence of water. The selection of additives specific to the type of emulsion and the production of suitable emulsions is described, for example, in Schrader, Grundlagen und Rezepturen der Kosmetika, Hüthig Buch Verlag, Heidelberg, 2nd edition, 1989, part three, which is hereby explicitly incorporated by reference.

A suitable emulsion, for example for a skin cream etc., generally comprises an aqueous phase which has been emulsified by means of a suitable emulsifier system in an oil phase or fatty phase.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, ho us oil; mineral oils having an initial boiling point under atmospheric pressure of about 250° C. and a final boiling point of 410° C., for example vaseline oil; esters of saturated or unsaturated fatty acids, such as alkyl myristates, e.g. isopropyl, butyl or cetyl myristate, hexadecyl stearate, ethyl or isopropyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

It is also possible to use waxes, for example carnauba wax, candililla wax, beeswax, microcrystalline wax, ozocerite wax and Ca. Mg and Al oleates, myristates, linoleates and stearates.

In addition, an inventive emulsion may take the form of an O/W emulsion. Such an emulsion typically comprises an oil phase, emulsifiers which stabilize the oil phase in the water phase, and an aqueous phase which is usually in thickened form. Useful emulsifiers are preferably O/W emulsifiers, such as polyglyceryl esters, sorbitan esters or partly esterified glycerides.

In a further preferred embodiment, the inventive products are a shower gel, a shampoo formulation or a bathing preparation.

Formulations of this kind comprise at least one inventive polymer composition and typically anionic surfactants as base surfactants and amphoteric and/or nonionic surfactants as cosurfactants. Further suitable active ingredients and/or auxiliaries are generally selected from lipids, perfume oils, dyes, organic acids, preservatives and antioxidants, and also thickeners/gel formers, skin conditioners and moisturizers.

These formulations comprise preferably 2% to 50% by weight, preferably 5% to 40% by weight, more preferably 8% to 30% by weight, of surfactants, based on the total weight of the formulation.

In the washing, showering and bathing preparations, it is possible to use any of the anionic, uncharged, amphoteric or cationic surfactants customarily used in personal care products.

Suitable surfactants are those mentioned above.

In addition, the shower gel/shampoo formulations may comprise further thickeners, for example sodium chloride, PEG-55, propylene glycol oleate, PEG-120 methylglucose dioleate and others, and also preservatives, further active ingredients and auxiliaries and water.

In a further preferred embodiment, the inventive product is a hair treatment product.

Inventive hair treatment compositions preferably comprise at least one inventive polymer composition in an amount in the range from about 0.1% to 30% by weight, preferably 0.5% to 20% by weight, based on the total weight of the product.

Preferably, the inventive hair treatment compositions are in the form of a setting foam, hair mousse, hair gel, shampoo, hairspray, hair foam, end fluid, neutralizer for permanent waves or hot-oil treatment. According to the area of application, the hair-cosmetic preparations can be applied in the form of (aerosol) spray, (aerosol) foam, gel, gel spray, cream, lotion or wax. Hairsprays encompass both aerosol sprays and pump sprays without propellant gas. Hair foams encompass both aerosol foams and pump foams without propellant gas. Hairsprays and hair foams preferably comprise predominantly or exclusively water-soluble or water-dispersible components. If the compounds used in the inventive hairsprays and hair foams are water-dispersible, they can be employed in the form of aqueous microdispersions having particle diameters of typically 1 to 350 nm, preferably 1 to 250 nm. The solids contents of these preparations are typically within a range from about 0.5% to 20% by weight. These microdispersions generally do not require any emulsifiers or surfactants for their stabilization.

In a preferred embodiment, the inventive hair-cosmetic formulations comprise
a) 0.05% to 5% by weight, preferably 0.1% to 3% by weight, of at least one inventive polymer composition,
b) 20% to 99.95% by weight of water and/or alcohol,
c) 0% to 50% by weight of at least one propellant gas,
d) 0% to 5% by weight of at least one emulsifier,
e) 0.05% to 5% by weight of at least one cosmetically active ingredient, and
f) 0% to 20% by weight, preferably 0.1% to 10% by weight, of at least one water-soluble or water-dispersible polymer other than a) to e) and g),
g) 0% to 45% by weight, preferably 0.05% to 25% by weight, o her constituents,
where components a) to g) add up to 100% by weight.

"Alcohol" is understood to mean any alcohols customary in cosmetics, e.g. ethanol, isopropanol, n-propanol.

"Further constituents" are understood to mean the additives customary in cosmetics, for example propellants, defoamers, interface-active compounds, i.e. surfactants, emulsifiers, foam formers and solubilizers. The interface-active compounds used may be anionic, cationic, amphoteric or uncharged. Further customary constituents may also be, for example, preservatives, perfume oils, opacifiers, active ingredients, UV filters, care substances such as panthenol, collagen, vitamins, protein hydrolyzates, alpha- and beta-hydroxycarboxylic acids, stabilizers, pH regulators, dyes, viscosity regulators, gel formers, salts, humectants, refatting agents, complexing agents and further customary additives.

Also included here are all the styling and conditioning polymers known in cosmetics which can be used in combination with the inventive polymers, if very specific properties are to be established.

Suitable conventional hair cosmetic polymers are, for example, the aforementioned cationic, anionic, uncharged, nonionic and amphoteric polymers, to which reference is made here.

To establish certain properties, the preparations may additionally also comprise conditioning substances based on silicone compounds. Suitable silicone compounds are, for example, polyalkylsiloxanes, polyarylsiloxanes, polyarylalkylsiloxanes, polyethersiloxanes, silicone resins or dimethicone copolyols (CTFA) and aminofunctional silicone compounds such as amodimethicones (CTFA).

The inventive polymer compositions are especially suitable as thickeners in hairstyling formulations, especially hair foams and hair gels.

Emulsifiers used may be any of the emulsifiers customarily used in hair foams. Suitable emulsifiers may be nonionic, cationic or anionic, or amphoteric.

The inventive polymer compositions are also suitable for styling gels. Additional gel formers used may be any of the gel formers customary in cosmetics. In this regard, reference is made to the aforementioned conventional thickeners.

The inventive polymer compositions are also suitable for shampoo formulations additionally comprising customary surfactants.

In the shampoo formulations, particular effects can be achieved using customary conditioners in combination with the inventive polymer compositions. Examples of these include the aforementioned cationic polymers with the INCI name Polyquaternium, especially copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). In addition, it is possible to use protein hydrolyzates, and conditioning substances based on silicone compounds, for example polyalkylsiloxanes, polyarylsiloxanes, polyarylalkylsiloxanes, polyethersiloxanes or silicone resins. Further suitable silicone compounds are dimethicone copolyols (CTFA) and aminofunctional silicone compounds such as amodimethicones (CTFA). In addition, it is possible to use cationic guar derivatives such as guar hydroxypropyltrimonium chloride (INCI).

The inventive polymer compositions are likewise suitable for use in pharmaceutical formulations of any kind and in the coating of such pharmaceutical formulations.

The invention further provides for the use of a compound of the formula (I) or of the formula (I.1) as defined above as an auxiliary in pharmacy.

Typical pharmaceutical compositions comprise
A) at least one inventive polymer composition as defined above,
B) at least one pharmaceutically acceptable active ingredient and
C) optionally at least one further pharmaceutically acceptable auxiliary other than A) and B).

Pharmaceutically acceptable auxiliaries C) are auxiliaries which are known to be usable in the field of pharmacy, food technology and related fields, especially those listed in the relevant pharmacopoeias (e.g. DAB, Ph. Eur., BP, NF), and other auxiliaries whose properties do not preclude a physiological application.

Suitable auxiliaries C) may be: lubricants, wetting agents, emulsifiers and suspension media, preservatives, antioxidants, antiirritants, chelating agents, emulsion stabilizers, film formers, gel formers, odor-masking agents, resins, hydrocolloids, solvents, solubilizers, neutralizers, permeation accelerators, pigments, quaternary ammonium compounds, refatting and superfatting agents, ointment, cream or oil bases, silicone derivatives, stabilizers, sterilizers, propellants, desiccants, opacifiers, additional thickeners, waxes, plasticizers, white oils. This kind of configuration is based on specialist knowledge, as represented, for example, in Fiedler, H. P. Lexikon der Hilfsstoffe für Pharmazie, Kosmetik and angrenzende Gebiete [Lexicon of Auxiliaries for Pharmacy, Cosmetics and Related Fields], 4th ed., Aulendorf: ECV-Editio-Kantor-Verlag, 1996.

To produce inventive pharmaceutical products, the active ingredients can be mixed or diluted with a suitable excipient. Excipients may be solid, semisolid or liquid materials which can serve as a vehicle, carrier or medium for the active ingredient. Further auxiliaries are added, if desired, in the manner known to the person skilled in the art. More particularly, these are aqueous solutions or solubilizates for oral or parenteral administration. Furthermore, the copolymers for use in accordance with the invention are also suitable for use in oral administration forms such as tablets, capsules, powders, solutions. Here, they can provide the sparingly soluble drug with increased bioavailability. In the case of parenteral administration, as well as solubilizates, it is also possible to use emulsions, for example fatty emulsions.

Pharmaceutical formulations of the type specified above can be obtained by processing the inventive polymer composition with pharmaceutically active ingredients by conventional methods and using known and new active ingredients.

Depending on the active ingredient, the content of at least one inventive polymer composition in the pharmaceutical compositions is in the range from 0.01% to 50% by weight, preferably 0.1% to 40% by weight, particularly preferably 1% to 30% by weight, based on the total weight of the product.

For production of the inventive pharmaceutical products, all pharmaceutically active ingredients and prodrugs are suitable in principle. These include benzodiazepines, antihypertensives, vitamins, cytostatics, especially taxol, anesthetics, neuroleptics, antidepressants, antibiotics, antimycotics, fungicides, chemotherapeutics, urologics, platelet aggregation inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, narcotics, antilipemics, liver therapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, perfusion promoters, diuretics, diagnostics, corticoids, cholinergics, biliary therapeutics, antiasthmatics, broncholytics, beta-receptor blockers, calcium antagonists, ACE inhibitors, arteriosclerosis remedies, antiphlogistics, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists and slimming drugs.

Examples of suitable pharmaceutically active ingredients are especially the active ingredients mentioned in paragraphs 0105 to 0131 of US 2003/0157170.

As well as use in cosmetics and in pharmacy, the inventive polymer compositions are also suitable in the food and drink sector. In the context of the present invention, food and drink preparations are also understood to mean food supplements, for example preparations comprising food and drink dyes and dietetic foods and drinks. Moreover, the inventive polymer compositions are also suitable for feed supplements for animal nutrition.

The inventive polymer compositions are also suitable for production of formulations of food supplements such as water-insoluble vitamins and provitamins such as vitamin A, vitamin A acetate, vitamin D, vitamin E, tocopherol derivatives such as tocopherol acetate, and vitamin K.

Outer Coatings for Pharmaceutical Administration Forms

The above-described polymer compositions are exceptionally suitable for production of pharmaceutical compositions. They serve, for example, as polymeric film formers, especially for production of coating films for pharmaceutical administration forms.

The formulation base for inventive coating films for pharmaceutical administration forms may comprise at least one of the further pharmaceutically acceptable auxiliaries mentioned above for the pharmaceutical formulations.

Suitable auxiliaries may be: flavorings, taste improvers, sweetening agents (sugars, sugar alcohols, sweeteners, for example aspartame, saccharin-Na, sodium cyclamate), glidants, wetting agents, release agents, plasticizers, antiadhesives, antioxidants, stabilizers, pore formers, neutralizing agents, brighteners, dyes, pigments, disinfectants or preservatives, thickeners, etc. Substances of this kind are described, for example, in Fiedler, H. P. Lexikon der Hilfsstoffe für Pharmazie, Kosmetik und angrenzende Gebiete, 4th edition, Aulendorf: ECV-Editio-Cantor-Verlag, 1996.

Customary amounts of the auxiliaries are within a range from 0% to 50% by weight, preferably 0% to 20% by weight, especially 0.01% to 10% by weight, based on the total weight of the coating film.

The coating films can be produced, for example, by intimately mixing an inventive polymer composition with at least one auxiliary. In a particularly preferred embodiment, the inventive polymer composition is used as it is, without prior drying, for production of a coating film. However, it is also possible first to subject an inventive polymer composition to a drying operation and to use the polymer composition thus obtained to produce a coating. The polymer composition can then be used, for example, in powder form or as a melt or solution for production of the coating.

The invention further provides a coating film comprising such an aqueous polymer composition or a polymer composition obtainable therefrom by drying.

The invention further provides a pharmaceutical composition comprising
A) at least one inventive polymer composition,
B) at least one pharmaceutically acceptable active ingredient and
C) optionally at least one pharmaceutically acceptable auxiliary, The inventive polymer compositions can serve in the pharmaceutical compositions, for example, to produce a binder or a coating film. The functional effect here generally arises as a result of drying and/or filming of the coating film or binder. This drying and/or filming may proceed, irrespective of the application process, through supply of energy. This can be effected via convection (heat), radiation (infrared or microwaves) or conduction. Water used as dispersant for application evaporates in the process, and reduced pressure can optionally also be applied in order to accelerate the evaporation.

The inventive coating film can be employed, for example, in powder form or as a melt through pelletization, casting, spreading, or by means of spray application. The inventive coating film may additionally comprise at least one further polymer component.

The inventive formulation is suitable for administering basically any desired pharmaceutically active ingredients which can preferably be administered in isolated or protected form, such as antidepressants, beta receptor blockers, antidiabetics, analgesics, antiphlogistics, antirheumatics, antihypotensives, antihyperkensives, psychopharmaceuticals, tranquilizers, antiemetics, muscle relaxants, glucocorticoids, drugs for treating Colitis ulcerosa or Crohn's disease, antiallergics, antibiotics, antiepileptics, anticoagulants, antimycotics, antitussives, arteriosclerosis drugs, diuretics, enzymes, enzyme inhibitors, gout remedies, hormones and inhibitors thereof, heart glycosides, immunotherapeutics and cytokines, laxatives, lipid-lowering agents, gastrointestinal therapeutics, migraine drugs, mineral substance preparations, otoiogics, drugs for Parkinson's disease, thyroid therapeutics, spasmolytics, thrombocyte aggregation inhibitors, vitamins, cytostatics and metastases inhibitors, phytopharmaceuticals, chemotherapeutics, nutraceuticals, vitamins, carotenoids and amino acids.

The inventive polymer compositions are preferably used for coating of tablets, extrudates, minitablets, capsules, soft capsules, granules, pellets, micropellets, microcapsules, crystals. Coated granules, pellets, micropellets, microcapsules, crystals can be blended with suitable auxiliaries and compressed to give tablets which disintegrate rapidly in water and release the coated fine moldings again. In this Way, it is possible to produce what are called MUPS forms, multiple unit particulate systems. These are tablets which, after being taken, disintegrate and release the subunits coated with an inventive coating composition, Of particular importance in this context are what are called oral dispersibles, i.e. tablets which disintegrate in the mouth within a short time and release taste-masked small moldings.

In a specific variant, the inventive polymer compositions are used for pelletizing active ingredients, optionally with corresponding auxiliaries, and the pellets are then compressed to give tablets.

The inventive polymer compositions can also be used to produce transdermal active ingredient patches or sprays, The embedding of agglomerates in polyethylene glycol or lipids is likewise suitable for producing suppositories or vaginal medicament forms.

Classes of active ingredients and substances which can often cause a bitter taste and can advantageously be formulated with the inventive coating film and binder are, for example:
analgesics and antirheumatics, such as paracetamol, diclofenac, aceclofenac, ibuprofen, ketoprofen, flubiprofen, acetylsalicylic acid, levacetylmethadol and oxycodone;
psychopharmaceuticals, such as promethazine, donepezil, modafinil, nefazodon, reboxetin, sertindol and sertralin;
antibiotics such as erythromycin, roxithromycin, clarithromycin, grepafloxacin, ciprofloxacin, levofloxacin, sparfloxacin, trovafloxacin and nevirapin;
beta blockers, such as propranolol, metoprolol, bisoprolol and nebivolol;
antidiabetics, such as metformin, miglitol and repaglinide;

H1-antihistamines, such as diphenhydramine, fexofenadine and mizolastin;

H2 antihistamines, such as cimetidine, famotidine, roxatidine, nizatidine, ticlopidine, cetirizine and ranitidine;

vitamins such as thiamine nitrate and quinidine sulfate, amyloprilose HCl, pseudoephedrine HCl, sildenafil, topiramate, granisetron, rebamipide, quinine HCl, etc.

The inventive coating films have a low water vapor and oxygen permeability and hence enable the formulation and stabilization of drugs that are particularly sensitive to water vapor or oxygen, for example acetylsalicylic acid, enalapril, cortisone acetate, omeprazole, carotenoids. In this case, the coating has protective character.

Moreover, the inventive coatings can be used for separating incompatible active ingredients or auxiliaries in administration forms by ensheathing one or more constituents and thus avoiding mutual contact.

The unexpectedly very good application properties of the inventive outer film coatings are enabled by exceptional homogeneous filming of the polymer composition, low tack of the films and good flexibility or extensibility of the coatings, so that the film coating does not tear even on swelling of the tablet or pellet core. In this context, the combination of high flexibility with extremely low tack is especially surprising, since polymers are normally either rigid, i.e. not very flexible, and non-tacky or soft, i.e. flexible, but tacky.

The polymer compositions are of low viscosity, meaning that high solids concentrations in the spray suspension and an extremely short spraying process can be achieved. The solids concentrations of the spray suspensions are typically 10% to 60% by weight, preferably 20% to 50% by weight and especially 25% to 40% by weight. The concentrations based on solid polymer containing amino groups used in accordance with the invention are typically within a range from 5% to 50% by weight, preferably from 10% to 40% by weight and especially from 20% to 35% by weight. The low viscosities ensure very fine and homogeneous atomization in the spray nozzle, very good spreading on the surface of the tablet or pellet and rapid and homogeneous filming. The incorporation of dyes and pigments is effected in the standard manner, but is extremely simple and rapid and is solvent-free. Simple handling results from the fact that the polymer compositions containing amino groups used in accordance with the invention stabilize the pigments in the spray suspension. Within about 10 min, a ready-to-spray suspension can thus be prepared.

The formulation base of inventive pharmaceutical compositions preferably comprises pharmaceutically acceptable auxiliaries. Pharmaceutically acceptable auxiliaries are auxiliaries which are known for use in the field of pharmacy, food technology and related fields, in particular those listed in the relevant pharmacopoeia (e.g. DAB, Ph. Eur. BP, USP, JP), and other auxiliaries whose properties do not preclude a physiological application.

Suitable auxiliaries may be: glidants, wetting agents, emulsifiers and suspending agents, preservatives, antioxidants, antiirritants, chelating agents, emulsion stabilizers, film formers, gel formers, odor masking agents, resins, hydrocolloids, solvents, solubilizers, neutralizing agents, permeation accelerators, pigments, dyes, stabilizers, disintegrants, drying agents, pacifiers, thickeners, waxes, plasticizers, aromas, sweeteners, auxiliaries for lowering permeation etc. This kind of configuration is based on specialist knowledge, as represented, for example, in Fiedler, H. P. Lexikon der Hilfsstoffe für Pharmazie. Kosmetik und angrenzende Gebiete, 4th ed., Aulendorf: ECV-Editio-Kantor-Verlag, 1996.

Particularly suitable plasticizers are, for example: triethyl citrate, tributyl citrate, triacetin, acetyl triethylcitrate, labrasol, glycofurol, polypropyleneglycol 400.

The permeability of the outer film coatings can be lowered further by incorporating inorganic solids (pigments, for example talc, kaolin, titanium dioxide) or lipophilic organic solids such as fats, waxes, glycerides, fatty acids, for example stearic acid, fatty alcohols, for example stearyl alcohol.

To produce the inventive pharmaceutical compositions, the active ingredients can be mixed or diluted with suitable auxiliaries (excipients). Auxiliaries may be solid or semisolid materials which can serve as a vehicle, carrier or medium for the active ingredient. Further auxiliaries are added, if desired, in the manner known to the person skilled in the art.

Similarly, it is also possible to produce veterinary medicine administration forms, especially rumen-stable forms, and also administration forms containing vitamins, carotenoids, trace elements, nutraceuticals, amino acids and food supplements. The latter can also serve as foods or supplements.

The invention further provides for the use of an inventive polymer composition, as defined above, for membrane production, in cosmetics, in crop protection, for seed coating, in food and drink, in animal nutrition, as adhesive raw materials, for papermaking, as a binder or auxiliary for leather and textiles, as a microbicidal surface coating, in the nonwovens sector, in washing and cleaning compositions, for production of paints, in the construction sector.

The invention is illustrated in detail by the figures described hereinafter and the examples. At the same time, the figures and examples should not be understood such that they restrict the invention.

In the figures and examples which follow, the following abbreviations are used:
EO: ethylene oxide
PO: propylene oxide
BO: butylene oxide
$M_n$: number-average molecular weight
$M_w$: weight-average molecular weight
PET: polyethylene terephthalate
$T_L$: transparency value
n.d.: not determined
rad/s: radiant per second
pphm: parts by weight per 100 parts by weight of monomer (parts per hundred monomer).

BRIEF DESCRIPTION OF FIGURES

FIG. 1 shows an image of a film based on the inventive polymer composition 10 before a white background with black text.

EXAMPLES

I) Analysis

I.a) Determination of Water Solubility

To determine water solubility, 5 g of the particular polymer composition were introduced into a 1 l beaker, and 900 ml of water which had been heated to 40° C. beforehand were added. The mixture was stirred with a magnetic stirrer at 40° C. for 20 minutes and the pH was adjusted to 8 with sodium hydroxide solution. Water-soluble polymer gels led to transparent or slightly cloudy solutions.

I.b) Determination of Weight-Average Molecular Weight ($M_w$)

The weight-average molecular weight of the polymer was determined by gel permeation chromatography (GPC). For this purpose, the following instruments and chromatography methods were used:
Standard: polyacrylic acid, neutralized
Eluent: 0.08 mol/l Tris, pH 7.0, +0.15 mol/l NaCl+0.01 mol/l $NaN_3$ in deionized water
Flow rate: 0.8 ml/min
Column set: 1 precolumn (l=5 cm), 2 separation columns (l=30 cm each)
Column temperature 35° C.
Detector: DRI (refractive index detector) Agilent 1100

I.c) Determination of Glass Transition Temperature ($T_g$)

The glass transition temperature was determined by means of dynamic differential calorimetry (DSC: Differential Scanning calorimetry) in a manner known per se. The DSC measurement was effected on thermally conditioned samples which had been heated to 100° C. and cooled rapidly before the actual measurement. The glass transition temperature was determined under nitrogen in open aluminum crucibles at a heating rate and cooling rate of 20 K/min.

I.d) Determination of Water Content after Drying

The water content of the particulate polymer was determined by coulometric means through Karl Fischer titration.

II) Preparation Examples

General Preparation Method

A glass reactor equipped with three feeds, nitrogen inlet and an anchor stirrer was initially charged with the polyether component (PE), the chain transfer agent (CTA) and the solvent (S) in an amount according to table 1 or table 2, purged with nitrogen for a couple of minutes and heated to 75° C. Subsequently, feeds 1-3 were added simultaneously to the initial charge at 75° C. and while stirring at 100 revolutions/minute within 4 hours. Feed 1 comprised monomer (M), feed 2 comprised an initiator (FRI) dissolved in a small amount of nonionic surfactant (PE) and/or solvent (S), and feed 3 comprised a further amount of chain transfer agent (CTA) and optionally solvent. After the addition of feeds 1, 2 and 3, the mixture was stirred at 75° C. and at 100 revolutions/minute for a further hour for continued polymerization. Subsequently, the polymer was poured into a beaker and cooled immediately to room temperature.

For production of the inventive polymer compositions, the following feedstocks were used:
M1: acrylic acid
M2: methacrylic acid
PE1: polyethylene oxide having $C_xH_{2x+1}/C_yH_{2y+1}$ termination at either end and having a free OH group and x, y=6-14.
PE2: $C_{13}$ oxo alcohol ethoxylate with 20 EO
PE3: propoxylated ethylene glycols having an E0 content of 50%
PE4: polyethylene glycol, molecular weight of 400 g/mol
PE5: polypropylene glycol, molecular weight of 400 g/mol
PE6: alkyl polyglucoside
R1: 2-mercaptoethanol
S1: water
S2: isopropanol
FRI1: tert-butyl peroxyneodecanoate (purity: 97%) (CAS No. 26748-41-4) FRI2: 2,2'-azobis(2-methylpropionamidine) dihydrochloride (CAS No. 2997-92-4)

The inventive polymer compositions of examples 1 to 15 were prepared by the general preparation method described above. The monomer component (M) used was acrylic acid or methacrylic acid. The (meth)acrylic acid used and the particular polyether component (PE) were added in the proportions by weight stated, with highly varying amounts of the solvent (S), the initiator (FRI), and the chain transfer agent (CTA) in the polymer mixtures. The amounts (in [g]) of the feedstocks are summarized in tables 1 and 2 below.

The polymer compositions of examples 1 to 9 were first obtained in the form of gels or of solvent-containing solids. After the synthesis, about 100 g in each case of the polymer compositions were poured into an aluminum dish and dried further in a drying cabinet first at 80° C. and standard pressure and then at 50° C. and 100 mbar. The solid polymer material thus obtained was comminuted in a mortar and pestle. The consistency and analytical parameters of the resulting solid polymer compositions are summarized in table 3 below.

TABLE 1

| | Initial charge | | | Feed 2 | | Feed 3 | |
|---|---|---|---|---|---|---|---|
| Ex. No. | PE [g] (PE no.) | S [g] (S no.) | Feed 1 M [g] | FRI [g] (FRI no.) | S [g] (S no.) | CTA [g] | S [g] (S no.) |
| 1 | 120 (1) | 162 (1) | 360 (1) | 8.45 (1) | 30 (2) | 18 (1) | — |
| 2 | 120 (1) | 162 (1) | 297 (1) + 63 (2) | 9.1 (2) | 41 (1) | 18 (1) | — |
| 3 | 120 (1) | 162 (1) | 252 (1) + 108 (2) | 9.1 (2) | 41 (1) | 18 (1) | — |
| 4 | 120 (1) | 162 (1) | 164 (1) + 196 (2) | 9.1 (2) | 41 (1) | 18 (1) | — |
| 5 | 200 (1) | 263 (1) | 158 (1) + 442 (2) | 15.2 (2) | 75 (1) | 30 (1) | — |
| 6 | 120 (1) | 162 (1) | 360 (2) | 9.1 (2) | 41 (1) | 18 (1) | — |
| 7 | 160 (1) | 162 (1) | 146 (1) + 174 (2) | 8.1 (2) | 42 (1) | 16 (1) | — |
| 8 | 150 (1) | 243 (1) | 273 (1) + 327 (2) | 15.2 (2) | 75 (1) | 30 (1) | — |
| 9 | 120 (1) | 231 (1) | 273 (1) + 327 (2) | 15.2 (2) | 75 (1) | 30 (1) | — |
| 10 | 256 (1) | 259 (1) | 512 (1) | 12 (1) | 41 (2) | 26 (1) | — |

TABLE 2

| | Initial charge | | | Feed 2 | | Feed 3 | |
|---|---|---|---|---|---|---|---|
| Ex. No. | PE [g] (PE no.) | S [g] (S no.) | Feed 1 M [g] | FRI [g] (FRI no.) | S [g] (S no.) | CTA [g] | S [g] (S no.) |
| 11 | 250 (2) | 247 (1) | 500 (1) | 3.55 (2) | 46 (1) | 10 (1) + 27 (2) | 28 (1) |
| 12 | 250 (3) | 247 (1) | 500 (1) | 3.55 (2) | 46 (1) | 10 (1) + 27 (2) | 28 (1) |
| 13 | 250 (4) | 247 (1) | 500 (1) | 3.55 (2) | 46 (1) | 10 (1) + 27 (2) | 28 (1) |
| 14 | 250 (5) | 247 (1) | 500 (1) | 3.55 (2) | 46 (1) | 10 (1) + 27 (2) | 28 (1) |
| 15 | 250 (6) | 247 (1) | 500 (1) | 3.55 (2) | 46 (1) | 10 (1) + 27 (2) | 28 (1) |

TABLE 3

| Ex. No. | Mw [g/mol] | Form | Tg [° C.] | H₂O conc. [%] |
|---|---|---|---|---|
| 1 | 5700 | pellets | 32 | 1.6 |
| 2 | 3800 | pellets | 44 | 1.2 |
| 3 | 4200 | pellets | 51 | 1.4 |
| 4 | 3500 | pellets | 60 | 1.8 |
| 5 | 4100 | pellets | 96 | n.d. |
| 6 | 3500 | pellets | 108 | 5.5 |
| 7 | 3700 | pellets | 39 | 1.9 |
| 8 | 4200 | pellets | 74 | n.d. |
| 9 | 4500 | pellets | 90 | n.d. |
| 10 | 4400 | film | 13 | n.d. | n.d. = not determined

III) Example for Production of Polymer Films

The polymer composition of example 10 was fully liquefied by heating to 80° C. and coated onto a flat Si surface with a 120 μm coating bar. Subsequently, the film was dried at room temperature for 24 hours. A flexible film was obtained, which had good water solubility at pH 8 and 40° C.

FIG. 1 shows an image of a film based on the inventive polymer composition 10 before a white background with black text.

IV) Example for Production of an Active Ingredient-Containing Polymer Film

The polymer composition of example 10 was liquefied by heating to 70° C. Then 1% (w/w) of the *Bacillus* sp. protease P3111 (Sigma Aldrich) enzyme was added while stirring, until a homogeneous mixture formed. The liquid polymer composition was coated onto a Si surface with a 120 μm coating bar and immediately cooled to room temperature. Subsequently, the film was dried at room temperature for 24 hours. A flexible film was obtained, which had good water solubility at pH 8 and 40° C. with release of the embedded enzyme (measured by the AAPF protease activity method) (AAPF=alanine(A)-alanine(A)-proline(P)-phenylalanine (F)).

The invention claimed is:

1. A process for preparing a polymer composition, comprising
   a) providing a monomer composition M) comprising
      A) at least one α,β-ethylenically unsaturated carboxylic acid, and
      B) less than 0.1% by weight, based on the total weight of the monomer composition M), of crosslinking monomers having two or more polymerizable α,β-ethylenically unsaturated double bonds per molecule,
      where component A) is optionally partly replaced by C) at least one unsaturated sulfonic acid or unsaturated phosphonic acid,
   b) subjecting the monomer composition M) provided in step a) to a free-radical polymerization in the presence of at least one polyether component PE), which does not have any copolymerizable double bonds, selected from the group consisting of polyetherols having a number-average molecular weight of at least 200 g/mol and the mono- and di-($C_1$-$C_6$-alkyl) ethers thereof, surfactants containing polyether groups and mixtures thereof.

2. The process according to claim 1, further comprising
   c) Converting the polymer obtained in step b) to a film, to a solid coating on a substrate or to particles.

3. The process according to claim 1, wherein the polyether component PE) comprises a polyetherol having repeat propylene oxide units or a mono- or di-($C_1$-$C_6$-alkyl ether) of a polyetherol having repeat propylene oxide units, and the proportion of these repeat propylene oxide units averages not more than 18 units per molecule.

4. The process according to claim 1, wherein the free-radical polymerization in step b) is additionally effected in the presence of a solvent S) selected from the group consisting of water, $C_1$-$C_6$-alkanols, polyols other than PE), the mono- and dialkyl ethers thereof, and mixtures thereof.

5. The process according to claim 1, wherein the α,β-ethylenically unsaturated carboxylic acid A) is selected from the group consisting of acrylic acid, methacrylic acid, ethacrylic acid, α-chloroacrylic acid, crotonic acid, maleic acid, itaconic acid, citraconic acid, mesaconic acid, glutaconic acid, aconitic acid, fumaric acid and mixtures thereof.

6. The process according to claim 1, wherein the monomer composition M) further comprises, as component C), at least one unsaturated sulfonic acid or unsaturated phosphonic acid.

7. The process according to claim 1, wherein the monomer composition M) comprises at least 80% by weight, based on the total weight of the monomer composition M), of at least one α,β-ethylenically unsaturated acid selected from the group consisting of acrylic acid, methacrylic acid, 2-acrylamido-2-methylpropanesulfonic acid and mixtures thereof.

8. The process according to claim 1, wherein the monomer composition M) comprises at least 80% by weight, based on the total weight of the monomer composition M), of acrylic acid.

9. The process according to claim 1, wherein the monomer composition M) further comprises at least one monomer D) selected from the group consisting of compounds of the general formulae (I.a) and (I.b)

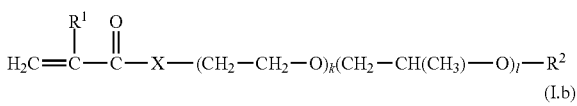

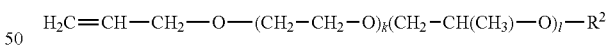

wherein
the sequence of the alkylene oxide units is arbitrary,
k and l are each independently an integer from 0 to 1000,
where the sum of k and l is at least 2,
$R^1$ is hydrogen or $C_1$-$C_8$-alkyl,
$R^2$ is hydrogen, $C_1$-$C_{30}$-alkyl, $C_2$-$C_{30}$-alkenyl or $C_5$-$C_8$-cycloalkyl,
X is O or a group of the formula $NR^3$ in which $R^3$ is H, alkyl, alkenyl, cycloalkyl, heterocycloalkyl, aryl or hetaryl.

10. The process according to claim 1, wherein the monomer composition M) further comprises at least one comonomer selected from the group consisting of
    E) vinylaromatics,
    F) $C_2$-$C_8$ monoolefins, nonaromatic hydrocarbons having at least two conjugated double bonds, G) esters of α,β-ethylenically unsaturated mono- and dicarboxylic acids with $C_1$-$C_{30}$-alkanols, H) compounds having one free-radically polymerizable α,β-ethylenically unsaturated double bond and at least one cationogenic and/or cationic group per molecule, I) esters of vinyl alcohol or allyl alcohol with $C_1$-$C_{30}$-monocarboxylic acids, K) monomers containing amide groups, L) esters of α,β-ethylenically unsaturated mono- and dicarboxylic acids with $C_2$-$C_{30}$-alkanediols, amides of α,β-ethylenically unsaturated mono- and dicarboxylic acids with $C_2$-$C_{30}$-amino alcohols having a primary or secondary amino group, M) α,β-ethylenically unsaturated nitriles, N) vinyl halides, vinylidene halides, O) monomers having urea groups, and mixtures thereof.

11. The process according to claim 1, wherein the monomer composition M) comprises acrylic acid and at least one comonomer selected from the group consisting of α,β-ethylenically unsaturated carboxylic acids other than acrylic acid and derivatives thereof, $C_2$-$C_{10}$-monoolefins, nonaromatic hydrocarbons having at least two conjugated double bonds, vinylaromatics, N-vinyllactams and mixtures thereof.

12. The process according to claim 1, wherein the polyether component PE) comprises at least one polyetherol having a number-average molecular weight in the range from about 200 to 100 000 g/mol or a mono- or di-($C_1$-$C_2$-alkyl ether) thereof.

13. The process according to claim 1, wherein the polyether component PE) comprises at least one polyetherol or a mono- or di-($C_1$-$C_2$-alkyl ether) thereof comprising exclusively ethylene oxide units as alkylene oxide units.

14. The process according to claim 1, wherein the polyether component PE) comprises at least one surfactant containing polyether groups, selected from the group consisting of alkyl polyoxyalkylene ethers, aryl polyoxyalkylene ethers, alkylaryl polyoxyalkylene ethers, alkoxylated animal and/or vegetable fats and/or oils, fatty amine alkoxylates, fatty acid amide alkoxylates, fatty acid diethanolamide alkoxylates, polyoxyethylene sorbitan fatty acid esters, alkyl polyether sulfates, aryl polyether sulfates, alkylaryl polyether sulfates, alkyl polyether sulfonates, aryl polyether sulfonates, alkylaryl polyether sulfonates, alkyl polyether phosphates, aryl polyether phosphates, alkylaryl polyether phosphates, glyceryl ether sulfonates, glyceryl ether sulfates, monoglyceride (ether) sulfates, fatty acid amide ether sulfates, polyoxyalkylene sorbitan fatty acid esters, and mixtures thereof.

15. The process according to claim 1, wherein the polyether component PE) comprises at least one surfactant containing polyether groups, selected from the group consisting of:

alkyl polyoxyalkylene ethers of the general formula (VI)

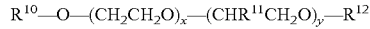

wherein $R^{10}$ is a linear or branched alkyl radical having 8 to 22 carbon atoms, $R^{11}$ and $R^{12}$ are each independently hydrogen or a linear or branched alkyl radical having 1-10 carbon atoms or H, and x and y are each independently 0 to 300, where the sum of x and y is >0;

surfactants containing hydroxyl groups of the general formula (VII)

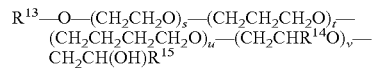

where the sequence of the alkylene oxide units in the compounds of the formula (VII) is arbitrary, s, t, u and v are each independently an integer from 0 to 500, where the sum of s, t, u and v is >0, $R^{13}$ and $R^{15}$ are each independently a straight-chain or branched saturated $C_1$-$C_{40}$-alkyl radical or a mono- or polyunsaturated $C_2$-$C_{40}$-alkenyl radical, and $R^{14}$ is methyl, ethyl, n-propyl, isopropyl or n-butyl;

fatty alcohol polyoxyalkylene esters of the general formula (VIII)

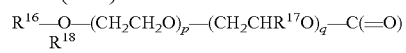

where the sequence of the alkylene oxide units in the compounds of the formula (VIII) is arbitrary, p and q are each independently an integer from 0 to 500, where the sum of p and q is >0, $R^{16}$ and $R^{18}$ are each independently a straight-chain or branched saturated $C_1$-$C_{40}$-alkyl radical or a mono- or polyunsaturated $C_2$-$C_{40}$-alkenyl radical, and $R^{17}$ is methyl, ethyl, n-propyl, isopropyl or n-butyl.

16. The process according to claim 1, wherein the at least one α,β-ethylenically unsaturated carboxylic acid is used in non-neutralized form for polymerization.

17. The process according to claim 1, wherein the free-radical polymerization in step b) is effected at a temperature in the range from 20 to 95° C.

18. The process according to claim 1, wherein the free-radical polymerization in step c) is effected in the presence of a solvent S) comprising at least 50% by weight, based on the total weight of the solvent S), of water.

19. The process according to claim 1, wherein the weight ratio of the monomer mixture M) to the component PE) is in the range from 1:10 to 10:1.

20. The process according to claim 18, wherein the weight ratio of the component PE) to the component S) is in the range from 0.3:1 to 5:1.

21. The process according to claim 18, wherein the free-radical polymerization in step b) is effected in feed mode, by initially charging at least a portion of the polyether component PE) and optionally, if present, at least a portion of the solvent S), and supplying at least a portion of the monomer composition provided in step a) and at least one free-radical initiator FRI) to the initial charge.

22. The process according to claim 1, wherein the free-radical polymerization in step b) is effected in feed mode, and feeds comprising at least one α,β-ethylenically unsaturated carboxylic acid do not comprise any solvent S).

23. The process of claim 1, further comprising:
c) subjecting the polymer obtained in step b), optionally after addition of at least one active and/or at least one additive, to a film-forming operation;
wherein A is at least one α,β-ethylenically unsaturated carboxylic acid.

24. The process of claim 1, further comprising
c) converting the polymer obtained in step b), optionally after addition of at least one active ingredient and/or at least one additive and/or at least one solvent and optionally while heating, to a free-flowing form
d) applying the polymer in free flowing form to a substrate, and
e) allowing the polymer to solidify;

wherein A is at least one α,β-ethylenically unsaturated carboxylic acid.

25. The process of claim 1, further comprising
c. converting the polymer obtained in step b), optionally after addition of at least one additive and/or at least one solvent and optionally while heating, to a free-flowing form and
d. forming a particulate composition from the polymer in free-flowing form.

26. A polymer composition in solid form, obtained by the process of claim 1.

27. The polymer composition according to claim 26, wherein the composition has a solubility in water at 40° C. and a pH of 8 of at least 5 g/l.

28. The polymer composition according to claim 26, wherein the weight-average molecular weight is 1000 to 150 000 daltons.

29. The polymer composition according to claim 26, wherein the composition has a solvent content of not more than 10% by weight, based on the total weight of polymer composition and solvent.

30. The polymer composition according to claim 26, wherein the composition has a content of acid groups of 1.5 mmol/g to 15 mmol/g.

31. The polymer composition of claim 26, wherein the composition is a film.

32. The polymer composition according to claim 31, wherein the composition has a transparency, reported as the $T_L$ measured at 500 nm, of at least 85%, based on the transparency of water.

33. The polymer composition of claim 31, comprising at least one active ingredient.

34. The polymer composition of claim 31, comprising at least one enzyme.

35. The polymer composition of claim 26, wherein the composition is a coating on a substrate.

36. The polymer composition of claim 35, comprising at least one active ingredient.

37. The polymer composition of claim 35, comprising at least one enzyme.

38. The polymer composition of claim 26, wherein the composition is in the form of a film or in the form of a coating on a substrate, wherein the thickness of the film or the coating is 0.5 μm to 10 mm.

39. The polymer composition of claim 38, having a glass transition temperature $T_G$ in the range from 0 to 50° C.

40. The polymer composition of claim 26, wherein the composition is in the form of a particulate solid substance.

41. The polymer composition of claim 40, comprising particles having a particle size within a range from 50 μm to 10 mm.

42. A washing and cleaning composition, dishwashing detergent, rinse aid, hygiene product, cosmetic composition, pharmaceutical composition, crop protection composition, wetting agent, lacquer, coating composition, adhesive, leather treatment composition, textile care composition, or composition for the development and/or exploitation of underground mineral oil and/or natural gas deposits, comprising the polymer composition of claim 26.

43. A liquid or solid washing composition or cleaning composition for solid surfaces comprising the polymer composition of claim 26.

44. A coating agent or as a component of a coating agent for a pharmaceutical composition, veterinary drugs or food, for production of coated tablets, pellets, microcapsules, pellets or crystals comprising the polymer composition of claim 26.

45. An enzyme-containing washing composition, cleaning composition, or dishwashing composition comprising the polymer composition of claim 26.

46. A sheath or coating for a washing composition portion, cleaning composition portion or dishwashing composition portion, consisting of the polymer composition of claim 26.

47. An adhesive composition comprising the polymer composition of claim 26.

* * * * *